(12) United States Patent
Estes

(10) Patent No.: US 11,957,874 B2
(45) Date of Patent: Apr. 16, 2024

(54) INFUSION PUMP SYSTEM AND METHODS

(71) Applicant: Insulet Corporation, Acton, MA (US)

(72) Inventor: Mark C. Estes, Malibu, CA (US)

(73) Assignee: INSULET CORPORATION, Acton, MA (US)

( * ) Notice: Subject to any disclaimer, the term of this patent is extended or adjusted under 35 U.S.C. 154(b) by 946 days.

(21) Appl. No.: 16/928,213

(22) Filed: Jul. 14, 2020

(65) Prior Publication Data
US 2020/0338266 A1    Oct. 29, 2020

Related U.S. Application Data

(60) Division of application No. 15/811,909, filed on Nov. 14, 2017, now abandoned, which is a continuation of application No. 14/804,563, filed on Jul. 21, 2015, now Pat. No. 9,844,627, which is a continuation of application No. 13/613,846, filed on Sep. 13, 2012,
(Continued)

(51) Int. Cl.
| | |
|---|---|
| A61M 5/172 | (2006.01) |
| A61B 34/10 | (2016.01) |
| A61M 5/14 | (2006.01) |
| A61M 5/142 | (2006.01) |
| G16H 20/17 | (2018.01) |

(Continued)

(52) U.S. Cl.
CPC .......... *A61M 5/1723* (2013.01); *A61B 34/10* (2016.02); *A61M 5/1413* (2013.01); *A61M 5/14244* (2013.01); *G16H 20/17* (2018.01); *G16H 40/63* (2018.01); *A61M 2005/14208* (2013.01); *A61M 2005/14268* (2013.01); *A61M 5/14566* (2013.01); *A61M 2202/0007* (2013.01); *A61M 2205/18* (2013.01); *A61M 2205/33* (2013.01); *A61M 2230/201* (2013.01)

(58) Field of Classification Search
None
See application file for complete search history.

(56) References Cited

U.S. PATENT DOCUMENTS

| | | | | |
|---|---|---|---|---|
| 3,886,938 A | * | 6/1975 | Szabo | A61M 5/1454 604/135 |
| 4,300,554 A | * | 11/1981 | Hessberg | A61M 5/1454 604/135 |

(Continued)

FOREIGN PATENT DOCUMENTS

| | | |
|---|---|---|
| EP | 0-062-974 | 10/1982 |
| EP | 0-275-213 | 7/1988 |

(Continued)

OTHER PUBLICATIONS

"Which Insulin Pump is Right for Me?", Albany Medical Center, Goodman Diabetes Service, Jan. 2006, 4 pages.
(Continued)

*Primary Examiner* — Manuel A Mendez
(74) *Attorney, Agent, or Firm* — GOODWIN PROCTER LLP

(57) ABSTRACT

Some embodiments an infusion pump system can be configured to modify alarm limit parameters as the user's insulin load increases or decreases. Moreover, in particular embodiments, the infusion pump system can be configured to provide a "missed bolus" or "missed meal" alarm in response to the user's blood glucose characteristics, the user's insulin load information, or the like.

20 Claims, 19 Drawing Sheets

Related U.S. Application Data now Pat. No. 9,114,210, which is a continuation of application No. 12/251,629, filed on Oct. 15, 2008, now Pat. No. 8,287,487.

(51) Int. Cl.
*G16H 40/63* (2018.01)
*A61M 5/145* (2006.01)

(56) References Cited

U.S. PATENT DOCUMENTS

| | | | |
|---|---|---|---|
| 4,435,173 A * | 3/1984 | Siposs | A61M 5/1456 |
| | | | D24/111 |
| 4,493,704 A * | 1/1985 | Beard | A61M 5/1452 |
| | | | 604/154 |
| 4,529,401 A * | 7/1985 | Leslie | A61M 5/1456 |
| | | | 604/67 |
| 5,822,715 A | 10/1998 | Worthington et al. | |
| 5,925,018 A * | 7/1999 | Ungerstedt | A61M 5/1456 |
| | | | 604/154 |
| 5,984,894 A * | 11/1999 | Poulsen | A61M 5/1413 |
| | | | 604/67 |
| 6,379,301 B1 | 4/2002 | Worthington et al. | |
| 6,544,212 B2 | 4/2003 | Galley et al. | |
| 6,551,276 B1 | 4/2003 | Mann | |
| 6,554,798 B1 | 4/2003 | Mann et al. | |
| 6,659,978 B1 | 12/2003 | Kasuga | |
| 6,691,043 B2 | 2/2004 | Ribeiro, Jr. | |
| 6,744,350 B2 | 6/2004 | Blomquist | |
| 6,872,200 B2 | 3/2005 | Mann et al. | |
| 6,852,104 B2 | 8/2005 | Blomquist | |
| 6,925,393 B1 | 8/2005 | Kalatz et al. | |
| 6,936,029 B2 | 8/2005 | Mann et al. | |
| 6,979,326 B2 | 12/2005 | Mann et al. | |
| 6,997,920 B2 | 2/2006 | Mann et al. | |
| 7,025,743 B2 | 4/2006 | Mann et al. | |
| 7,109,878 B2 | 9/2006 | Mann et al. | |
| 7,204,823 B2 | 4/2007 | Estes et al. | |
| 7,278,983 B2 | 10/2007 | Ireland et al. | |
| 7,291,107 B2 | 11/2007 | Hellwig et al. | |
| 7,399,277 B2 | 7/2008 | Saidara et al. | |
| 7,704,226 B2 | 4/2010 | Mueller et al. | |
| 7,785,313 B2 | 8/2010 | Mastro to taro | |
| 7,879,026 B2 * | 2/2011 | Estes | A61M 5/14244 |
| | | | 604/890.1 |
| 7,935,076 B2 | 5/2011 | Estes | |
| 7,959,598 B2 | 6/2011 | Estes | |
| 8,029,459 B2 | 10/2011 | Rush et al. | |
| 8,287,487 B2 | 10/2012 | Estes | |
| 9,114,210 B2 | 8/2015 | Estes | |
| 9,844,627 B2 | 12/2017 | Estes | |
| 2003/0114836 A1 | 6/2003 | Estes | |
| 2003/0125612 A1 | 7/2003 | Fox et al. | |
| 2003/0191376 A1 * | 10/2003 | Samuels | A61B 5/150099 |
| | | | 600/309 |
| 2004/0167464 A1 | 8/2004 | Ireland et al. | |
| 2004/0176720 A1 | 9/2004 | Kipfer | |
| 2005/0022274 A1 | 1/2005 | Campbell et al. | |
| 2005/0027182 A1 | 2/2005 | Siddiqui | |
| 2005/0038332 A1 | 2/2005 | Saidara et al. | |
| 2005/0245904 A1 | 11/2005 | Estes et al. | |
| 2006/0173406 A1 | 8/2006 | Hayes et al. | |
| 2007/0016170 A1 | 1/2007 | Kovelman | |
| 2007/0073228 A1 | 3/2007 | Memoe et al. | |
| 2007/0073235 A1 | 3/2007 | Estes et al. | |
| 2007/0073236 A1 | 3/2007 | Memoe et al. | |
| 2007/0118405 A1 | 5/2007 | Campbell et al. | |
| 2007/0124002 A1 | 5/2007 | Estes et al. | |
| 2007/0156092 A1 | 7/2007 | Estes | |
| 2007/0167912 A1 * | 7/2007 | Causey | A61M 5/172 |
| | | | 604/232 |
| 2007/0173761 A1 | 7/2007 | Kanderian, Jr. et al. | |
| 2007/0179444 A1 | 8/2007 | Causey et al. | |
| 2007/0282299 A1 | 12/2007 | Hellwig | |
| 2008/0125700 A1 | 5/2008 | Moberg et al. | |
| 2008/0177165 A1 | 7/2008 | Blomquist et al. | |
| 2008/0183060 A1 * | 7/2008 | Steil | A61B 5/4839 |
| | | | 606/151 |
| 2008/0201325 A1 | 8/2008 | Doniger et al. | |
| 2008/0269672 A1 | 10/2008 | Say | |
| 2008/0269714 A1 | 10/2008 | Mastrototaro et al. | |
| 2008/0275384 A1 | 11/2008 | Mastro to taro | |
| 2008/0294094 A1 | 11/2008 | Mhatre et al. | |
| 2008/0294142 A1 | 11/2008 | Patel et al. | |
| 2008/0306434 A1 | 12/2008 | Dobbles et al. | |
| 2009/0005726 A1 | 1/2009 | Jones et al. | |
| 2009/0036828 A1 | 2/2009 | Hansen et al. | |
| 2009/0177147 A1 | 7/2009 | Blomquist | |
| 2010/0174266 A1 | 7/2010 | Estes | |
| 2011/0071464 A1 | 3/2011 | Palerm | |
| 2012/0259278 A1 | 10/2012 | Hayes et al. | |
| 2012/0265126 A1 | 10/2012 | Estes | |
| 2014/0107607 A1 | 4/2014 | Estes | |

FOREIGN PATENT DOCUMENTS

| | | |
|---|---|---|
| EP | 1-045-146 | 12/2000 |
| EP | 1 818 664 | 8/2007 |
| WO | 2004/056412 | 7/2004 |
| WO | 2008/094249 | 5/2007 |
| WO | 2004/110526 | 12/2007 |

OTHER PUBLICATIONS

"Using the Deltec Cozmo Insulin Pump Correction Bolus Feature" believed to be publicly available before May 5, 2008, pp. 36-41.

The International Bureau of WIPO, International Preliminary Report on Patentability for Application No. PCT/US2009/060845, dated Apr. 28, 2011, 9 pages.

European Office Action in European Application No. 09740808.2, dated Nov. 14, 2018, 9 pages.

\* cited by examiner

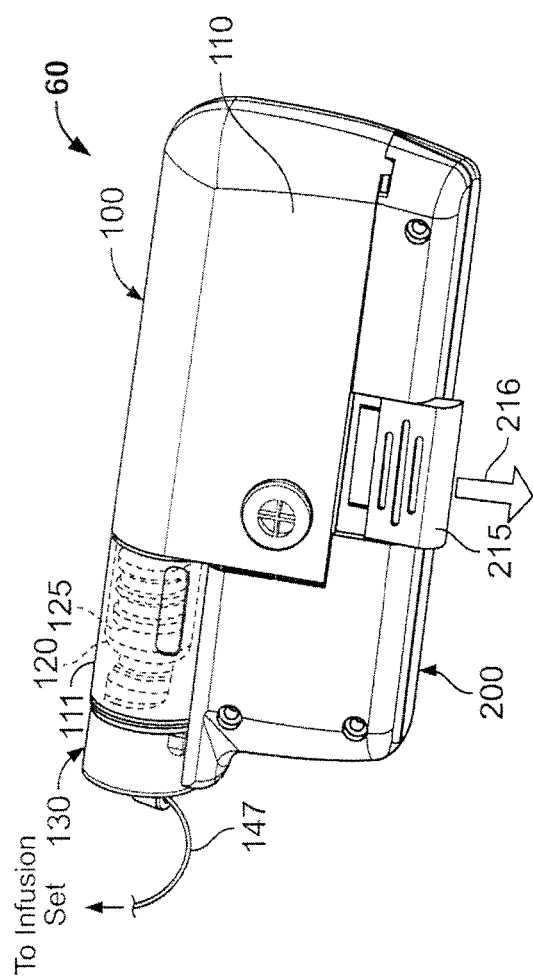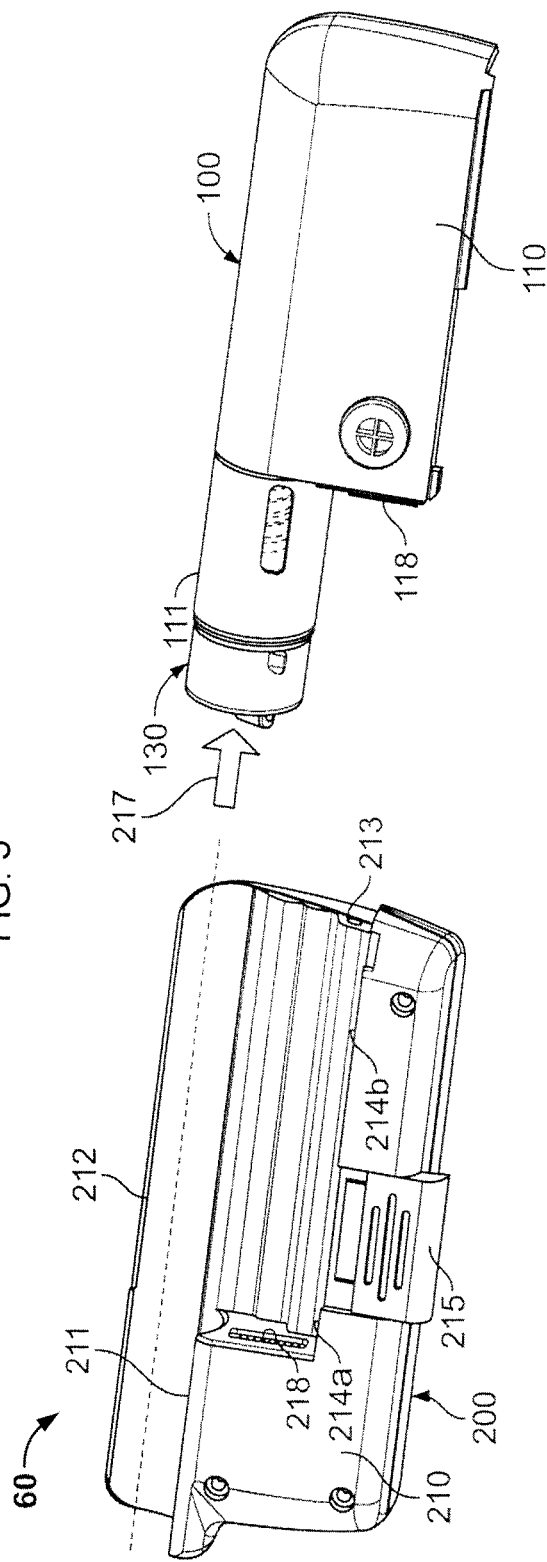

INFUSION PUMP SYSTEM AND METHODS

CROSS-REFERENCE TO RELATED APPLICATIONS

This application is a division of U.S. application Ser. No. 15/811,909, filed on Nov. 14, 2017, which is a continuation of U.S. application Ser. No. 14/804,563 filed on Jul. 21, 2015, now U.S. Pat. No. 9,844,627, which is a continuation of U.S. application Ser. No. 13/613,846 filed on Sep. 13, 2012, now U.S. Pat. No. 9,114,210, which is a continuation of U.S. application Ser. No. 12/251,629 filed on Oct. 15, 2008, now U.S. Pat. No. 8,287,487, the contents of the aforementioned applications are incorporated herein by reference in their entirety.

TECHNICAL FIELD

This disclosure relates to portable infusion pump systems to deliver fluids, such as insulin infusion pump systems or the like.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels. In some circumstances, the dosage of medicine delivered by the infusion pump acts within the patient's body over a long period of time. Such conditions, for example, may cause a patient to have an amount of non-activated insulin in his or her system even hours after the insulin dosage was dispensed from the infusion pump device.

SUMMARY

Some embodiments an infusion pump system can provide an alarm (including an alert, a safety alarm, or the like) in response to a detected condition that exceeds an alarm limit parameter. In some circumstances, the infusion pump system can determine the user's insulin load (e.g., an estimated amount of insulin already delivered to the user's body), and thereafter adjust the alarm limit parameter in response to the user's insulin load. Accordingly, the alarm limit parameters may dynamically change over time as the user's insulin load increases or decreases. Such a feature can be valuable to a user when the infusion pump is operated in conjunction with a glucose monitoring device. Moreover, the infusion pump system can be configured to provide a "missed bolus" or "missed meal" alarm in response to the user's blood glucose characteristics, the user's insulin load information, or the like.

In some embodiments, a medical infusion pump system may include a portable pump housing that receives insulin for dispensation to a user. The pump housing may at least partially contain a pump drive system to dispense the insulin through a flow path to the user. The system may also include a controller that communicates with the pump drive system to dispense the insulin from the portable pump housing, and a monitoring device that communicates glucose information to the controller. The glucose information may be indicative of a blood glucose level of the user. The controller may output an alarm when the glucose information indicates that the blood glucose level reaches beyond a glucose alarm limit parameter. The glucose alarm limit parameter may be adjustable by the controller in response to an insulin load of the user.

Particular embodiments may include a method of operating an insulin infusion pump system. The method may include receiving glucose information indicative of a glucose level of a user. The method may also include determining an insulin load of the user indicative of estimated amount of insulin delivered to the user's body. The method may further include, in response to determining the insulin load of the user, modifying at least one of an upper alarm limit parameter and a lower alarm limit parameter. The method may also include outputting an alarm when the glucose information indicates that the glucose level is greater than the modified upper alarm limit parameter or is less than the modified lower alarm limit parameter.

In some embodiments, a medical infusion pump system may include a portable pump housing that receives insulin for dispensation to a user. The pump housing may at least partially contain a pump drive system to dispense the insulin through a flow path to the user. The system may also include a controller that communicates with the pump drive system to dispense the insulin from the portable pump housing, and a monitoring device that communicates glucose information to the controller. The glucose information may be indicative of a blood glucose level of the user, and the glucose information may be stored in a computer-readable memory device over a period of time. The controller may access the glucose information stored in the memory device to detect a glucose information pattern indicative of a missed insulin bolus.

In further embodiments, a medical infusion pump system may include a portable pump housing that receives insulin for dispensation to a user. The pump housing may at least partially contain a pump drive system to dispense the insulin through a flow path to the user. The system may also include a controller that communicates with the pump drive system to dispense the insulin from the portable pump housing, and a monitoring device that communicates glucose information to the controller, the glucose information being indicative of a blood glucose level of the user. The glucose information may be stored in a computer-readable memory device over a period of time. The controller may access the glucose information stored in the memory device to detect a glucose information pattern indicative of missed food intake.

These and other embodiments described herein may provide one or more of the following advantages. First, some embodiments of the infusion pump system may reduce the likelihood of nuisance alarms to the user by automatically adjusting one or more of the alarm limit parameters in response to the user's current insulin load. For example, when an insulin infusion pump is operated in conjunction with a continuous glucose monitoring device, the insulin pump controller can be configured to provide an alarm in response to the user's blood glucose level increasing above a high glucose alarm limit (e.g., if the detected glucose level exceeds a set parameter such as 200 mg/dL). However, if the user has a high insulin load (due to a large amount of insulin already delivered to the user's body which has not yet acted), the user's blood glucose level is likely to decrease substantially over time as the non-activated insulin reaches the user's blood stream. In these circumstances, the insulin pump controller can be configured to automatically increase the high glucose alarm limit (e.g., to 210 mg/dL in one example) in order to reduce the occurrence of nuisance alarms to the user. Additional examples are described herein.

Second, some embodiments of the infusion pump controller can dynamically change a plurality of alarm limits over time as the user's insulin load increases or decreases. For example, the infusion pump controller can be configured to perform a number of operations to modify both the low glucose alarm limit and the high glucose alarm limit as the user's insulin load increases to high level. In another example, both the low glucose alarm limit and the high glucose alarm limit can be adjusted in response to the user's insulin load decreasing to a low level.

Third, particular embodiments of the infusion pump system can be configured to provide an alarm when the user's insulin load information or the user's blood glucose data indicate that a bolus dosage was missed. In some circumstances, the pump controller can receive blood glucose information from a glucose monitoring device worn by the user. The pump controller can process this blood glucose data along with insulin delivery data to determine if conditions indicate that the user skipped a bolus delivery (e.g., the user consumed a meal without activating a meal bolus or another scenario). In response to such conditions, the infusion pump controller can provide an alarm to the user indicating the missed bolus dosage and then prompt the user to take corrective actions. In some circumstances, the pump controller can employ the user's insulin load data to confirm whether conditions indicate that the user skipped a bolus delivery (and thereafter provide an alarm to the user indicating the missed bolus dosage).

Fourth, some embodiments of the infusion pump system can be configured to provide an alarm when the user's insulin load information or the user's blood glucose data indicate that a scheduled meal (or other food intake) was not consumed. For example, the pump controller may process the user's blood glucose data (e.g., received from a monitoring device worn by the user) to determine if conditions indicate that the user skipped a scheduled meal (or other food intake). In response to such conditions, the infusion pump controller can provide an alarm to the user indicating the missed meal and can prompt the user to take corrective actions. In another example, the pump controller can process the user's insulin load data to determine if conditions indicate that the user skipped a scheduled meal (or other food intake).

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5-6 are perspective views of a pump device being detached from a controller device of the system of FIG. 1, in accordance with some embodiments.

DETAILED DESCRIPTION

Figure 1:
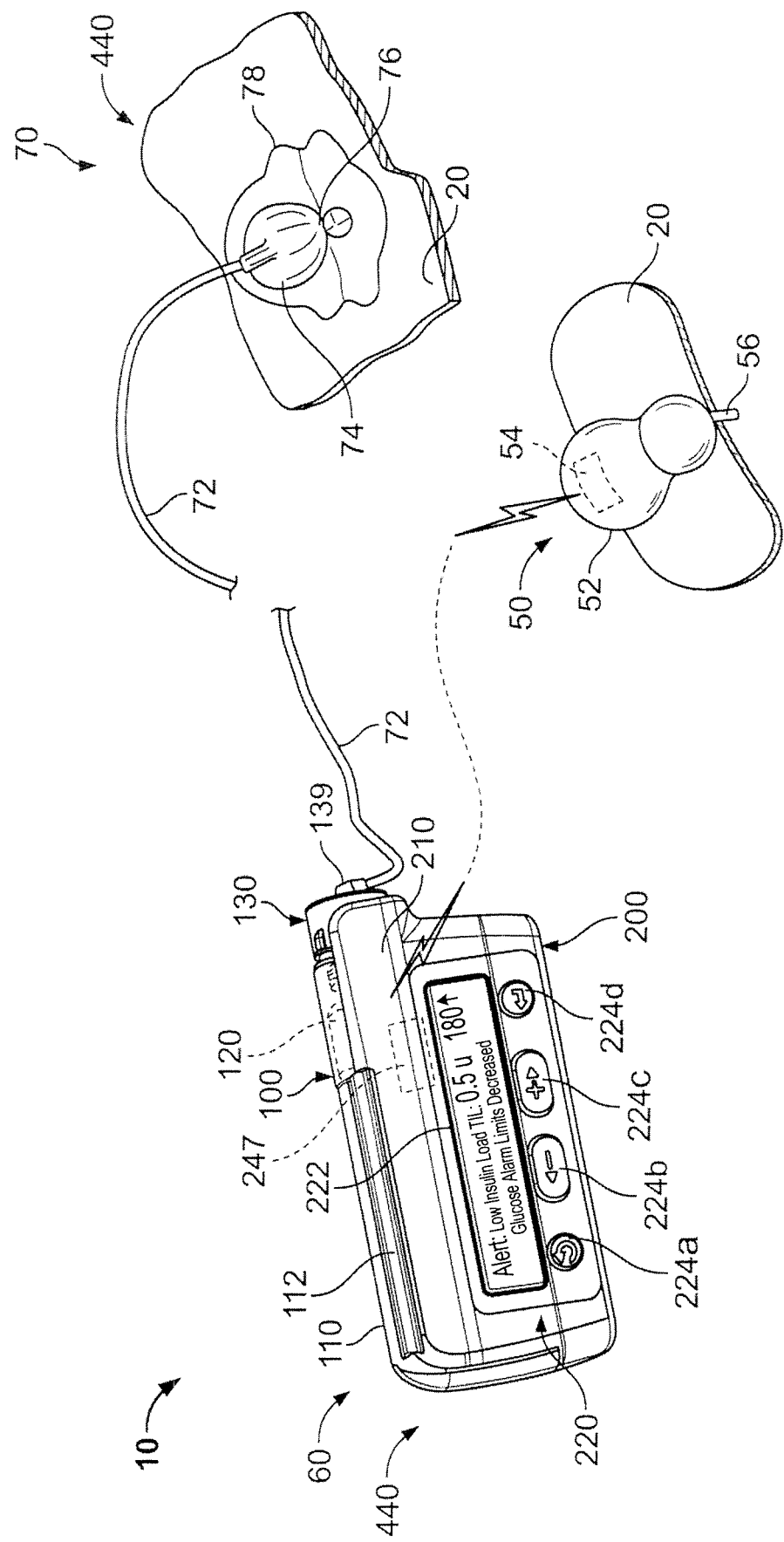
FIG. 1 is a perspective view of an infusion pump system in accordance with some embodiments.

Referring to FIG. 1, an infusion pump system 10 can include a pump assembly 60 used to supply insulin or other medication to a user via, for example, an infusion set 70. In some embodiments, a glucose monitoring device 50 can be in communication with the infusion pump assembly 60 for the purpose of supplying data indicative of a user's blood glucose level to a controller device 200 included in the pump assembly 60. The infusion pump system 10 can utilize the data indicative of a user's blood glucose level to, for example, provide an alarm (e.g., an audible or textual safety alarm, an audible or textual alert notification, or another type of alarm) when the user's blood glucose level falls below a low glucose alarm limit or rises above a high glucose alarm limit.

In some embodiments, the infusion pump system 10 can be configured to supply scheduled basal dosages of insulin (or other medication) along with user-selected bolus dosages. The basal rate can be selected to maintain a user's blood glucose level in a target range during normal activity when the user is not eating or otherwise consuming food items. The selected bolus deliveries may provide substantially larger amounts of insulin to limit the blood glucose level during certain circumstances, such as the consumption of carbohydrates and other food items. Due in part to pharmacokinetic effects (e.g., the time it takes for insulin to enter the blood stream from the subcutaneous point of delivery) and pharmacodynamic effects (e.g., the time it takes for a concentration of insulin in the blood to have the physiological effect of lower blood glucose level), basal and bolus insulin dispensed into the user's system may not act instantaneously, but instead may act over a period of time to control the user's blood glucose level. As such, the user's body may include some amount of insulin that has not yet acted even while the infusion pump assembly 60 is activated to deliver additional dosages (basal, bolus, or a combination thereof). In these circumstances, the infusion pump assembly 60 can be used to determine a user's insulin load, which can provide an estimate of the insulin which has been delivered but has not yet acted in the user's body. As described herein, the phrase "insulin load" can include an estimate previously dispensed insulin, such as the sum of recent bolus activity, and may preferably include an estimated value of previously dispensed insulin that has not yet acted in the user's body, such as total insulin load (TIL) information (a more comprehensive determination as described in more detail below), traditional insulin-on-board estimates (which typically account for only bolus dosages), or other such estimated insulin load values.

In some embodiments, the controller device 200 can determine a user's TIL information (e.g., a user's TIL value, TIL % value, or the like) in a manner that accounts for both the bolus deliveries and the basal deliveries (not merely bolus deliveries alone, as is typical with insulin-on-board estimations). As described in more detail below, this process for determining a user's TIL value can accurately reflect basal rate changes and bolus infusions. For example, in some embodiments, a user's can have different basal rates depending on the time of day (e.g., a higher basal rate during some parts of the day, a lower basal rate during the night, etc.) In further embodiments, the TIL information can be determined by the controller device 200 in a manner that also accounts for the user's previously consumed food (along with the previous basal and bolus deliveries). As described in more detail below, such a process for determining the TIL information can quantify both the previously dispensed insulin that has not yet acted on the user and the previously consumed food that has not yet been metabolized.

In some embodiments, data related to a user's insulin load, such as TIL values (or insulin-on-board estimates) and the times at which they were calculated, can be stored in a memory device (described below) of the controller device 200. This data can be used, for example, by the controller device 200 in a process to modify particular glucose alarm limits (e.g., the high glucose alarm limit, the low glucose alarm limit, or other alarm limits employed by the controller device 200). Generally, if a user's insulin load is lower than normal, the chances of the user's blood glucose level rising is more likely. In these circumstances, the controller device 200 may provide enhanced user safety by reducing the high glucose alarm limit, which can alert the user to a potentially dangerous increase in blood glucose level sooner than if the high glucose alarm limit was not modified. Alternatively, when the user's insulin load value is higher than normal or there has been recent bolus activity, the chances of the user's blood glucose level rising is less likely. In these circumstances, the controller device 200 may reduce the likelihood of nuisance alarms by raising the high glucose alarm limit or increasing the delay time between consecutive alarms, any of which can provide additional convenience to the user. In one example, a user with a default high glucose alarm limit of 200 mg/dL may have a current blood glucose level of 170 mg/dL. If that user has an insulin load (e.g., a TIL value, an IOB estimation, or the like) that is lower than a normal value or range (which may indicate the user's blood glucose level could rise in the near future, the controller device 200 may be configured to temporarily lower the high glucose alarm limit to, for example, 180 mg/dl to more quickly identify potentially unsafe rises in the user's blood glucose level.

In some embodiments, the user's blood glucose information can be used to provide alarms (including safety alarms, alert notifications, or the like) indicating an event other than "high" or "low" blood glucose levels. For example, when receiving data indicative of a user's blood glucose levels, on a periodic basis, from the monitoring device 50, the controller device 200 can be configured to provide one or more of a missed bolus alarm and a missed meal alarm (described below in connection with FIGS. 22-25). For example, the controller device 200 can determine from the stored blood glucose values that conditions indicate a user experienced a "missed bolus" situation or a "missed meal" situation. Identifying a "missed meal" and/or "missed bolus" situation can benefit the user in that this information can be used by the controller device 200 to prompt corrective action (e.g., prompting the user to eat, prompting the user for input in order to suggest a bolus dosage, or the like) before the user's blood glucose level has risen or fallen out of a normal range.

Still referring to FIG. 1, the glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to the controller device 200 of the pump assembly 60.

In some embodiments, the monitoring device 50 may include a circuit that permits sensor signals (e.g., data from the sensor shaft 56) to be communicated to the communication device 54. The communication device 54 can transfer the collected data to the infusion pump assembly 60 (e.g., by wireless communication to a communication device 247 arranged in the pump assembly 60). In some embodiments, the monitoring device 50 can employ other methods of obtaining information indicative of a user's blood characteristics and transferring that information to the infusion pump assembly 60. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the monitoring device 50 can be in communication with the pump assembly 60 via a wired connection. In other embodiments of the pump system 10, test strips (e.g., blood test strips) containing a sample of the user's blood can be inserted into a strip reader portion of the pump assembly 60 to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the pump assembly 60. In still other embodiments, characteristics of the user's blood glucose information can be entered directly into the pump system 10 via a user interface on the controller device 200.

Figure 2:
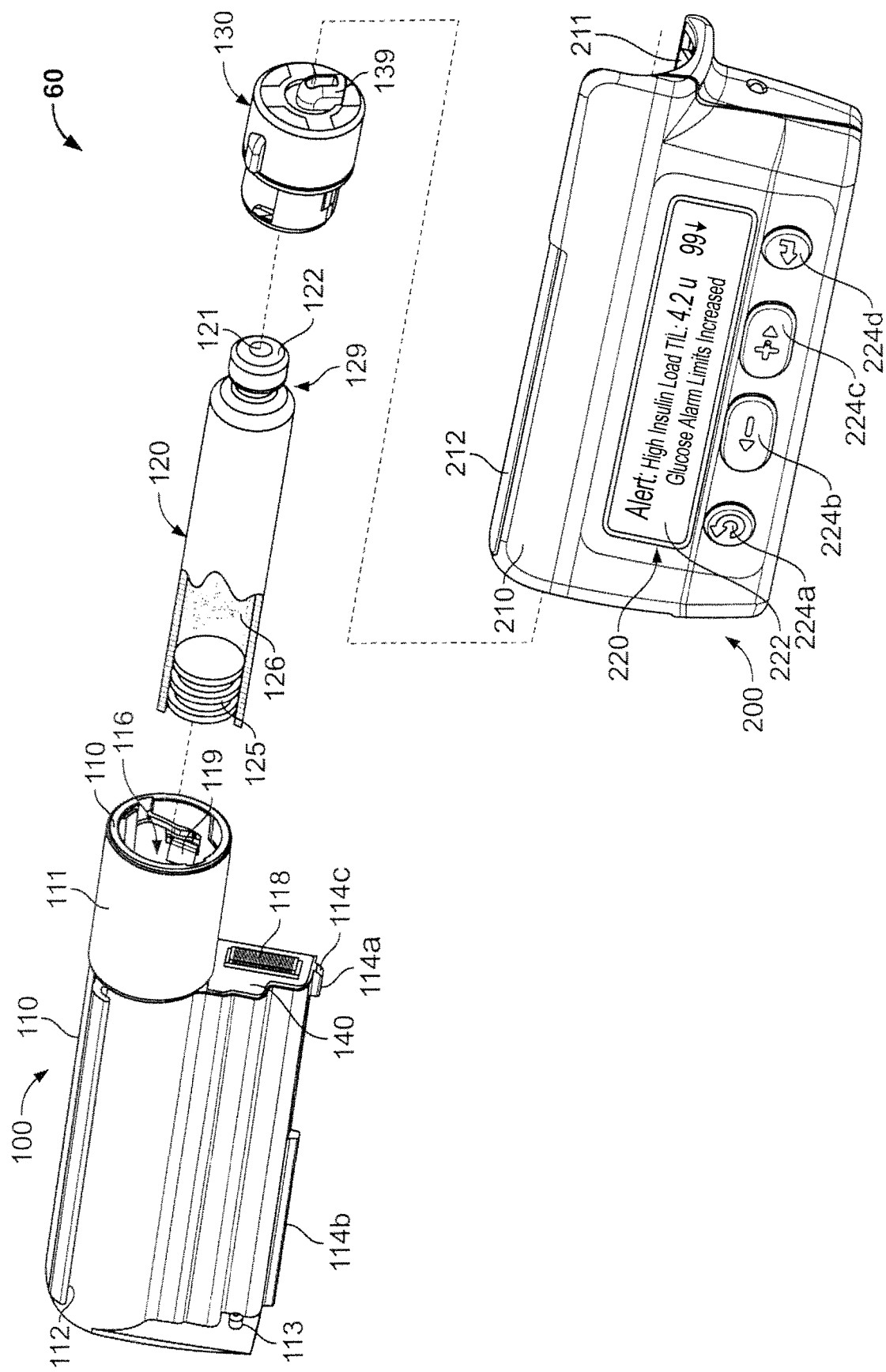
FIG. 2 is a perspective exploded view of an infusion pump assembly of the system of FIG. 1.

Referring now to FIGS. 1-2, the infusion pump assembly 60 can include a pump device 100 and the controller device 200 that communicates with the pump device 100. The pump device 100 includes a housing structure 110 that defines a cavity 116 in which a fluid cartridge 120 can be received. The pump device 100 also includes a cap device 130 to retain the fluid cartridge 120 in the cavity 116 of the housing structure 110. The pump device 100 includes a drive system (described in more detail below in connection with FIG. 10) that advances a plunger 125 in the fluid cartridge 120 so as to dispense fluid therefrom. In some embodiments, the dispensed fluid exits the fluid cartridge 120, passes through a flexible tube 72 of the infusion set 70 to a cannula housing 74. The dispensed fluid can enter through the skin via a cannula 76 attached to the underside of the cannula housing 74.

In some embodiments, the controller device 200 communicates with the pump device 100 to control the operation of the pump drive system. When the controller device 200, the pump device 100 (including the cap device 130 in this embodiment), and the fluid cartridge 120 are assembled together, the user may conveniently wear the infusion pump assembly 60 on the user's skin under clothing or in the user's pocket while receiving the fluid dispensed from the pump device 100 (refer, for example, to FIGS. 3-4). Thus, in some embodiments, the pump assembly can operate as a portable unit that provides reliable delivery of insulin or another medication in a discrete manner.

As described in more detail below, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 to the reusable controller device 200 for the dispensation of fluid from a new fluid cartridge 120. Accordingly, the user is permitted to reuse the controller device 200 (which may include complex or valuable electronics) while disposing of the relatively low-cost pump device 100 after each use. Such a pump assembly 60 can provide enhanced user safety as a new pump device 100 (and drive system therein) is employed with each new fluid cartridge 120.

Briefly, in use, the pump device 100 can be configured to removably attach to the controller device 200 in a manner that provides a secure fitting, an overall compact size, and a reliable electrical connection. The compact size permits the infusion pump assembly 60 to be discrete and portable. As described in more detail below, the controller device 200 of the infusion pump system can be used to provide glucose alarms indicative of high and low blood glucose levels (when compared to predetermined high and low blood glucose alarm levels, respectively), modify predetermined high and low blood glucose alarm levels based on insulin load information (e.g., TIL, insulin-on-board, TIL % value, and the like), and/or determine missed meal and missed bolus situations.

It should be understood that, in alternative embodiments, the pump device 100 and the controller device 200 can be configured as a single unit in which the control components and the pump drive system are arranged in a single housing. In these alternative embodiments, the pump assembly (including the controller device and the pump device) may have a different size and shape and may operate as a reusable unit that can communicate with a number of monitoring devices 50 over a period of time.

Referring again to FIGS. 1-2, in some embodiments, the pump system 10 is a medical infusion pump system that is configured to controllably dispense a medicine from the cartridge 120. As such, the fluid cartridge 120 may contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, IN Other examples of medicines contained in the fluid cartridge 120 include: medicines to treat primary immune deficiency (e.g., Vivaglobin® by CSL Behring of King of Prussia, PA), pain relief drugs, hormone therapy, blood pressure treatments, anti-emetics, osteoporosis treatments, or other injectable medicines. The medicine dispensed from the cartridge 120 into the user's system may act over a period of time in the user's body. As such, the user's body may include some amount of medicine that has not yet acted even while the infusion pump assembly 60 is activated to deliver additional dosages of the medicine (basal, bolus, or both). The infusion pump assembly 60 can be used to determine a user's total medicine load that provides an accurate indication of the medicine which has not yet acted in the user's body. The total medicine load can be determined by the controller device 200 in a manner that accounts for both the bolus deliveries and the basal deliveries of the medicine (similar to the process for determining the total insulin load as described below). It should be understood from the description herein that the fluid cartridge 120 may have a configuration other than that depicted in FIG. 2. For example, the fluid cartridge may have a different outer shape or a different reservoir volume. In another example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 may include one or more structures that interfere with the removal of the medicine cartridge 120 after the medicine cartridge 120 is inserted into the cavity 116. For example, as shown in FIG. 2, the pump housing structure 110 may include one or more retainer wings 119 that at least partially extend into the cavity 116 to engage a portion of the medicine cartridge 120 when the medicine cartridge 120 is installed therein. In this embodiment, the pump housing structure 110 includes a pair of opposing retainer wings 119 (only one is shown in the view in FIG. 2) that flex toward the inner surface of the cavity 116 during insertion of the medicine cartridge 120. After the medicine cartridge is inserted to a particular depth, the retainer wings 119 are biased to flex outward (toward the center of the cavity 116) so that the retainer wings 119 engage a neck portion 129 of the medicine cartridge 120. This engagement with the retainer wings 119 and the neck portion 129 hinder any attempts to remove the medicine cartridge 120 away from the pump device 100. Alternative embodiments can include other features and/or configurations to hinder the removal of the medicine cartridge 120.

Embodiments of the pump device 100 that hinder the removal of the medicine cartridge 120 may facilitate the "one-time-use" feature of the pump device 100. Because the retainer wings 119 can interfere with attempts to remove the medicine cartridge 120 from the pump device 100, the pump device 100 will be discarded along with the medicine cartridge 120 after the medicine cartridge 120 is emptied, expired, or otherwise exhausted. The retainer wings 119 may serve to hinder attempts to remove the exhausted medicine cartridge 120 and to insert a new medicine cartridge 120 into the previously used pump device 100. Accordingly, the pump device 100 may operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-2, the cap device 130 can be joined with the pump device 100 after the medicine cartridge is inserted in the cavity 116. It should be understood that the cap device 130 may supplement or replace the previously described retainer wings 119 by locking into position after joining with the pump housing 110, thereby hindering removal of the fluid cartridge 120 in the pump housing 110. As shown in FIGS. 1-2, the cap device 130 may include an output port 139 that connects with the tubing 72 for dispensation of the medicine to the user. In some embodiments, the output port 139 may have an angled orientation such that a portion of the tubing extends transversely to the central axis of the cartridge 120 and cap device 130. The output port 139 can be configured to mate with tubing 72 of the infusion set 70 (FIG. 1).

In some embodiments, the controller device 200 may be removably attached to the pump device 100 so that the two components are mechanically mounted to one another in a fixed relationship. Such a mechanical mounting can form an electrical connection between the removable controller device 200 and the pump device 100. For example, the controller device 200 may be in electrical communication with a portion of a drive system (described in connection with FIG. 10) of the pump device 100. As described in more detail below, the pump device 100 includes a drive system that causes controlled dispensation of the medicine or other fluid from the cartridge 120. In some embodiments, the drive system incrementally advances a piston rod longitudinally into the cartridge 120 so that the fluid is forced out of an output end 122. The septum 121 at the output end 122 of the fluid cartridge 120 can be pierced to permit fluid outflow when the cap device 130 is connected to the pump housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

The controller device 200 may be configured to removably attach to the pump device 100, for example, in a side-by-side arrangement. The compact size permits the infusion pump assembly 60 to be discrete and portable when the pump device 100 is attached with the controller device 200 (as shown in FIG. 1). In this embodiment, the controller device 200 includes a controller housing structure 210 having a number of features that are configured to mate with complementary features of the pump housing structure 110 so as to form a releasable mechanical connection (described below in more detail in connection with FIGS. 5-7). Such mating features of the pump housing structure 110 and the controller housing structure 210 can provide a secure connection when the controller device 200 is attached to the pump device 100

As shown in FIG. 2, the pump device 100 may include an electrical connector 118 (e.g., having conductive pads, pins, or the like) that are exposed to the controller device 200 and that mate with a complementary electrical connector (refer to connector 218 in FIG. 6) on the adjacent face of the controller device 200. The electrical connectors 118 and 218 provide the electrical communication between the control circuitry (refer, for example, to FIG. 9) housed in the controller device 200 and at least a portion of the drive system or other components of the pump device 100. In some exemplary embodiments, the electrical connectors 118 and 218 permit the transmission of electrical control signals to the pump device 100 and the reception of feedback signals (e.g., sensor signals) from particular components within the pump device 100. Furthermore, as described in more detail below, the infusion pump assembly 60 may include a gasket 140 that provides a seal which is resistant to migration of external contaminants when the pump device 100 is attached to the controller device 200. Thus, in some embodiments, the pump device 100 and the controller device 200 can be assembled into a water resistant configuration that protects the electrical interconnection from water migration (e.g., if the user encounters water while carrying the pump assembly 60).

Referring again to FIGS. 1-2, the controller device 200 includes the user interface 220 that permits a user to monitor the operation of the pump device 100. In some embodiments, the user interface 220 includes a display 222 and one or more user-selectable buttons (e.g., four buttons 224a, 224b, 224c, and 224d in this embodiment). The display 222 may include an active area in which numerals, text, symbols, images, or a combination thereof can be displayed (refer, for example, to FIG. 2). For example, the display 222 may be used to communicate a number of status indicators, alarms, settings, and/or menu options for the infusion pump system 10. In some embodiments, the display 222 can indicate an alarm indicative of a high or low blood glucose level, high or low insulin load, the user's current TIL information, the user's blood glucose level, an indication that the user's blood glucose level is rising or falling, an indication that a blood glucose alarm level was modified, and the like. In the example depicted in FIG. 1, the display 222 indicates that the user has a low insulin load, with a calculated TIL level of 0.5 units, and one or more glucose alarm limits have been decreased. In this embodiment, the display 222 also indicates that the user's blood glucose level is currently at 180 mg/dl and is rising.

In some embodiments, the user may press one or more of the buttons 224a, 224b, 224c, and 224d to shuffle through a number of menus or program screens that show particular status indicators, settings, and/or data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time.

The display 222 of the user interface 220 may be configured to display alarm information when no buttons 224a, 224b, 224c, and 224d have been pressed. For example, as shown in FIG. 2, the active area of the display 222 can display an alert indicating that the user's insulin load is high, the user's current TIL information (a 4.2 unit load in this example), and that the low glucose alarm level has been increased (e.g., in response to the high TIL value). The display 222 can also display the user's blood glucose level (99 mg/dl in this example) and an indication of whether the user's blood glucose level is rising or falling (the downward facing arrow indicates a falling glucose level in this example). This information can be displayed until one of the buttons 224a, 224b, 224c, and 224d has been actuated. This, or other, information can also be displayed for a period of time after no button 224a, 224b, 224c, and 224d has been actuated (e.g., five seconds, 10 seconds, 30 seconds, 1 minute, 5 minutes, or the like). Thereafter, the display 222 may enter sleep mode in which the active area is blank, thereby conserving battery power. In addition or in the alternative, the active area can display particular device settings, such as the current dispensation rate or the total medicine dispensed, for a period of time after no button 224a, 224b, 224c, or 224d has been actuated (e.g., five seconds, 10 seconds, 30 seconds, 1 minute, 5 minutes, or the like). Again, thereafter the display 222 may enter sleep mode to conserve battery power. In certain embodiments, the display 222 can dim after a first period of time in which no button 224a, 224b, 224c, or 224d has been actuated (e.g., after 15 seconds or the like), and then the display 22 can enter sleep mode and become blank after a second period of time in which no button 224a, 224b, 224c, or 224d has been actuated (e.g., after 30 seconds or the like). Thus, the dimming of the display device 222 can alert a user viewing the display device 222 when the active area 223 of the display device will soon become blank.

Accordingly, when the controller device 200 is connected to the pump device 100, the user is provided with the opportunity to readily monitor infusion pump operation by simply viewing the display 222 of the controller device 200. Such monitoring capabilities may provide comfort to a user who may have urgent questions about the current operation of the pump device 100 (e.g., the user may be unable to receive immediate answers if wearing an infusion pump device having no user interface attached thereto). Moreover, the TIL information can be displayed contemporaneously with the detected blood glucose value, so the user is provided with the opportunity to make informed decisions regarding the current and future status of his or her blood glucose level.

Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200 without the requirement of locating and operating a separate monitoring module.

In other embodiments, the user interface 200 is not limited to the display and buttons depicted in FIGS. 1-2. For example, in some embodiments, the user interface 220 may include only one button or may include a greater numbers of buttons, such as two buttons three buttons, four buttons, five buttons, or more. In another example, the user interface 220 of the controller device 200 may include a touch screen so that a user may select buttons defined by the active area of the touch screen display. Alternatively, the user interface 220 may comprise audio inputs or outputs so that a user can monitor the operation of the pump device 100.

Figure 3:
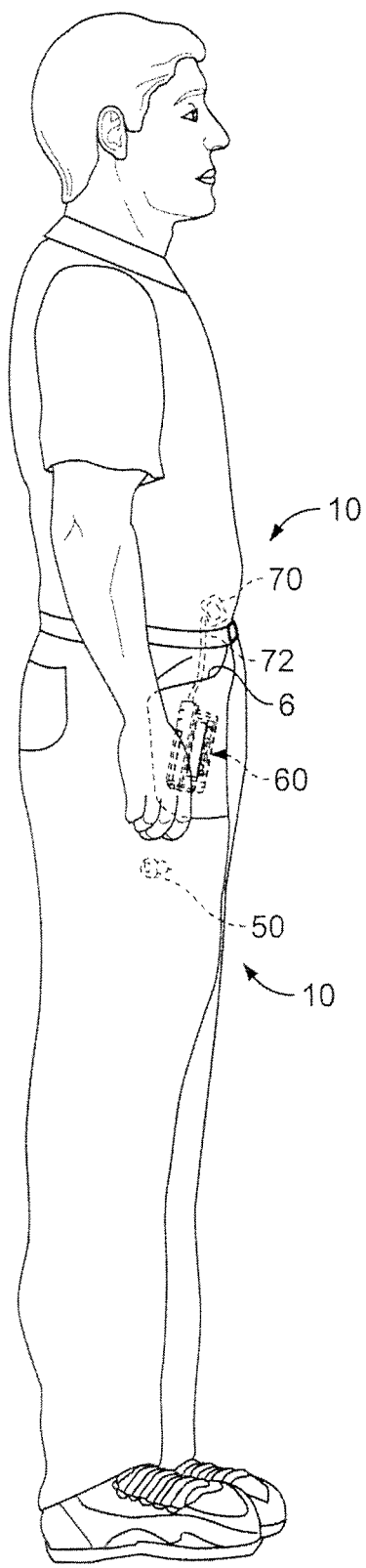
FIG. 3 is a perspective view of the infusion pump system of FIG. 1 in which the pump assembly is worn on clothing of a user, in accordance with particular embodiments.
Figure 4:
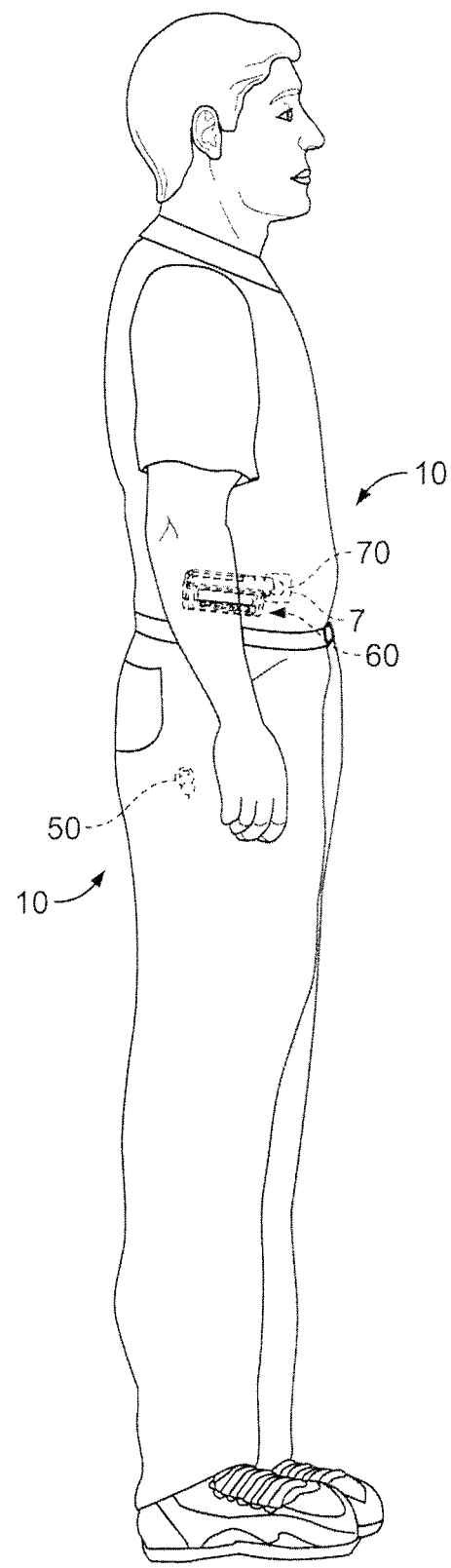
FIG. 4 is a perspective view of an infusion pump system of FIG. 1 in which the pump assembly is worn on skin of a user, in accordance with other embodiments.

Referring to FIGS. 3-4, the infusion pump system 10 may be configured to be portable and can be wearable and concealable. For example, a user can conveniently wear the infusion pump assembly 60 on the user's skin (e.g., skin adhesive) underneath the user's clothing or carry the pump assembly 60 in the user's pocket (or other portable location) while receiving the medicine dispensed from the pump device 100. The pump device 100 may be arranged in a compact manner so that the pump device 100 has a reduced length. For example, in the circumstances in which the medicine cartridge 120 has a length of about 7 cm or less, about 6 cm to about 7 cm, and about 6.4 cm in one embodiment, the overall length of the pump housing structure 110 (which contains medicine cartridge and the drive system) can be about 10 cm or less, about 7 cm to about 9 cm, and about 8.3 cm in one embodiment. In such circumstances, the controller device 200 can be figured to mate with the pump housing 110 so that, when removably attached to one another, the components define a portable infusion pump system that stores a relatively large quantity of medicine compared to the overall size of the unit. For example, in this embodiment, the infusion pump assembly 60 (including the removable controller device 200 attached to the pump device 100 having the cap 130) may have an overall length of about 11 cm or less, about 7 cm to about 10 cm, and about 9.6 cm in one embodiment; an overall height of about 6 cm or less, about 2 cm to about 5 cm, and about 4.3 cm in one embodiment; and an overall thickness of about 20 mm or less, about 8 mm to about 20 mm, and about 18.3 mm in one embodiment.

The pump system 10 is shown in FIGS. 3-4 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 may be configured to mate with the infusion set 70. In general, the infusion set 70 is tubing system that connects the infusion pump system 10 to the tissue or vasculature of the user (e.g., to deliver medicine into the user's subcutaneous tissue or vasculature). The infusion set 70 may include the flexible tube 72 that extends from the pump device 100 to the subcutaneous cannula 76 retained by a skin adhesive patch 78 that secures the subcutaneous cannula 76 to the infusion site. The skin adhesive patch 78 can retain the infusion cannula 76 in fluid communication with the tissue or vasculature of the patient so that the medicine dispensed through the tube 72 passes through the cannula 76 and into the user's body. The cap device 130 may provide fluid communication between the output end 122 (FIG. 2) of the medicine cartridge 120 and the tube 72 of the infusion set 70. For example, the tube 72 may be directly connected to the output port 139 (FIG. 2) of the cap device 130. In another example, the infusion set 70 may include a connector (e.g., a Luer connector or the like) attached to the tube 72, and the connector can then mate with the cap device 130 to provide the fluid communication to the tube 72. In these examples, the user can carry the portable infusion pump assembly 60 (e.g., in the user's pocket, connected to a belt clip, adhered to the user's skin, or the like) while the tube 72 extends to the location in which the skin is penetrated for infusion. If the user desires to monitor the operation of the pump device 100 or to adjust the settings of the infusion pump system 10, the user can readily access the user interface 220 of the controller device 200 without the need for carrying and operating a separate module.

Referring to FIG. 3, in some embodiments, the infusion pump assembly 60 is pocket-sized so that the pump device 100 and controller device 200 can be worn in the user's pocket 6 or in another portion of the user's clothing. For example, the pump device 100 and the controller device 200 can be attached together and form the assembly 60 that comfortably fits into a user's pocket 6. The user can carry the portable infusion pump assembly 60 and use the tube 72 of the infusion set 70 to direct the dispensed medicine to the desired infusion site. In some circumstances, the user may desire to wear the pump assembly 60 in a more discrete manner. Accordingly, the user may pass the tube 72 from the pocket 6, under the user's clothing, and to the infusion site where the adhesive patch 78 is positioned. As such, the pump system 10 can be used to deliver medicine to the tissues or vasculature of the user in a portable, concealable, and discrete manner. Furthermore, the monitoring device 50 can be worn on the user's skin while the pump assembly 60 is carried by the user (e.g., in a pocket). As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

Referring to FIG. 4, in other embodiments, the infusion pump assembly 60 may be configured to adhere to the user's skin 7 directly at the location in which the skin is penetrated for medicine infusion. For example, a rear surface of the pump device 100 may include a skin adhesive patch so that the pump device 100 is physically adhered to the skin of the user at a particular location. In these embodiments, the cap device 130 may have a configuration in which medicine passes directly from the cap device 130 into an infusion cannula 76 that is penetrated into the user's skin. In one example, the fluid output port 139 through the cap device 130 can include a curve or a 90° corner so that the medicine flow path extends longitudinally out of the medicine cartridge and thereafter laterally toward the patient's skin 7. Again, if the user desires to monitor the operation of the pump device 100 or to adjust the settings of the infusion pump system 10, the user can readily access the user interface 220 of the controller device 200 without the need for carrying and operating a second, separate device. For example, the user may look toward the pump device 100 to view the user interface 220 of the controller device 200 that is removably attached thereto. In another example, the user can temporarily detach the controller device 200 (while the pump device 100 remains adhered to the skin 7) so as to view and interact with the user interface 220. Furthermore, the monitoring device 50 can be worn on the user's skin while the pump assembly 60 is worn on the user's skin in a different location from that where the monitoring device is worn. As such, the monitoring device 50 can communicate information indicative of the user's blood glucose level to the pump assembly 60 while the pump assembly 60 is used to deliver medicine through the infusion set 70. In this embodiment, the monitoring device 50 may be arranged on the user's skin at a location that is spaced apart from the infusion set 70.

In the embodiments depicted in FIGS. 3-4, the monitoring device 50 adheres to the user's skin 7 at the location in which the skin is penetrated by the sensor shaft 56 (to detect blood glucose levels). The sensor shaft 56 (refer to FIG. 1) penetrates the skin surface for the purpose of exposing the tip portion of the sensor shaft 56 to the tissue or the vasculature of the user. The sensor shaft 56 can detect information indicative of the user's blood glucose level and transfer this information to a circuit that is connected to the communications device 54 located within the monitoring device 50. The communication device 54 can be in wireless communication with the communication device 247 (described in connection with FIG. 9) included in the controller device 200 of the pump assembly 60.

Referring now to FIGS. 5-8, in some embodiments, the infusion pump assembly 60 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 may be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, in some embodiments, the medicine cartridge 120 containing insulin may have an expected usage life about 7 days after the cartridge is removed from a refrigerated state and the septum 121 (FIG. 2) is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin may become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 may be designed to have an expected operational life of about 1 year to about 7 years, about 2 years to about 6 years, or about 3 years to about 5 years—depending on a number of factors including the usage conditions for the individual user. Accordingly, the user is permitted to reuse the controller device 200 (which may include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 5-6, the pump device 100 can be readily removed from the controller device 200 when the medicine cartridge 120 is exhausted. As previously described, the medicine cartridge 120 is arranged in the cavity 116 (FIG. 2) of the pump housing 110 where it is retained by the cap device 130. In some embodiments, a portion of the pump housing 110 can comprise a transparent or translucent material so that at least a portion of the medicine cartridge 120 is viewable therethrough. For example, the user may want to visually inspect the medicine cartridge when the plunger 125 is approaching the output end 122 of the medicine cartridge, thereby providing a visual indication that the medicine cartridge may be emptied in the near future. In this embodiment, the barrel 111 of the pump housing 110 comprises a generally transparent polymer material so that the user can view the medicine cartridge 120 to determine if the plunger 125 is nearing the end of its travel length.

As shown in FIG. 5, the pump device 100 has been used to a point at which the medicine cartridge 120 is exhausted. The plunger 125 has been advanced, toward the left in FIG. 5, over a period of time so that all or most of the medicine has been dispensed from the cartridge 120. In some embodiments, the controller device 200 may provide a visual or audible alert when this occurs so as to remind the user that a new medicine cartridge is needed. In addition or in the alternative, the user may visually inspect the medicine cartridge 120 through the barrel 111 of the pump housing 110 to determine if the medicine cartridge 120 is almost empty. When the user determines that a new medicine cartridge 120 should be employed, the pump device 100 can be readily separated from the controller device 200 by actuating a release member 215. In this embodiment, the release member 215 is a latch on the controller device 200 that is biased toward a locking position to engage the pump device 100. The latch may be arranged to engage one or more features on a lateral side of the pump housing 110. As such, the user may actuate the release member 215 by moving the release member 215 in a lateral direction 216 (FIG. 5) away from the pump device 100 (e.g., by applying a force with the user's finger).

As shown in FIG. 6, when the release member 215 is actuated and moved to a position away from the pump device 100, a segmented guide rail 114a-b is free to slide longitudinally in a guide channel 214a-b without interference from the release member 215. Accordingly, the user can move the pump device 100 in a longitudinal direction 217 away from the controller device 200. For example, the segmented guide rail 114a-b may slide along the guide channel 214a-b, the extension 113 (FIG. 2) may be withdrawn from the mating depression 213 (FIG. 6), and the electrical connector 118 can be separated from the mating connector 218. In these circumstances, the pump device 100 is physically and electrically disconnected from the controller device 200 while the pump device retains the exhausted medicine cartridge 120. It should be understood that, in other embodiments, other features or connector devices can be used to facilitate the side-by-side mounting arrangement. These other features or connector devices may include, for example, magnetic attachment devices, mating tongues and grooves, or the like.

In some embodiments, the gasket 140 compressed between the pump device 100 and the controller device 200 may comprise a resilient material. In such circumstances, the gasket 140 can provide a spring-action that urges the pump device 100 to shift a small amount away from the controller device 200 when the release member 215 is moved to the unlocked position (e.g., moved in the lateral direction 216 in the embodiment shown in FIG. 5). Accordingly, in some embodiments, the pump device 100 can automatically and sharply move a small distance (e.g., about 0.5 mm to about 5 mm) away from the controller device 200 when the release member 215 is moved to the unlocked position. Such an automatic separation provides a convenient start for the user to detach the pump device 100 away from the controller device 200. Furthermore, this automatic separation caused by the spring-action of the gasket 140 can provide a swift disconnect between the electrical connectors 118 and 218 when the pump device 100 is being replaced.

Figure 7:
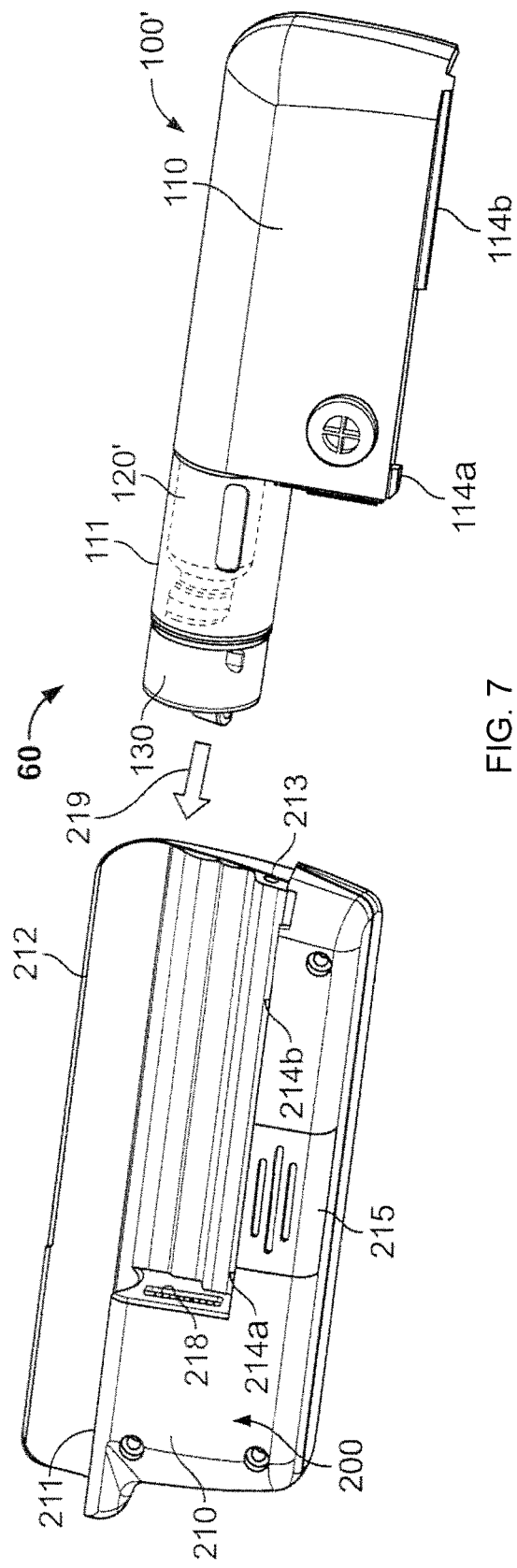
FIGS. 7-8 are perspective views of the pump device of FIGS. 5-6 being discarded and the controller device of FIGS. 5-6 being reused with a new pump device.
Figure 8:
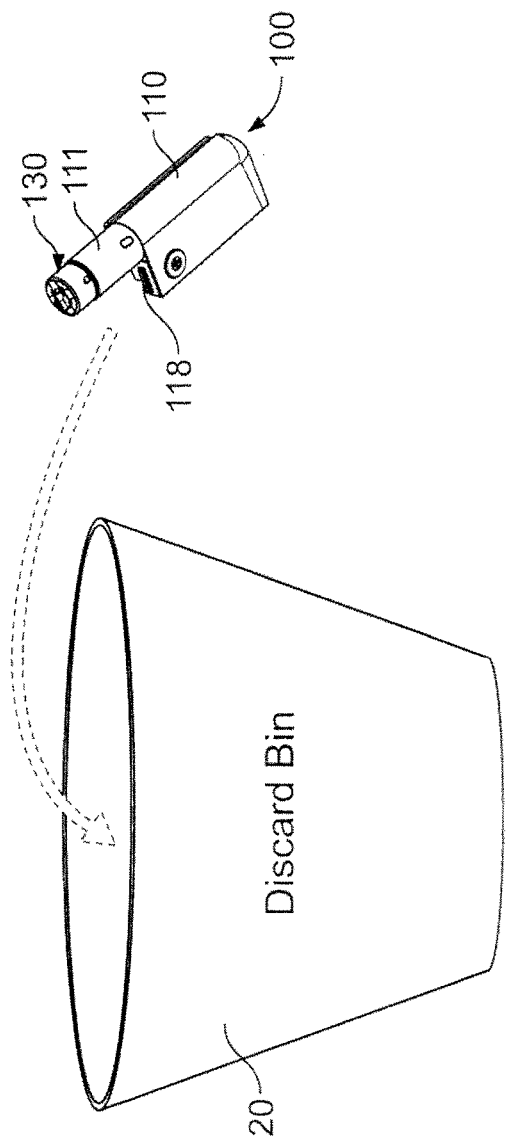

Referring to FIGS. 7-8, the same controller device 200 can be reused with a new pump device 100' having a new medicine cartridge 120' retained therein, and the previously used pump device 100 can be discarded with the exhausted medicine cartridge 120. The new pump device 100' (FIG. 7) can have a similar appearance, form factor, and operation as the previously used pump device 100 (FIGS. 5-6), and thus the new pump device 100' can be readily attached to the controller device 200 for controlled dispensation of medicine from the new medicine cartridge 120'. In some embodiments, the user may prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 2). Although the tubing 72 of the infusion set 70 is not shown in FIG. 7, it should be understood that the tubing 72 may be attached to the cap device 130 prior to the cap device 130 being joined with the housing 110. For example, a new infusion set 70 can be connected to the cap device 130 so that the tubing 72 can be primed (e.g., a selected function of the pump device 100 controlled by the controller device 200) before attaching the infusion set patch to the user's skin. As shown in FIG. 7, the new medicine cartridge 120' may be filled with medicine such that the plunger 125 is not viewable through the barrel 111. In some embodiments, the user can removably attach the pump device 100 to the controller device 200 by moving the pump device 100 in a longitudinal direction 219 toward the controller device 200 such that the segmented guide rail 114a-b engages and slides within the guide channel 214a-b. When the electrical connectors 118 and 218 mate with one another, the release member 215 can engage the segmented guide rails 114a-b to retain the pump device 100 with the controller device 200.

As shown in FIG. 8, the previously used pump device 100 that was separated from the controller device (as described in connection with FIGS. 5-6) may be discarded after a single use. In these circumstances, the pump device 100 may be configured as a disposable "one-time-use" device that is discarded by the user after the medicine cartridge 120 is emptied, is expired, has ended its useful life, or is otherwise exhausted. For example, the pump device 100 may be discarded into a bin 30, which may include a trash bin or a bin specifically designated for discarded medical products. Thus, the user is permitted to dispose of the relatively low-cost pump device 100 after each use while reusing the controller device 200 (which may include complex or valuable electronics) with subsequent new pumps 100'. Also, in some circumstances, the infusion set 70 (not shown in FIG. 8, refer to FIG. 1) that was used with the pump device 100 may be removed from the user and discarded into the bin 30 along with the pump device 100. Alternatively, the infusion set 70 can be disconnected from the previous pump device 100 and attached to the new pump device 100'. In these circumstances, the user may detach the infusion set cannula 76 and patch 78 from the skin so as to "re-prime" the tubing with medicine from the new pump device 100' to remove air pockets from the tubing. Thereafter, the infusion set cannula 76 and patch 78 can be again secured to the user's skin.

Figure 9:
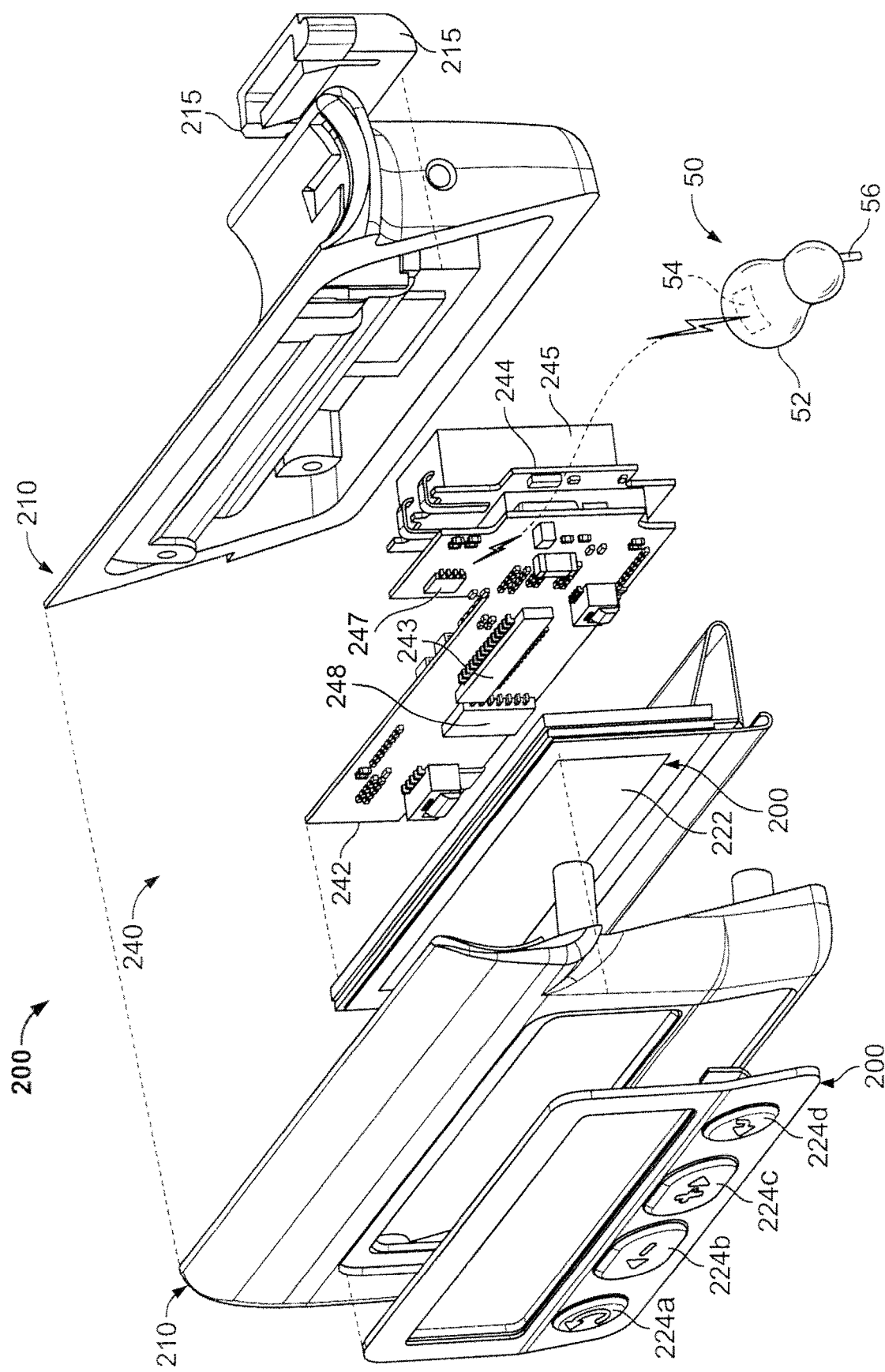
FIG. 9 is an exploded perspective view of a controller device for an infusion pump system, in accordance with some embodiments.

Referring now to FIG. 9, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices (e.g., memory chip 248). It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the one ore more memory devices, such as the memory chip 248 on the processor board 242. The control circuitry 240 may include other components, such as sensors (e.g., occlusion sensors), that are electrically connected to the main processor board 242. Furthermore, the control circuitry 240 may include one or more dedicated memory devices that store executable software instructions for the processor 243. The one or more memory devices (e.g., the memory chip 248) can also store information related to a user's blood glucose level and total insulin load (described in more detail in association with FIGS. 11-16B) over a period of time.

As previously described, the controller device 200 can be electrically connected with the pump device 100 via mating connectors 118 and 218 so that the control circuitry 240 can communicate control signals to the pump device 100 and receive feedback signals from components housed in the pump device 100. In this embodiment, the electrical connector 118 (FIG. 2) on the pump device 100 is a z-axis connector, and the connector 218 (FIG. 6) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Still referring to FIG. 9, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of status indicators, settings, and/or menu options for the infusion pump system 10. In some embodiments, the control circuitry 240 may receive the input commands from the user's button selections and thereby cause the display device 222 to output a number of status indicators (e.g., if the pump system 10 is delivering insulin, if the user's blood glucose level is rising or falling, and the like), menus, and/or program screens that show particular settings and data (e.g., the user's blood glucose level, the user's insulin load, the user's TIL % value, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port, another data cable port, or a data cable connection via the electrical connection 218) that is accessible on an external portion of the controller housing 210. As such, a cable may be connected to the control circuitry 240 to upload data or program settings to the controller circuit or to download data from the control circuitry 240. For example, historical data of blood glucose level, blood glucose alarm limits (including notification alert limits and safety alarm limits), medicine delivery (including basal and bolus deliveries), and/or TIL information can be downloaded from the control circuitry 240 (via the cable connector) to a computer system of a physician or a user for purposes of analysis and program adjustments. Optionally, the data cable may also provide recharging power.

Figure 10:
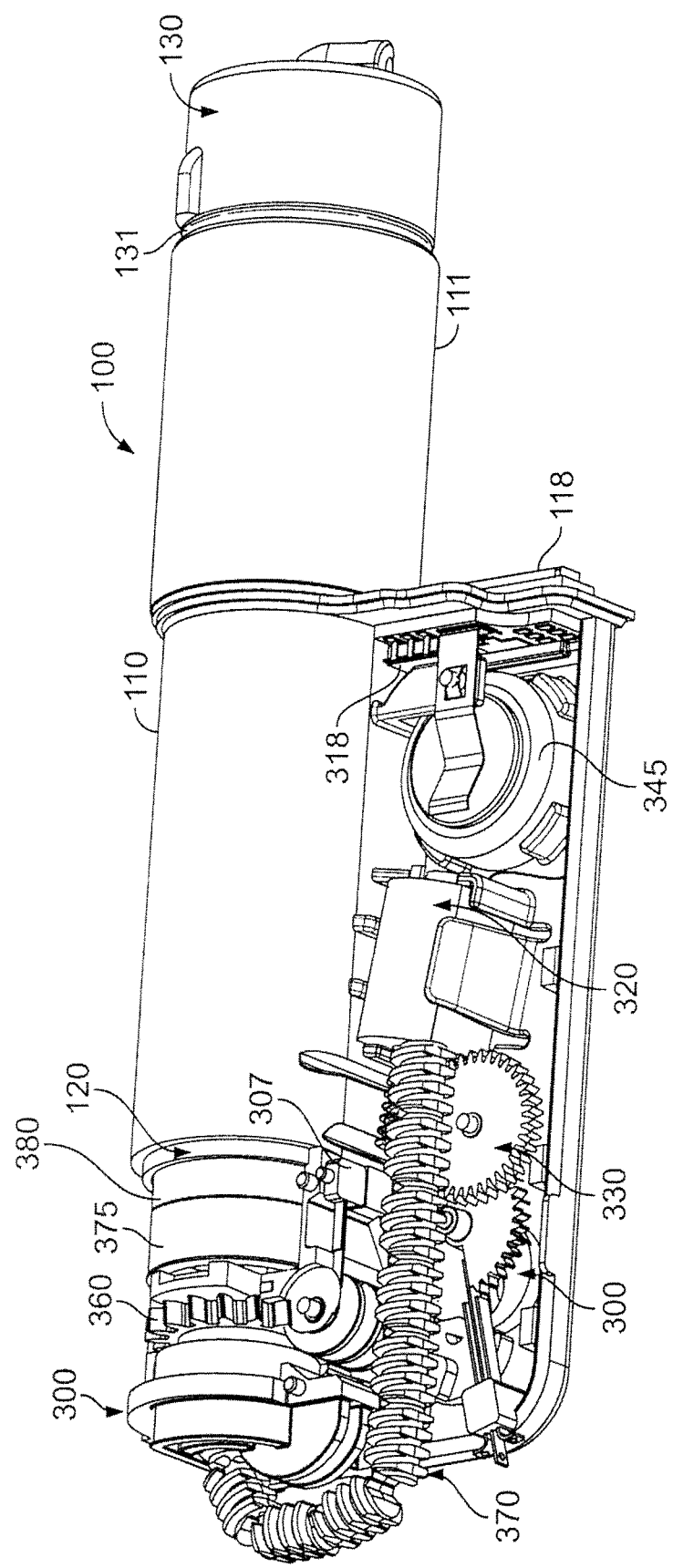
FIG. 10 is a perspective view of a portion of a pump device for an infusion pump system, in accordance with particular embodiments.

Referring to FIGS. 9-10, the control circuitry 240 of the controller device 200 may include a second power source 245 (FIG. 9) that can receive electrical energy from a first power source 345 (FIG. 10) housed in the pump device 100. In this embodiment, the second power source 245 is coupled to the power supply board 244 of the control circuitry 240. The hard-wired transmission of the electrical energy can occur through the previously described connectors 118 and 218. In such circumstances, the first power source 345 may include a high density battery that is capable of providing a relatively large amount of electrical energy for its package size, while the second power source 245 may include a high current-output battery that is capable discharging a brief current burst to power the drive system 300 of the pump device 100. Accordingly, the first battery 345 disposed in the pump device 100 can be used to deliver electrical energy over time (e.g., "trickle charge") to the second battery 245 when the controller device 200 is removably attached to the pump device 100. For example, the first battery 345 may comprise a zinc-air cell battery. The zinc-air cell battery 345 may have a large volumetric energy density compared to some other battery types. Also, the zinc-air cell battery may have a long storage life, especially in those embodiments in which the battery is sealed (e.g., by a removable seal tab or the like) during storage and before activation.

The second battery 245 may include a high current-output device that is housed inside the controller housing 210. The second battery 245 can be charged over a period of time by the first battery 345 and then intermittently deliver bursts of high-current output to the drive system 300 over a brief moment of time. For example, the second battery 245 may comprise a lithium-polymer battery. The lithium-polymer battery 245 disposed in the controller device 200 may have an initial current output that is greater than the zinc-air cell battery 345 disposed in the pump device 100, but zinc-air cell battery 345 may have an energy density that is greater than the lithium-polymer battery 245. In addition, the lithium-polymer battery 245 is readily rechargeable, which permits the zinc-air battery 345 disposed in the pump device 100 to provide electrical energy to the lithium-polymer battery 245 for purposes of recharging. In alternative embodiments, it should be understood that the second power source 245 may comprise a capacitor device capable of being recharged over time and intermittently discharging a current burst to activate the drive system 105.

Accordingly, the infusion pump system 10 having two power sources 345 and 245—one arranged in the pump device 100 and another arranged in the reusable controller device 200—permits a user to continually operate the controller device 200 without having to recharge a battery via an outlet plug-in or other power cable. Because the controller device 200 can be reusable with a number of pump devices 100 (e.g., attach the new pump device 100' after the previous pump device 100 is expended and disposed), the second power source 245 in the controller device can be recharged over a period of time each time a new pump device 100 is connected thereto. Such a configuration can be advantageous in those embodiments in which the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Referring now to FIG. 10, the pump device 100 in this embodiment includes the drive system 300 that is controlled by the removable controller device 200 (see FIG. 2). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. Some embodiments of the drive system 300 may include a battery powered actuator (e.g., reversible motor 320 or the like) that actuates a gear system 330 to reset a ratchet mechanism (e.g., including a ratchet wheel and pawl), a spring device (not shown) that provides the driving force to incrementally advance the ratchet mechanism, and a drive wheel 360 that is rotated by the ratchet mechanism to advance the flexible piston rod 370 toward the medicine cartridge 120. Connected to piston rod 370 is a pusher disc 375 for moving the plunger 125 of the medicine cartridge 120.

Some embodiments of the drive system 300 can include a pressure sensor 380 disposed between the plunger engagement device 375 and the plunger 125 for determining the pressure within the fluid path (e.g., inside the medicine cartridge 120, the infusion set 70, and the like). For example, the fluid pressure in the medicine cartridge 120 can act upon the plunger 125, which in turn can act upon the pressure sensor 380 arranged on the dry side of the plunger 125. The pressure sensor 380 may comprise a pressure transducer that is electrically connected (via one or more wires) to a gateway circuit 318 so that the sensor signals can be communicated to the controller device 200 (e.g., via the electrical connectors 118 and 218). As such, data from the pressure sensor 380 can be received by the controller device 200 for use with, for example, an occlusion detection module to determine if an occlusion exists in the medicine flow path. Alternatively, the controller device 200 may include an optical sensor system (not shown in FIGS. 9-10) to detect occlusions in the fluid path. For example, a light emitter and light sensor may each be arranged on a sensor circuit in the controller device 200 (but aligned with the pump device 100) so that the light sensor can detect the amount of light emitted by the light emitter and subsequently reflected from a component adjacent the fluid path. The reflected light level detected may be used to determine the pressure within the fluid path.

Figure 11:
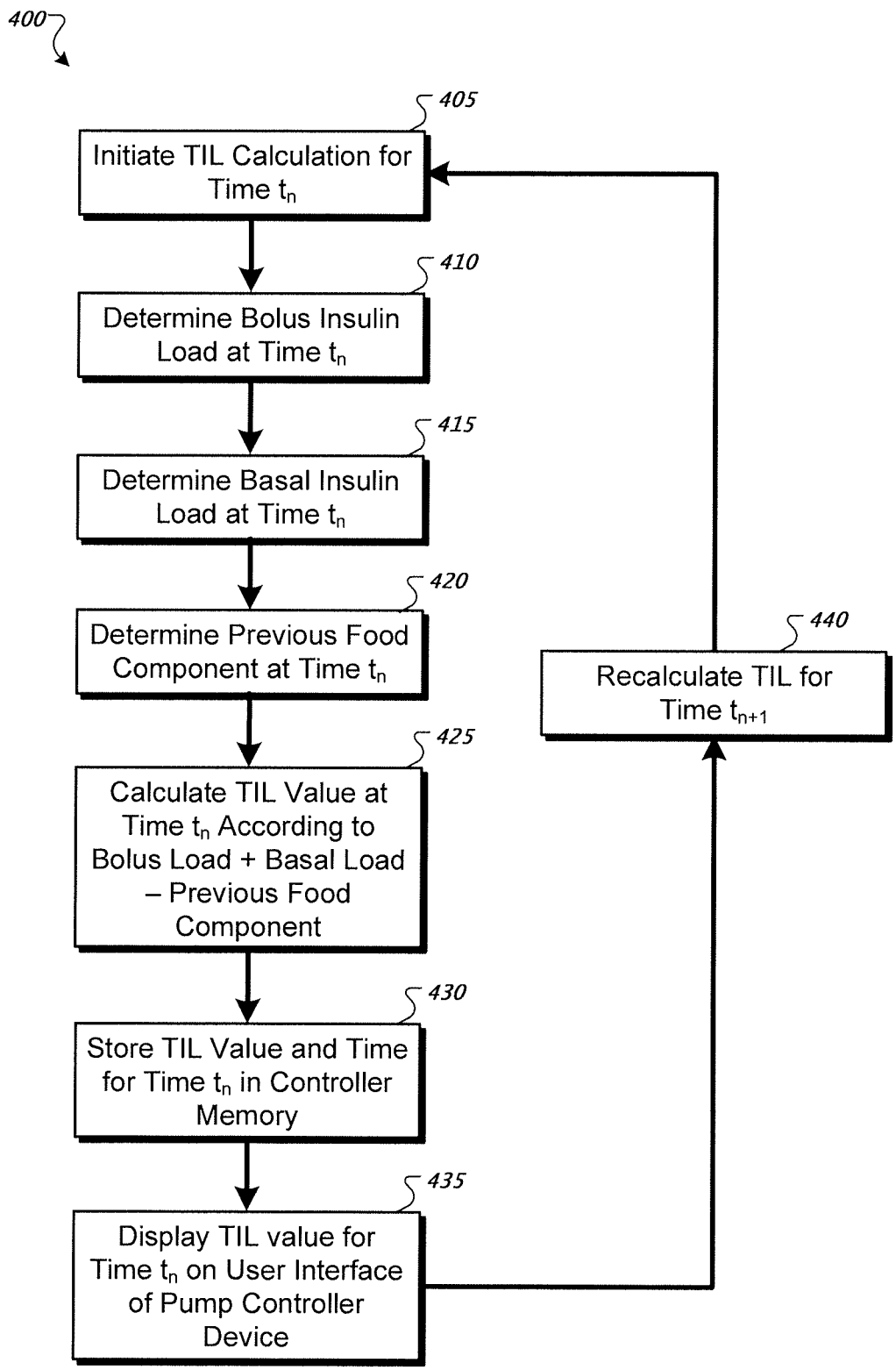
FIG. 11 is a flow diagram depicting an exemplary process used to determine a user's total insulin load (TIL), in accordance with some embodiments.

Referring now to FIG. 11, the infusion pump system 10 can be used to determine a user's TIL at a particular point in time. For example, a process 400 for determining TIL information can be implemented by the controller device 200. As previously described, the pump assembly 60 can operate to deliver insulin to the user by basal dosages, selected bolus dosages, or a combination thereof. A basal rate of insulin can be delivered in an incremental manner (e.g., dispense 0.25 U every fifteen minutes for a rate of 1.0 U per hour) to help maintain the user's blood glucose level within a targeted range during normal activity when the user is not eating or otherwise consuming food items. The user may select one or more bolus deliveries, for example, to offset the blood glucose effects caused by the intake of food or to correct for an undesirably high blood glucose level. In some circumstances, the basal rate pattern may be programmed by a health care professional during a clinical visit (or, optionally, by the user) and may remain at a substantially constant rate for a long period of time (e.g., a first basal dispensation rate for a period of hours in the morning, and a second basal dispensation rate for a period of hours in the afternoon and evening). In contrast, the bolus dosages can be dispensed in user-selected amounts based on calculations made by the controller device 200. For example, the controller device 200 can be informed of a high glucose level (e.g., by user input, data received from the glucose monitoring device 50, or the like) and can make a suggestion to the user to administer a bolus of insulin to correct for the high blood glucose reading. In another example, the user can request that the controller device 200 calculate and suggest a bolus dosage based, at least in part, on a proposed meal that the user plans to consume.

The basal and bolus insulin dispensed into the user's system may act over a period of time to control the user's blood glucose level. As such, the user's body may include some amount of insulin that has not yet acted even while the infusion pump assembly 60 is activated to deliver additional dosages (basal, bolus, or both). In these circumstances, the controller device 200 may implement a process 400 (FIG. 11) to determine the user's total insulin load (TIL), which can provide an accurate indication of the previously dispensed insulin (both basal and bolus dosages) which has not yet acted in the user's body. The TIL information can be determined in a manner that accounts for the substantial delay between the time that insulin is delivered to the tissue of the subcutaneous region and the time that this insulin reaches the blood supply. For example, the delay between a subcutaneous delivery of a bolus dosage of insulin and the peak plasma insulin level achieved from this bolus can be one hour or more. Additionally, the bolus dosage may not enter the blood stream all at once. As such, the effect of the bolus can peak at about one to two hours and then decay in a predictable manner over as much as eight hours or more (described in more detail in connection with FIG. 12). Due to the time decay effects of insulin activity, the user could be susceptible to request a subsequent bolus dosage while some insulin from a previously delivered bolus dosage has not yet acted upon the user (a scenario sometimes referred to as "bolus stacking"). To reduce the likelihood of undesirable bolus stacking, the TIL information can be determined by the controller device 200 on a periodic basis so that the user can be aware of the previously dispensed insulin which has not yet acted in the user's body. As described in more detail below (in connection with FIGS. 17-21), the TIL information can also be used to modify blood glucose alarm settings for the purpose of increasing sensitivity and/or decreasing false alarms.

For diabetics, their long term health may depend greatly on the ability to accurately control their blood glucose levels under a wide variety of conditions and to quickly and accurately predict and/or respond to changes in blood glucose level from, for example, changes in activity level, carbohydrate ingestion, missed bolus dosages, missed meals, or the like. As such, it can be beneficial for a user to employ the infusion pump system 10 that enables the user to make well-informed decisions about future insulin boluses and basal rates. For example, the controller device 200 can readily indicate to the user his or her current TIL information, which is generally more accurate than other insulin estimation tools that are based on bolus dosages alone. Also, the controller device 200 can utilize insulin load information to modify blood glucose alarm limits (including alert limits and safety alarm limits), thereby increasing the utility of said alarms by increasing sensitivity under appropriate conditions, by decreasing the occurrence of nuisance alarms, or both.

Referring in more detail to the illustrative process 400 shown in FIG. 11, the process 400 for the determining of the TIL of a user can include a number of operations performed by the controller device 200. In operation 405, the controller device 200 can initiate a TIL calculation for a particular time $t_n$ based on, for example, a request by the user (on-demand calculation) or a controller routine that determines the TIL information on a periodic basis (e.g., every 1 minute, every 2 minutes, every 5 minutes, every 10 minutes, every 30 minutes, or the like). In some embodiments, the TIL value can be calculated based on two or (optionally) three components: a bolus insulin load component, a basal insulin load component, and (optionally) a previous food component.

Figure 12:
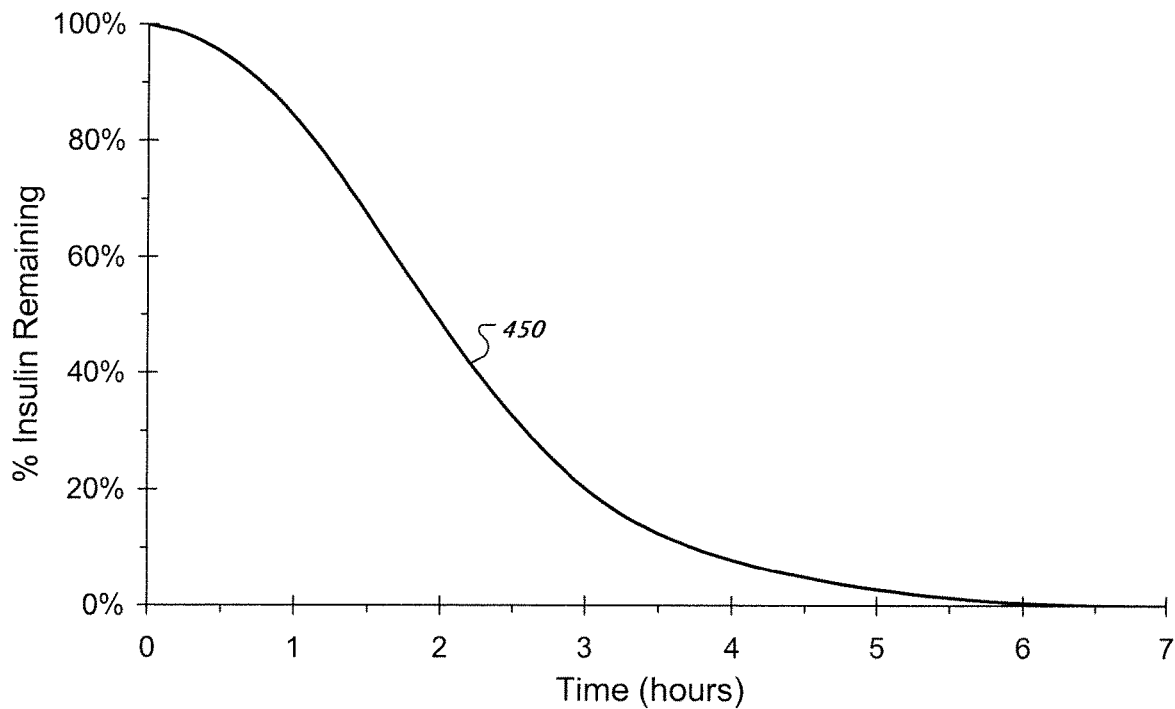
FIG. 12 is a diagram depicting an example of an insulin decay curve, which may be employed in the determination of the user's TIL in accordance with some embodiments.

In operation 410, the controller device 200 can determine the bolus insulin load at time $t_n$ based on bolus dosages that have been delivered to the patient in the recent past. In some embodiments, for each bolus dosage dispensed within a predetermined period of time before $t_n$ (e.g., 6 hours, 7 hours, 7.5 hours, 8 hours, 10 hours, or the like), the controller device 200 can estimate the amount of bolus insulin that has not yet acted in the blood stream from time-decay models generated from pharmacodynamic data of the insulin. For example, a graph of an exemplary curve depicting the percent of insulin remaining versus time can be seen in FIG. 12. In particular, FIG. 12 illustrates an example of the insulin action curve generated from pharmacodynamic data for the insulin stored in the cartridge 120. Thus, in this embodiment, the bolus insulin load component of the TIL calculation represents the sum of all recent bolus insulin dosages wherein each bolus insulin dosage is discounted by the active insulin function (which may be modeled on pharmacodynamic data as shown, for example, in FIG. 12).

Still referring to FIG. 11, in operation 415, the controller device 200 can determine the basal insulin load at time $t_n$ based on, for example, the previous basal rate during a predetermined period of time (e.g., 6 hours, 7 hours, 7.5 hours, 8 hours, 10 hours, or the like). For each basal insulin dispensation (e.g., 0.25 U dispensed every fifteen minutes, 0.5 U dispensed every fifteen minutes, 0.4 U dispensed every ten minutes, of the like), the controller device 200 can estimate the amount of basal insulin that has not yet acted in the blood stream from time-decay models generated from pharmacodynamic data of the insulin. As previously described, FIG. 12 illustrates an example of the insulin action curve generated from pharmacodynamic data for the insulin stored in the cartridge 120. Thus, in this embodiment, the basal insulin load component of the TIL calculation represents the sum of all recent basal insulin dosages wherein each basal insulin dosage is discounted by the active insulin function (which may be modeled on pharmacodynamic data as shown, for example, in FIG. 12). As described below in connection with FIG. 13, the basal insulin load at time $t_n$ may approach a constant value if the basal dosage rate remains constant over an extended period of time.

Optionally, the process 400 may include operation 420 in which the previous food component is employed in the TIL calculation. The controller device 200 can determine the previous food component based on, for example, the total carbohydrates previously entered into the controller device 200 as being consumed by the user during a predetermined period of time before $t_n$ (e.g., 6 hours, 7 hours, 7.5 hours, 8 hours, 10 hours, or the like). The previous food component can be determined, for example, by estimating the amount of carbohydrates that have been consumed but not yet metabolized by the user's body so as to effect the blood glucose level. For each of the previous food items reported by the user, the controller device 200 can estimate the previously consumed food that has not yet been metabolized from a time-based model generated from a standard glycemic index. Alternatively, when the user enters information regarding food intake, the user can be prompted to identify the metabolization "speed" of the food item based on the glycemic index for that food. In these circumstances, the user may be prompted to input the amount of food (e.g., grams of Carbohydrate or another representative value) and then identify the glycemic index (via a numerical scale or from a list of two or more choices (e.g., "fast" metabolization and "slow" metabolization) to provide a more accurate time-based function for specific meals. When this yet-to-be-metabolized carbohydrate value is estimated, it can be treated as a "negative" insulin component in the TIL calculation by multiplying the yet-to-be-metabolized carbohydrate value by a carbohydrate ratio (e.g., 1 unit of insulin per 15 grams of carbohydrates). In some embodiments, the calculated value for the previous food component can be displayed separately to the user (e.g., to provide the user with information regarding the effects of the previously consumed carbohydrates).

Still referring to FIG. 11, in operation 425, the TIL at time $t_n$ can be calculated by summing the bolus insulin load, the basal insulin load, and (in some embodiments) the previously consumed food component, where the previous food component is treated as a negative insulin unit value. In these circumstances, the TIL values may accurately reflect both the previously dispensed insulin that has not yet acted (to reduce or otherwise effect the blood glucose level) and the previously consumed food that has not yet been metabolized (to increase or otherwise effect the blood glucose level). It should be understood from the description herein that, in alternative embodiments, the process for determining the TIL information may not include the previous food component (as described in connection with operation 420). In such embodiments, the TIL at time $t_n$ can be calculated by summing both the bolus insulin load and the basal insulin load. Because this TIL determination is not based merely on previous bolus deliveries, the TIL information may accurately reflect basal rate changes and the impact of stopping insulin delivery or changing basal delivery for a short period of time (e.g., a temporary basal rate change).

In operation 430, the TIL value can be stored in the memory of the controller device 200 (e.g., in the memory chip 248 or in another memory device coupled to the control circuitry 240). For example, the calculated TIL value at time $t_n$ can be stored in a database along with the time $t_n$. The database may also store the current blood glucose level at time $t_n$, which may be generated from the sensor signal received from the monitoring device 50 (FIG. 1). As described in more detail below, the database can maintain a historical record of the TIL information, the time information, and (optionally) the detected blood glucose information that is accessible by the controller device 200 or by an external computer.

In operation 435, the TIL information can be displayed on the user interface 220 of the pump controller device 200. The TIL information can be retrieved from the memory device that stores the recently calculated TIL value. In particular embodiments, the display 222 of the user interface 220 may be configured to display an alarm information screen in response to an abnormal condition (e.g., a high blood glucose level). In the example depicted in FIG. 1, the display 222 can indicate an alert (a low insulin load in this example), the recently determined TIL information (0.5 U insulin load in this example), the user's current blood glucose level (180 mg/dl in this example), an indication of whether the user's blood glucose level is rising or falling (the upward facing arrow indicates an increasing glucose level in this example), and an indication that one or more glucose alarm limits have been modified (one or more alarm limits have been decreased in this example). In another example, as shown in FIG. 2, the display 222 of the user interface 220 provides an alarm information screen that indicates an alert (high insulin load in this example), the recently calculated TIL information (a 4.2 U load in this example), the user's blood glucose level (99 mg/dl in this example), an indication of whether the user's blood glucose level is rising or falling (the downward facing arrow indicates a falling glucose level in this example), and an indication that one or more glucose alarm limits have been modified (one or more alarm limits have been increased in this example).

In operation 440, the process 400 can return to initiate a new TIL calculation after a period of time. For example, the operation 440 can cause the controller device 200 to calculate the TIL for time $t_{n+1}$ by returning to operation 405. As previously described, the controller device 200 can initiate the subsequent TIL calculation for the subsequent time $t_{n+1}$ based on a request from the user or based on a program that causes calculation of the TIL information on a periodic basis (e.g., every 1 minute, every 2 minutes, every 5 minutes, every 10 minutes, every 30 minutes, or the like). The subsequent TIL value for time $t_{n+1}$ can be stored in the memory of the controller device 200 (e.g., in the previously described database) and can be displayed on the user interface 220 of the controller device 200.

Referring now to FIG. 12, in some embodiments, the controller device 200 can calculate the TIL information using, at least in part, time-based models derived from pharmacodynamic data. As previously described, the TIL value of a user can include a bolus insulin load component and a basal insulin load component, each of which may be determined using a time-decay model generated from pharmacodynamic data associated with the insulin stored in the cartridge 120. As shown by way of example in FIG. 12, the controller device 200 can utilize a time-decay curve (represented by curve 450), which is generated from pharmacodynamic data, to estimate the percentage of insulin remaining in a user's body after a particular period of time.

Figure 13:
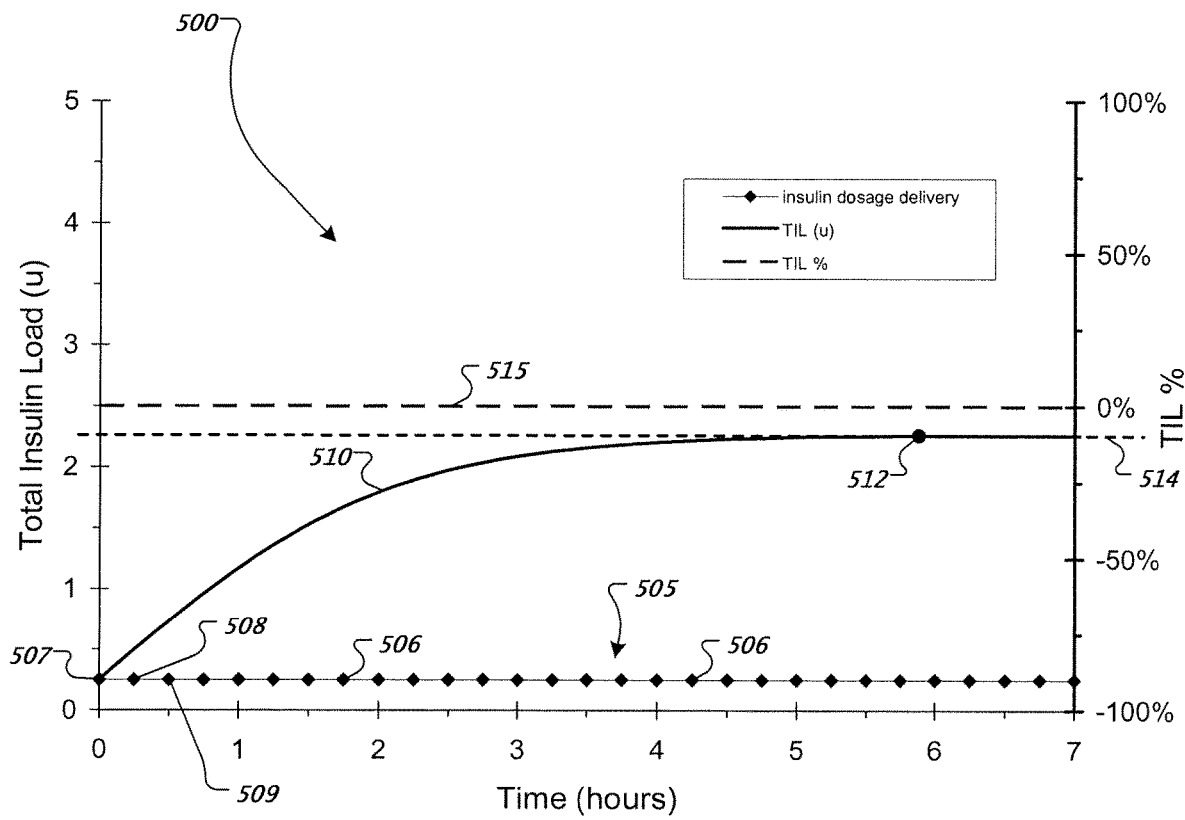
FIG. 13 is a diagram depicting an example of an insulin delivery pattern (constant basal delivery rate only) and a user's corresponding TIL and TIL % values, in accordance with some embodiments.

Referring now to FIG. 13, graph 500 is an exemplary depiction of how a constant basal delivery can affect a user's TIL information. In this example, the basal insulin deliveries are represented as a series of basal infusion points 506 (e.g., dosages of 0.25 U every fifteen minutes to provide a basal rate of 1.0 U per hour). It should be understood from the description herein that, while the basal rate is sometimes described as a generally continuous administration, it can be implemented a series of small injections given at regular intervals. Because the basal rate is constant over a period of seven hours with no bolus dosages, the insulin delivery pattern 505 is represented as a horizontal, straight line that depicts a constant basal rate of 1.0 units/hour. For the purposes of this example, it is presumed that there were no basal or bolus insulin deliveries prior to time=0 (hours), there were no previously consumed carbohydrates acting on the user's total insulin load, and that the user's TIL (represented by TIL curve 510) was also 0.0 prior to time=0. This may occur, for example, after the user wakes in the morning and then activates the pump assembly 60 to deliver the basal insulin. As such, the user's TIL value has only a single component (basal insulin load) and is equal to zero before time=0. The other components of the TIL calculation, such as the bolus insulin load and the previous food component, are zero in this example. At time=0 the first basal infusion (represented by point 507) of 0.25 units is made. Since substantially none of the insulin delivered in the first infusion (point 507) has acted on the user at time=0, the entire contents of the infusion (0.25 units) are now part of the TIL, which is reflected in the TIL curve 510. With the subsequent boluses 508 and 509, the TIL increases, while some small portion of the previously dispensed insulin acts in the blood stream. This is estimated from a time-decay curve (refer, for example, to FIG. 12), which is generated from pharmacodynamic data. As time increases, however, the amount of insulin leaving the insulin load and entering the blood stream increases until point 512 where the amount of insulin leaving the insulin load to act in the blood stream is substantially equal to the amount of insulin entering the insulin load due to the constant basal infusion. If the basal rate remains constant, than the TIL will continue to remain at the equilibrium value shown on the graph 500. In this example, the TIL reaches equilibrium at a value of about 2.25 U (as shown on the left-side axis in graph 500).

In some circumstances, the TIL information can be stored, displayed, or both as a normalized value (e.g., the TIL % value indicated on the right-side axis of the graph 500). Although the TIL value (in units of insulin) is a useful number, that actual value can vary from user to user depending on his or her insulin intake characteristics. The TIL % value can be used as one feature to normalize the TIL calculation for convenient analysis or comparison between users. For example, the TIL % value can be calculated as follows:

$$\text{TIL \% value} = [(\text{Actual TIL}) - (\text{theoretical TIL}_{basal})] / (\text{theoretical TIL}_{basal}) \times 100,$$

where theoretical $\text{TIL}_{basal}$ represents the TIL that would have been generated based only on the user's basal insulin dosages (e.g., presuming no bolus insulin and no previous food components)

As such, in the example depicted in FIG. 13, the TIL % value remains at a constant of 0% (refer to TIL % curve 515) because the actual TIL value remains equal to the theoretical $\text{TIL}_{basal}$ value (based only on the user's basal insulin dosages). However, when the user receives bolus dosages and/or or has a previous food component (such circumstances are described in more detail below), the TIL % value may provide for prompt analysis of the user's insulin status and provide for easy comparison between users.

The controller device 200 can display the TIL information on the user interface 220 as the TIL value (in units of insulin as shown, for example, in FIG. 1), as the TIL % value (normalized to be a percentage as shown, for example, in FIG. 2), or as both the TIL value and the TIL % value. Moreover, the TIL information can be stored in a memory device (e.g., memory device 248) of the controller device 200 as the TIL value (in units of insulin), as the TIL % value (normalized to be a percentage), or as both the TIL value and the TIL % value.

Figure 14:
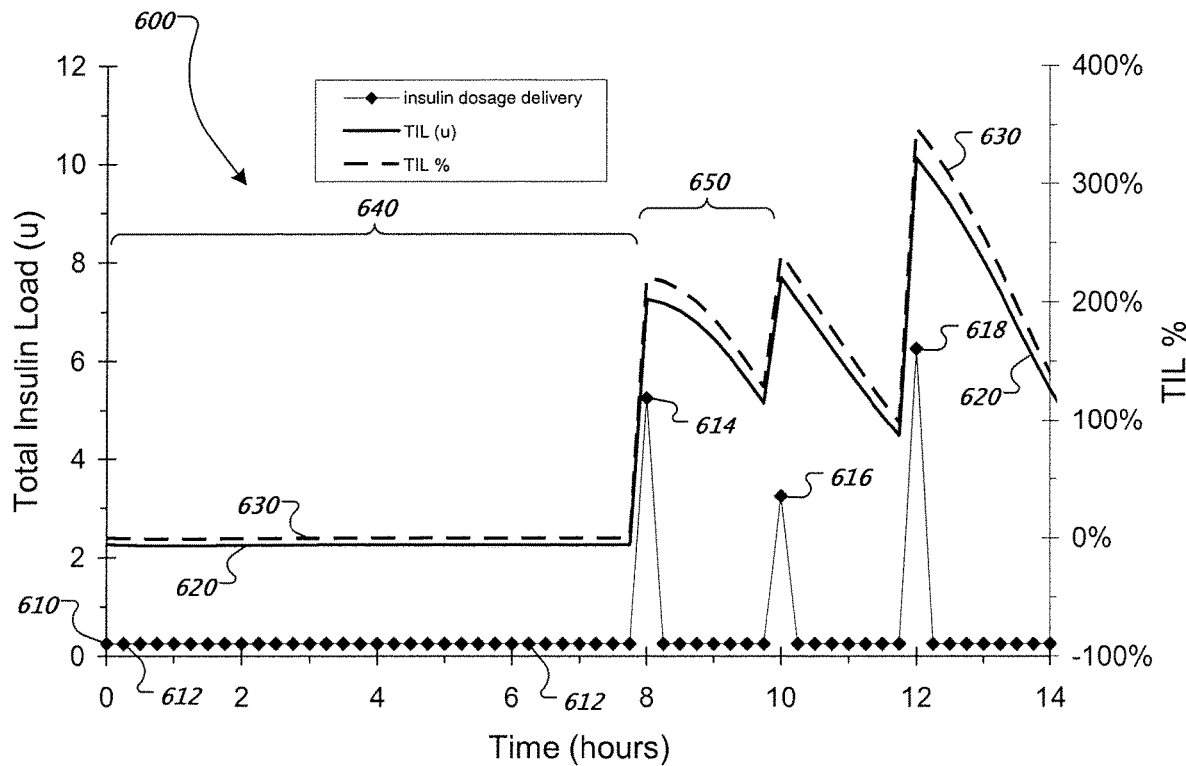
FIG. 14 is a diagram depicting an example of an insulin delivery pattern (constant basal delivery rate plus selected bolus deliveries) and a user's corresponding TIL and TIL % values, in accordance with some embodiments.

Referring now to FIG. 14, the controller device 200 can calculate the TIL information based, at least in part, on both basal insulin dispensations and bolus insulin dispensations. In this example, graph 600 includes an insulin delivery curve 610 made up of individual basal dispensations 612 and bolus dispensations 614, 616, and 618, a TIL curve 620 (which accounts for both a basal load component and a bolus load component), and a TIL % curve 630. In region 640, the basal infusion rate remains constant and no boluses are infused, so the TIL curve 620 remains at it's equilibrium value while the TIL % curve 630 remains at 0% (similar to the characteristics described in connection with FIG. 13). At about time=8 hours, a bolus delivery 614 of about 5 insulin units is delivered to the user. This bolus dosage may be selected in response to the user proposing new food intake, the user attempting to offset an elevated blood glucose level that requires correction, or the like. This bolus delivery 614 raises the user's TIL value to slightly higher than 7 units, or about 5 units plus the equilibrium value. In region 650, the user's TIL value decays or otherwise decreases as the previously dispensed insulin transitions to act in the user's blood stream (e.g., to lower or otherwise affect the user's blood glucose level). With the subsequent boluses 616 and 618, at about time=10 and time=12 hours respectively, the user's TIL value increases with each bolus, and thereafter decays.

As shown in FIG. 14, the TIL % value is also affected by the bolus deliveries 614, 616, and 618. For example, the TIL % curve 630 indicates that the TIL % value increases from 0% to about 222% immediately after the first bolus delivery 614. Although the TIL value (in units of insulin, represented in curve 620) is a useful number, that value may vary from user to user depending on his or her insulin intake characteristics (e.g., type of insulin, insulin sensitivity, carbohydrate ratio, overall insulin requirements, or the like). Here, the TIL % value of about 222% represents a normalized value for convenient analysis by the user or a health care provider. In particular, this normalized value indicates to the user that the TIL is more than two times (e.g., 222%) what it would ordinarily be if the user had maintained just the constant basal rate (from region 640) without any bolus delivery 614). In region 650, the user's TIL % value decays or otherwise decreases as the previously dispensed insulin transitions to act in the user's blood stream (e.g., to lower or otherwise affect the user's blood glucose level). With the subsequent boluses 616 and 618, at about time=10 and time=12 hours respectively, the user's TIL % value increases with each bolus, and thereafter decays.

Figure 15:
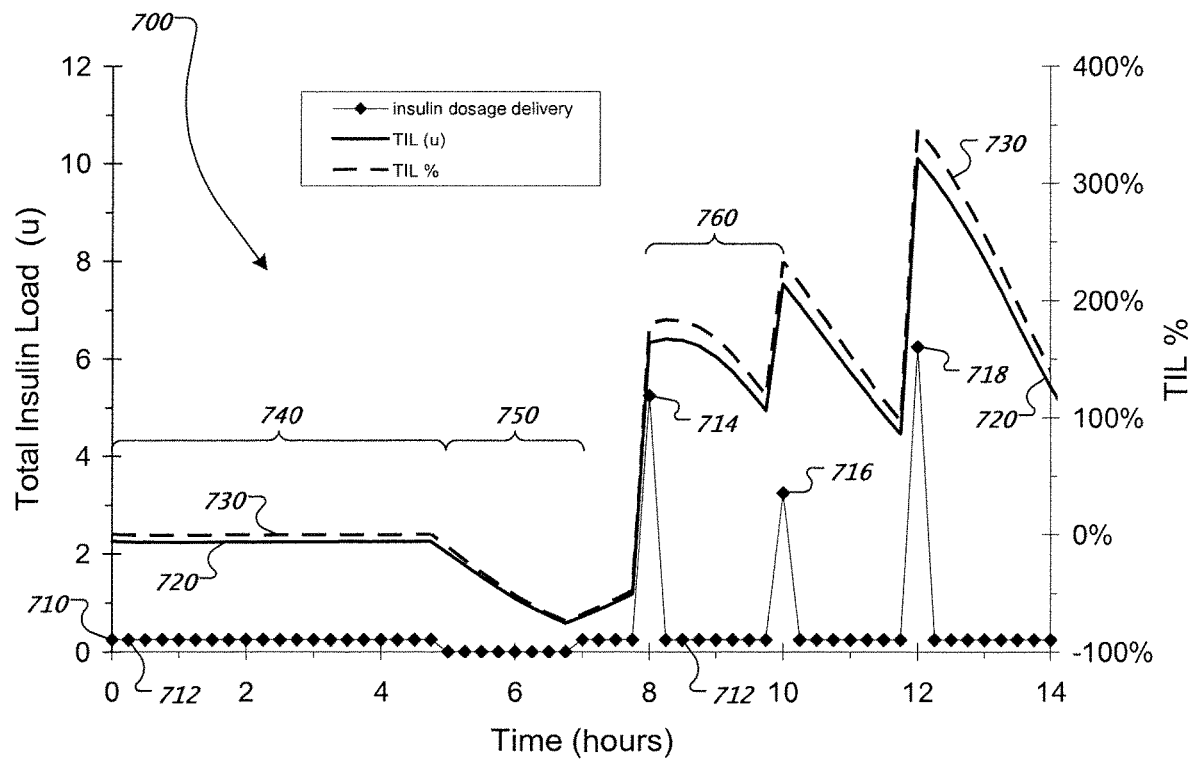
FIG. 15 is a diagram depicting an example of an insulin delivery pattern (intermittent basal delivery plus selected bolus deliveries) and corresponding TIL and TIL %, in accordance with some embodiments.

Referring now to FIG. 15, as previously described, the TIL information can be determined in a manner that accounts for both the bolus deliveries and the basal deliveries (not merely previous bolus deliveries). As such, the TIL values may accurately reflect basal rate changes and the impact of stopping insulin delivery (e.g., during periods in which insulin delivery is stopped or basal delivery is altered, during activities such as swimming or another exercise, etc.). The insulin delivery pattern in FIG. 15 is similar to the previously described scenario shown in FIG. 14, except that the basal delivery is stopped between time=5 hours and time=7 hours (refer to the basal delivery curve 710 in graph 700). For example, the graph 700 includes a region 740, in which the basal infusion rate remains constant and no boluses are infused, so the TIL curve 720 approaches a constant value while the TIL % curve 730 remains at 0% (similar to the previously described scenario shown in FIG. 14). At about time=5 hours, basal delivery is suspended for a period of approximately two hours (refer to region 750). As a result, the TIL curve 720 decays or otherwise reduces in that period of time because the previously dispensed insulin transitions to act in the user's blood stream (e.g., to lower or otherwise affect the user's blood glucose level) and no further insulin is being dispensed during that time period. Also, in the example depicted in FIG. 15, the TIL % curve 730 transitions into negative values (e.g., −25%, −50%, etc.) because the insulin dosages were ceased between time=5 hours and time=7 hours. During such periods of ceased insulin delivery, the actual TIL value may become less than theoretical $\text{TIL}_{basal}$ (e.g., the TIL that would have been generated based on the user's basal insulin dosages), which causes the TIL % values to transition into negative values. In one example, the user may readily recognize that his or her insulin load (e.g., TIL %=−25%) is approximately ¼th less than what it normally would have been if he or she had maintained the scheduled basal insulin delivery rate. Accordingly, the TIL values and the TIL % values can accurately reflect basal rate changes and the impact of stopping insulin delivery.

As shown in FIG. 15, the basal insulin rate restarts at about time=7 hours, which causes the TIL value to increase and the TIL % value to return toward 0%. In this example, a bolus delivery 714 of about 5 units is delivered to the user at about time=8 hours, thereby raising the user's TIL value about 5 units to slightly higher than 6 units. Such a bolus delivery 714 also causes the TIL % value to increase to slightly less than 200% in this example. This normalized value indicates to the user that the TIL is slightly less than two times what it would ordinarily be if the user had maintained just the constant basal rate (from region 740) without any bolus delivery 714. In region 760, the user's TIL value and the TIL % value decays or otherwise decreases as the previously dispensed insulin transitions to act in the user's blood stream (e.g., to lower or otherwise affect the user's blood glucose level). With subsequent bolus deliveries 716 and 718 at about time=10 and time=12 hours respectively, the user's TIL value and the TIL % value increases with each bolus, and thereafter decays.

Figure 16A:
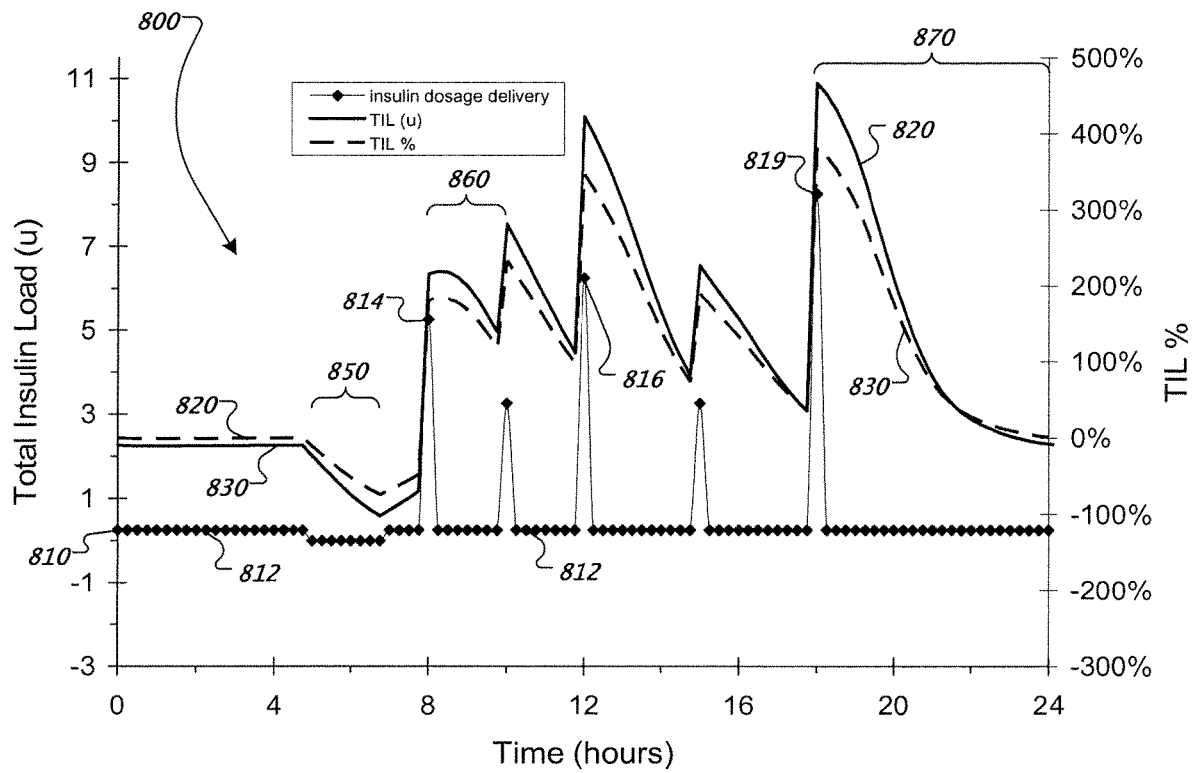
FIG. 16A is a diagram depicting an example of an insulin delivery pattern (intermittent basal delivery plus selected bolus deliveries) and a user's corresponding TIL and TIL % values, in accordance with some embodiments.

Referring now to FIG. 16A, the TIL value may return to a constant value (and the TIL % value may return to 0%) after an extended period of time with no bolus activity. For example, the graph 800 in FIG. 16A is similar to the previously described graph in FIG. 15, except that it shows the insulin delivery pattern over a greater duration of time. In some embodiments, a user may continue to receive insulin deliveries from the pump assembly 60 during his or her period of sleep. The user can receive only his or her ordinary basal dosages during this period of sleep so as to maintain his or her blood glucose level within a safe range. In the example depicted in FIG. 16A, the user receives a bolus delivery 819 before a dinner meal at about time=18 hours. Thereafter, no further bolus dosages are provided for the remainder of the day, and the user receives only the ordinary basal rate delivery (refer to region 870 in FIG. 16A). During this extended period of receiving only the basal deliveries as shown in region 870, the TIL values (refer to TIL curve 820) decay or otherwise decrease from a value greater than 10 units of insulin to a constant value of slightly greater than 2 units. Also, during this extended period in region 870, the TIL % values (refer to TIL % curve 830) decay or otherwise decrease from a normalized value of almost 400% to the constant value of 0%. Accordingly, over a period of a day or more, the TIL value and the TIL % value can "reset" or otherwise return to a constant value during periods of sleep (when the user receives nighttime basal dosages) or during other extended periods during which no bolus activity occurs.

In the previous examples, described in connection with FIGS. 14-16A, the controller device 200 calculated the TIL at any given time by summing the insulin load due to basal delivery and the insulin load due to one or more bolus deliveries (if any). These examples depict embodiments of the controller device 200 that provide the advantage of using more accurate insulin action curves to estimate the amount of insulin that has been delivered to a user (but not yet acted in that user's blood stream), and the advantage of including a basal insulin load component to the TIL calculation (thus incorporating all delivered insulin in the TIL calculation). As described previously, a calculated TIL value can be used to, for example, predict future blood glucose levels and/or can be used in the calculation of suggested bolus amounts. As such, the controller device 200 can employ the TIL information to provide accurate information to the user and to avoid "bolus stacking" and unsafe swings in blood glucose level.

In much the same way that insulin does not immediately enter the blood stream and act upon a user after subcutaneous delivery, ingested carbohydrates can also take time to fully act upon the user's blood glucose level. In some embodiments, the controller device 200 can also include a component in the TIL calculation that takes into account food which has been previously consumed but not yet acted in the user.

Figure 16B:
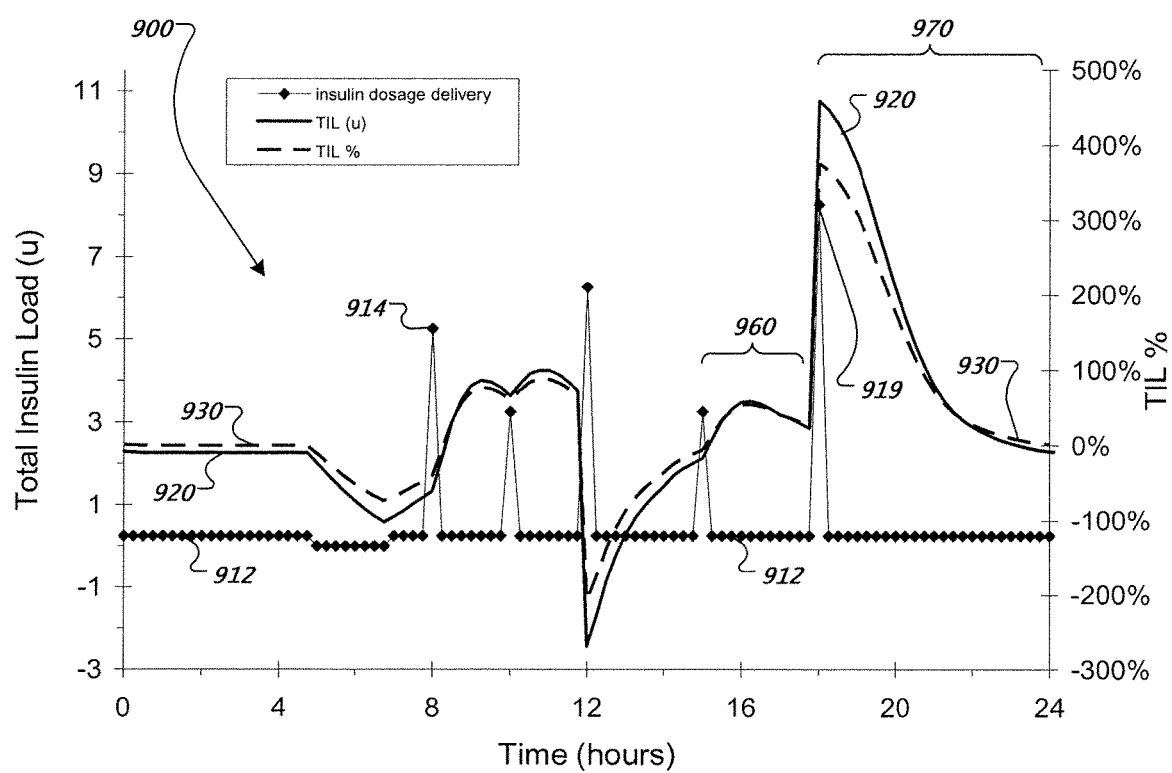
FIG. 16B is a diagram depicting an example of insulin delivery pattern (intermittent basal delivery plus selected bolus deliveries) and a user's corresponding TIL and TIL % values that account for a previously consumed food component, in accordance with some embodiments.

Referring now to FIG. 16B, as previously described, the TIL information can account for the user's previously consumed food in addition to the bolus deliveries and the basal deliveries. In these circumstances, the TIL values may accurately reflect both the previously dispensed insulin that has not yet acted and the previously consumed food that has not yet been metabolized. The insulin delivery pattern in FIG. 16B is similar to the previously described scenario shown in FIG. 16A, except that the user in FIG. 16B skips a bolus delivery at time=12 hours (note that FIG. 16A shows a bolus delivery 816 at time=12 hours). Also, in the example depicted in FIG. 16, the TIL calculation process also accounts for previously consumed food (e.g., the previous food component). For example, the graph 900 in FIG. 16B includes a basal delivery curve 910 made up of individual basal infusions 912, a TIL curve 920, and a TIL % curve 930. At about time=12 hours, the user enters meal data into the controller device 200, but no bolus delivery is dispensed (e.g., due to user error or another reason), leading to an immediate drop in the TIL curve 920 and the TIL % curve 930. This substantial decrease in the TIL value and the TIL % value is due to the fact that the process for calculating the TIL information accounts for the user's previously consumed food intake (in addition to the bolus deliveries and the basal deliveries). Thus, the controller device 200 receives information at time=12 hours that the user has consumed food but no bolus delivery was provided (e.g., a missed bolus situation). As such, the previous food component of the TIL calculation becomes much more significant than the bolus load component and the basal load component (thereby driving the TIL value and the TIL % value into the negative value range). In some embodiments, this drop of the TIL curve 920 into the negative region could result in the controller device 200 alerting the user to a potentially unsafe condition (e.g., a pending significant rise in blood glucose level) long before the user's blood glucose level begins to rise outside of a targeted range. Such a safety feature can provide enhanced protection for the user, who would have the opportunity to select a correction bolus before the blood glucose level increased to unsafe conditions.

Still referring to FIG. 16B, at about time=18 hours, a bolus delivery 915 is provided to the user, but no meal data is entered into the controller device 200. Unlike the previous situation at time=12 hours in which the user missed a bolus dosage, this situation arises at time=18 hours when the user misses a meal. This situation may occur, for example, where the user schedules a bolus dosage in anticipation of a future meal, but then forgets or fails to consume the proposed meal. Such conditions can lead to a sharp increase in the TIL curve 920 and the TIL % curve 930. As such, the bolus load component of the TIL calculation becomes much more significant than the previous food component (thereby driving the TIL value and the TIL % value upward into the higher value range). In some embodiments, this sharp increase of the TIL curve 920 could result in the controller device 200 alerting the user to a potentially unsafe condition (e.g., a pending significant drop in blood glucose level) long before the user's blood glucose level begins to fall outside of a targeted range. Such a safety feature can provide enhanced protection for the user, who would have the opportunity to consume food items and enter the food data in the controller device 300 before the glucose level decreased to unsafe conditions. If the user did consume food at about time=18 hours but merely forgot to enter the information into the controller device 200, the user would have the opportunity to enter the meal information, thus causing the next TIL calculation to be corrected. For example, in response to the alert from the controller device 200, the controller device may prompt the user to enter the previous food information (if he or she forgot to enter the meal information) or to start the consumption of food items.

Similar to embodiments previously described in connection with FIG. 16A, the TIL value may return to a constant value (and the TIL % value may return to 0%) after an extended period of time with no bolus activity and no food consumption activity. In this example shown in FIG. 16B, during the period between time=18 hours and time=24 hours, the user may cease bolus activity and food consumption (e.g., as he or she prepares for sleep and begins to sleep overnight). During this extended period of receiving only the basal deliveries as shown in region 970, the TIL values (refer to TIL curve 920) decay or otherwise decrease to a constant value of slightly greater than 2 units. Also, during this extended period in region 970, the TIL % value (refer to TIL % curve 930) decay or otherwise decrease to a constant value of 0%.

In some embodiments, the controller device 200 can use data indicative of the user's blood glucose level (e.g., information received from the monitoring device 50, user input, glucose test strips inserted into the controller device 200, or the like) to alert the user of potentially unsafe glucose levels. For example, in response to a user's recent blood glucose data that is indicative of a high blood glucose level, the controller device 200 may alert the user to the high blood glucose level, request input from the user, suggest a bolus dosage, or any combination thereof. Alternatively, In response to data indicative of a low blood glucose level, the controller device 200 may alert the user, request input from the user, suggest a meal to be consumed, or any combination thereof. In some embodiments, a fixed high and low glucose alarm limits can be preset (e.g., by a health care provider) and compared to the user's blood glucose level to determine if the current blood glucose level is outside of a normal range. In other embodiments, the parameters defining a normal range can be dynamically adjusted to benefit the user, using data such as the user's current insulin load.

In some embodiments, after receiving a bolus dosage of insulin (e.g., in response to a high blood glucose level), there can be a delay between the time that a user receives the bolus dosage and the time that a substantial portion of that bolus acts on the user. During this time period, the user's blood glucose level can remain high, or continue to increase. Similarly, after consuming a meal (e.g., in response to a low blood glucose level), there can be a delay between the time that the user consumes food and food is able to act on the user (e.g., raise the user's blood glucose level). Due in part to these delays, in can be can be beneficial for a user to employ an infusion pump system that can identify information indicative of future unsafe blood glucose levels and can suggest corrective actions (e.g., receive a bolus dosage, consume carbohydrates, or the like) based on this information, thereby minimizing, or eliminating, the amount of time that a user experiences unsafe or undesirable blood glucose levels. The previously described delays in insulin and food action can also cause a user to be alerted to a condition (e.g., high blood glucose level, low blood glucose level, or the like) that has been previously corrected for (e.g., by the user receiving a bolus, the user consuming carbohydrates, or the like), but where the corrective action has not yet acted on the user. For example, if a user consumes a high carbohydrate meal and waits for a period of time (e.g., 45 minutes) before receiving a bolus, the carbohydrates could later have the affect of raising the blood glucose level of the user before the insulin takes affect. In examples such as this, the user's blood glucose level can temporarily rise above an upper blood glucose alarm limit and later, without additional correction, fall below that upper alarm limit into a normal range, when the insulin load (e.g., the previously received bolus) acts on the user. In some embodiments, giving an alarm given when the blood glucose level rises above an upper glucose limit, but subsequently falls below this limit without corrective action, may be considered as a nuisance alarm by the user. In some circumstances, it can be beneficial for the user to employ an infusion pump system that can identify information indicative of nuisance alarms and use this information to modify alarm parameters (e.g., upper and lower alarm limits) to lower the likelihood, or eliminate the occurrence, of these nuisance alarms.

Figure 17:
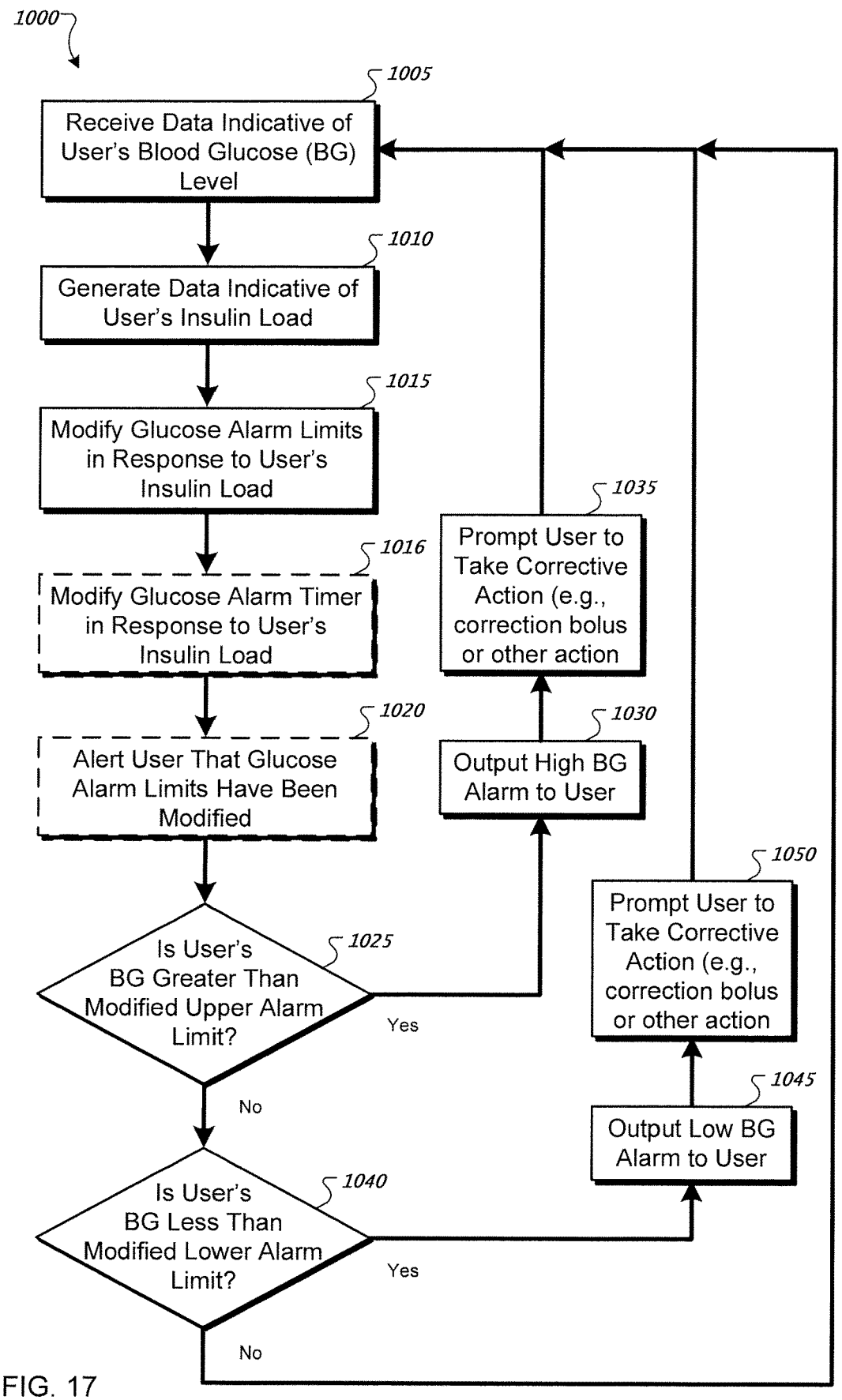
FIG. 17 is a flow diagram depicting an exemplary process used to determine, and alert a user of, high or low blood glucose levels, in response to TIL information, in some embodiments.

Referring now to FIG. 17, the infusion pump system 10 can be configured to determine the user's insulin load (e.g., an estimated amount of insulin already delivered to the user's body), and thereafter adjust the alarm limit parameter in response to the user's insulin load. Accordingly, the glucose alarm limit parameters may be dynamically modified over time as the user's insulin load increases or decreases. In some embodiments, the controller device 200 can be used to dynamically modify parameters associated with a user's blood glucose alarm range (e.g., modify the upper alarm limit, modify the lower alarm limit, or both) based at least in part, on the user's insulin load. For example, a process 1000 for dynamically modifying glucose alarm parameters, based at least in part on the user's insulin load, can be implemented by the controller device 200. As previously described, the controller device 200 can receive data indicative of blood glucose information from, for example, the glucose monitoring device 50. The controller device 200 can compare the data and/or the information derived from the data to upper and lower glucose alarm limits for the purpose of determining if the user's blood glucose level is outside of a normal range. In particular embodiments, the default upper and lower glucose alarm limits may be programmed by a health care professional during a clinical visit (or, optionally, by the user) and may remain at these programmed values for a long period of time (e.g., until the next clinical visit, until the user gets a new controller device 200, or the like). In some circumstances, it may be beneficial to the user for the controller device 200 to dynamically change glucose alarm parameters by, for example, calculating modified upper and/or lower glucose alarm limits and subsequently comparing the user's current blood glucose level to the modified limits.

Referring in more detail to the illustrative process 1000 shown in FIG. 17, the process 1000 for calculating modified upper and lower glucose alarm limits and determining if a user's blood glucose level is outside of a modified normal range (e.g., has risen above the modified upper glucose alarm limit, fallen below the modified lower glucose alarm limit, or the like) can include a number of operations performed by the controller device 200. In operation 1005, the controller device 200 can receive data indicative of a user's blood glucose level. For example, the controller device 200 can receive data, via wired or wireless communication, from the glucose monitoring device 50. In other examples, the controller device 200 can access previously stored blood glucose data from memory (such as the memory chip 248). In still other examples, a user can insert a glucose testing strip into a strip reader portion of the pump assembly 60, or enter information directly into the user interface 220.

In operation 1010, the controller device 200 can generate data indicative of the user's insulin load. As described previously, the phrase "insulin load" can include an estimate previously dispensed insulin, such as a sum of recent bolus activity, and may preferably include an estimated value of previously dispensed insulin that has not yet acted in the user's body, such as total insulin load (TIL) information (a more comprehensive determination as described in more detail below), traditional insulin-on-board estimates (which typically account for only bolus dosages), or other such estimated insulin load values. For example, as described previously in connection with FIG. 11, the controller device 200 can calculate the user's TIL value or the user's insulin-on-board estimate to generate the insulin load data. It should be understood that this type of insulin load data can be generated when it is retrieved from memory (e.g., the memory chip 248). In another example, the insulin load data may be indicative of the sum of the recent bolus activity (e.g., all bolus dosages within the recent one hour, two hours, or the like), and the controller device 200 can retrieve the recent bolus dosage values from the memory chip 248. The insulin load data generated in operation 1010 can be used by the controller device 200 in operation 1015 to modify the default upper and lower glucose alarm limits, which may be set by a health care professional during a clinic visit, by the user, or a combination thereof. Exemplary processes used to modify the default alarm limits are described in more detail in connection with FIGS. 18-21. In one example, the controller device 200 can determine if the user's insulin load is within a normal range. If so, the controller device 200 can leave the alarm limits unmodified or return modified values that are identical to the preset values. If the user's insulin load is outside of the normal range, the controller device 200 can modify one or more of the glucose alarm limits by, for example, multiplying them by a scaling factor that can be based, at least in part, on the value of the user's insulin load (described in more detail in connection with FIGS. 20-21). In another example, if the user's insulin load is outside of the normal range, the controller device 200 can modify one or more of the glucose alarm limits by a predetermined function such as step function in which the alarm limits are increased or decreased by a preset value (e.g., increase or decrease the upper and lower alarm limits by 50 mg/dL). In further examples, the controller device 200 can modify the glucose alarm limits using one or more equations that include insulin load values (e.g., the user's TIL value, the user's TIL % value, the user's IOB value, the sum of the recent bolus activity, or the like). Exemplary processes to modify the alarm limits using equations that include insulin load values are described in connection with FIGS. 18-19.

Some embodiments may include operation 1016, in which the controller modifies the alarm timer in response to the user's insulin load. For example, the high blood glucose alarm may include a timer that causes the alarm to be repeated to the user at a timer interval (e.g., every 30 seconds, every minute, every two minutes, every five minutes, or the like). Thus, the user may be provided with the option to "snooze" the high blood glucose alarm while he or she is taking actions to resolve the alarm circumstances. This "snooze" timer can be modified to reduce the occurrences of repeated nuisance alarms or to increase the occurrence of serious safety alarms. In one example, the controller device 200 can determine if the user's insulin load is within a normal range. If so, the controller device 200 can leave the alarm timer unmodified or return modified values that are identical to the preset values. If the user's insulin load is outside of the normal range, the controller device 200 can modify the alarm timer, for example, by multiplying the default timer value by a scaling factor (e.g., reducing the timer value by half, by increasing the timer value by two, or the like). For instance, in circumstances in the controller device receives information indicative of a high blood glucose value but also determines that the insulin load is also a high value (e.g., the user recently received a bolus), the controller 200 can modify the alarm timer by increasing the default timer value by two (e.g., from two minutes to four minutes). As such, the controller device 200 may alert the user that the blood glucose level is high, but then the controller device 200 may delay repeating that alarm to reduce nuisance alarms as the insulin begins to act in the user's body. It should be understood that this operation 1016 may be performed in addition to operation 1015 or as an alternative to operation 1016. Thus, in some embodiments, the controller device can modify the glucose alarm limits in response to the user's insulin load (operation 1015), modify the alarm timer in response to the user's insulin load (operation 1016), or modify both the glucose alarm limits and the alarm timer (operations 1015 and 1016).

Referring to operation 1020 in FIG. 17, in some embodiments, it may be helpful to the user for the controller device 200 to alert the user that the glucose alarm limits have been modified. Exemplary alerts are depicted on the display 222 of the controller 200 in FIGS. 1 and 2. In operation 1020, the controller device 200 can optionally alert the user that the glucose alarm limits have been modified. In one example, the controller device 200 may notify the user whenever a glucose alarm limit is modified. In another example, the controller device 200 may only notify the user that a glucose alarm limit has been modified when a high or low glucose alarm is communicated to the user. In still another example, the controller device 200 may notify the user that a glucose alarm limit has been modified only when the modification meets certain criteria (e.g., the glucose alarm limit has been modified by more than 10 percent, more then 15%, more than 10 units, or the like).

In operation 1025, the controller device 200 can compare the user's current (or most recent) blood glucose level (e.g., received in operation 1005) to the modified upper glucose alarm limit (e.g., determined in operation 1015). If the user's blood glucose level is greater than the modified upper glucose alarm limit, the controller device 200 can perform operation 1030 and communicate to the user a high blood glucose alarm (e.g., an audible alarm or alert, text on a display 222 describing an alarm or alert, a vibratory alarm or alert, another communicative output, or a combination thereof). In operation 1035, the controller device 200 can prompt the user to take action to correct the high blood glucose level. In one example, the controller device 200 (via user interface 220) can suggest a bolus dosage based, at least in part, on the user's insulin load and can prompt the user to accept, modify, or decline the suggestion. The controller device 200 can prompt the user to enter information about a meal that the user may have consumed, but forgot to enter into the user interface 220. In another example, the controller device 200 can use a cellular phone network to call an emergency contact number programmed in the controller 200. After completion of operation 1035, the process 1000 can return to operation 1005 where the controller device 200 can receive additional information indicative of the user's blood glucose level.

If, in operation 1025, the controller 200 determines that the user's blood glucose level is not greater than the modified upper glucose alarm limit determined in operation 1015, the controller device 200 can perform operation 1040 to compare the user's blood glucose level to the modified lower glucose alarm limit obtained in operation 1015. During this operation 1040, if the controller 200 determines that the user's blood glucose level is less than the modified lower glucose alarm, the controller 200 can perform 1045 and communicate to the user a low blood glucose alarm (e.g., an audible alarm or alert, text on a display 222 describing an alarm or alert, a vibratory alarm or alert, another communicative output, or a combination thereof).

Still referring to FIG. 17, in operation 1050, the controller device 200 can prompt the user to take action to correct the low blood glucose level. In one example, the controller device 200 can suggest that the user consume some food. In another example, the controller 200 can suggest an amount (e.g., in carbohydrates) and type of food to consume. After completion of operation 1050, the process 1000 can return to operation 1005 where the controller device 200 can receive additional information indicative of the user's blood glucose level.

If, in operation 1040, the controller 200 determines that the user's blood glucose level is not less than the modified lower glucose alarm limit determined in operation 1015, this indicates that the user's glucose level is within the normal range (with the modified limits as described in operation 1015). As such, there may be no need to communicate a blood glucose alarm to the user. Rather, the process 1000 can return to operation 1005 where the controller device 200 will standby to receive subsequent information indicative of the user's blood glucose level.

In some embodiments, as described previously, a user can benefit from dynamically changing glucose alarm parameters to, for example, increase the sensitivity of particular glucose alarms, decreasing the likelihood and/or number of nuisance glucose alarms, or the like. The controller device 200 can, in response to a user's insulin load (e.g., TIL values, TIL % value, JOB, or the like), increase the sensitivity of glucose alarms and/or decrease the number of nuisance glucose alarms by modifying the upper and/or lower glucose alarm limits. A user's blood glucose level can then be compared to the modified glucose alarm limits to determine whether a low or high glucose alarm should be communicated to the user.

Figure 18:
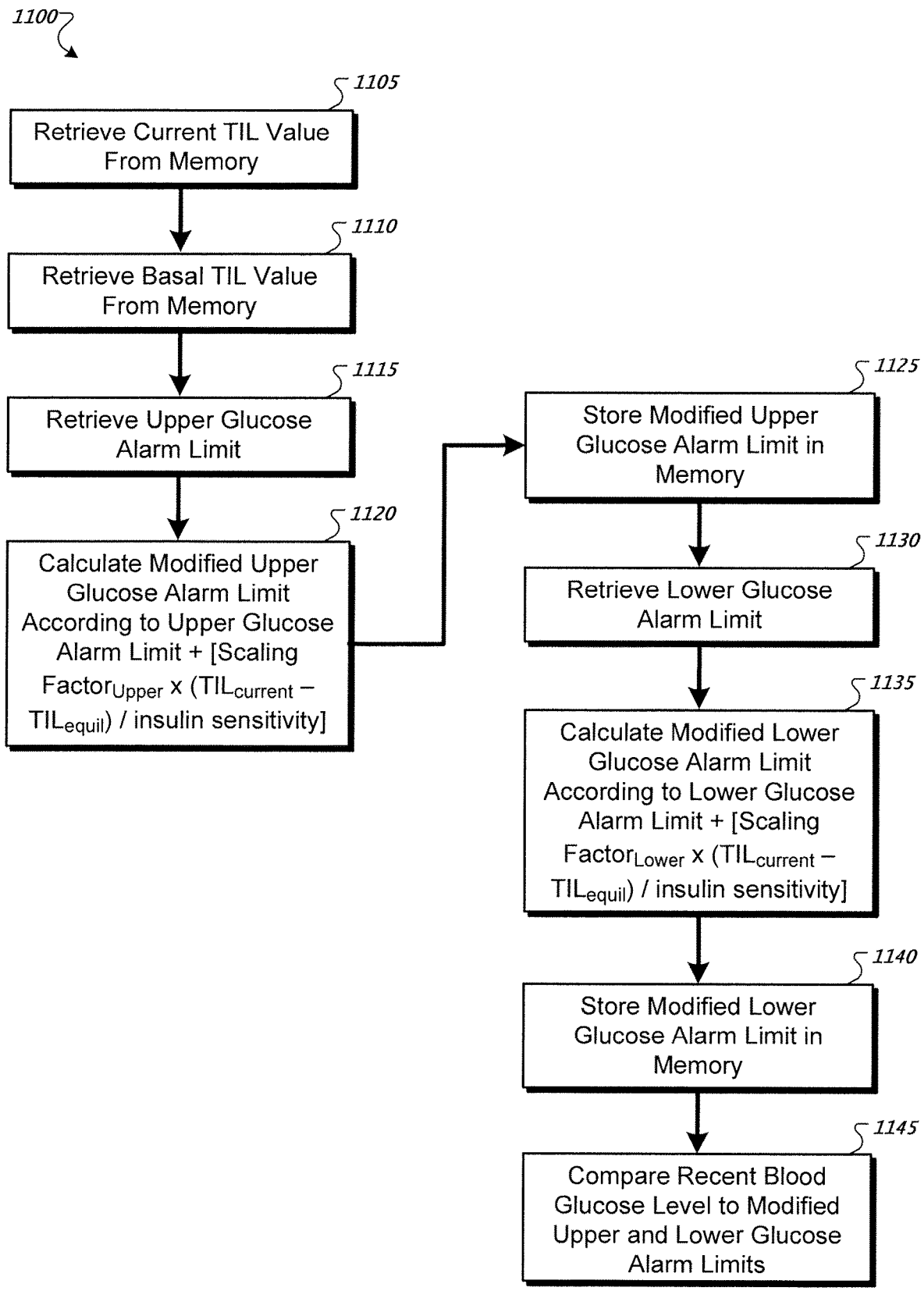
FIG. 18 is a flow diagram depicting an exemplary process used to modify high and low blood glucose alarm limits, in response to TIL values, in some embodiments.

Referring now to FIG. 18, the upper and lower glucose alarm limits associated with a user and stored in the controller 200 can be modified in response to the user's TIL value. As previously described in connection with FIG. 11, the controller device 200 can estimate a user's insulin load by calculating the user's TIL value from, for example, a user's recent basal deliveries, recent bolus dosages, and recent carbohydrate intake. This TIL value, along with additional information, such as the time the TIL value was calculated, can be stored in the memory (e.g., the memory chip 248) of the controller device 200 to be used later, for example, in modifying the user's glucose alarm limits. For example, as shown in FIG. 18, a process 1100 for modifying the upper and lower glucose alarm limits associated with a user, in response to the user's TIL value, can be implemented by the controller device 200. In operation 1105, the controller device 200 can retrieve a user's recent TIL value from memory. In some embodiments, instead of retrieving a recent TIL value from memory, the controller device 200 can initiate the calculation of a current TIL value and utilize this value in subsequent operations. Also, as previously described, the user can have a theoretical basal TIL value that is calculated, for example, when the user is receiving a constant basal rate, no bolus dosages, and is not consuming carbohydrates. In some embodiments, the user can have more than one basal rate, each with a corresponding theoretical basal TIL value. When calculated, the one or more basal TIL values can be stored in memory. In operation 1110, one or more of the user's theoretical basal TIL values can be retrieved by the controller device 200. As previously described, the controller device 200 can include upper and lower glucose alarm limits (e.g., that define a normal blood glucose range) that were previously programmed and stored in the memory of the controller device 200. In operation 1115, the controller device 200 can retrieve an upper glucose alarm limit from memory.

In some embodiments, if a user's insulin load is lower than normal, the likelihood of the user's blood glucose level rising is higher. In these circumstances, the controller device 200 can provide enhanced user safety by reducing the high glucose alarm limit, which can alert the user to a potentially dangerous increase in blood glucose level sooner than if the high glucose alarm limit was not modified. Alternatively, when the user's insulin load value is higher than normal, the likelihood of the user's blood glucose level rising is lower. In these circumstances, the controller device 200 may reduce the likelihood of nuisance alarms by raising the high glucose alarm limit, which can provide additional convenience to the user.

For example, in operation 1120, the controller device 200 can use the TIL value obtained during operation 1105, the theoretical basal TIL value obtained during operation 1110, and the upper glucose alarm limit obtained during operation 1115 to calculate a modified upper glucose alarm limit to increase the sensitivity of the high glucose alarm or decrease the number of nuisance high glucose alarms. For example, the modified upper glucose alarm limit can be calculated as follows:

Modified Upper Glucose Alarm Limit=Upper Glucose Alarm Limit+[Scaling Factor$_{Upper}$× (TIL$_{current}$-TIL$_{basal}$)/insulin sensitivity], where TIL$_{basal}$ represents the theoretical TIL that would have been generated based only on the user's basal insulin dosages (e.g., presuming no bolus insulin and no previous food components), Scaling Factor$_{Upper}$ represents a scaling factor (e.g., stored in the controller device 200) that can be used to correlate changes in the user's TIL values to changes in the user's upper glucose alarm limit, and the insulin sensitivity represents a preset parameter that correlates insulin received by a user to the resulting affect on that user's blood glucose level.

In operation 1125, the modified upper glucose alarm limit can be stored in the memory of the controller device 200, to be accessed later, for example, by the controller device 200 and compared to a user's current blood glucose level.

Still referring to FIG. 18, in some embodiments, if a user's insulin load is higher than normal, the likelihood of the user's blood glucose level falling is higher. In these circumstances, the controller device 200 may provide enhanced user safety by increasing the low glucose alarm limit, which can alert the user to a potentially dangerous decrease in blood glucose level sooner than if the low glucose alarm limit was not modified. Alternatively, when the user's insulin load value is lower than normal, the likelihood of the user's blood glucose level falling is lower. In these circumstances, the controller device 200 may reduce the likelihood of nuisance alarms by lowering the low glucose alarm limit, which can provide additional convenience to the user.

For example, in operation 1130, the controller device 200 can retrieve a lower glucose alarm limit from memory. In operation 1135, the controller device 200 can use the TIL value obtained during operation 1105, the basal TIL value obtained during operation 1110, and the lower glucose alarm limit obtained during operation 1130 to calculate a modified lower glucose alarm limit to increase the sensitivity of the low glucose alarm or decrease the likelihood and/or number of nuisance low glucose alarms. For example, the modified lower glucose alarm limit can be calculated as follows:

Modified Lower Glucose Alarm Limit=Lower Glucose Alarm Limit+[Scaling Factor$_{Lower}$× (TIL$_{current}$−TIL$_{basal}$)/insulin sensitivity]

where TIL$_{basal}$ represents the theoretical TIL that would have been generated based only on the user's basal insulin dosages (e.g., presuming no bolus insulin and no previous food components), Scaling Factor$_{Lower}$ represents a scaling factor, stored in the controller device 200, that can be used to correlate changes in the user's TIL values to changes in the user's lower glucose alarm limit, and the insulin sensitivity represents a preset parameter that correlates insulin received by a user to the resulting affect on that user's blood glucose level.

In operation 1140, the modified lower glucose alarm limit can be stored in the memory of the controller device 200, to be accessed later, for example, by the controller device 200 and compared to a user's current blood glucose level.

In operation 1145, the controller device 200 can compare a recent blood glucose level value to the modified upper and lower glucose alarm limits for the purpose of determining if the blood glucose value is outside of a normal range. One exemplary comparison operation was previously described in connection with FIG. 17 (refer to operations 1025-1050). It should be understood that, while process 1000 (FIG. 17) depicts a process in which glucose alarm limits are modified and compared to a user's most recent blood glucose level, in other embodiments, the controller device 200 may compare the user's blood glucose level to both the modified limits and the default glucose alarm limits. In such embodiments, different alarms can be communicated to the user to indicate whether the user's blood glucose level falls outside of the modified range or the default range. For example, if the user's current blood glucose level is below a default lower glucose limit, but above a modified lower limit, the user can be informed that the lower glucose alarm limit has been modified, but a low glucose alarm may not be given.

Figure 19:
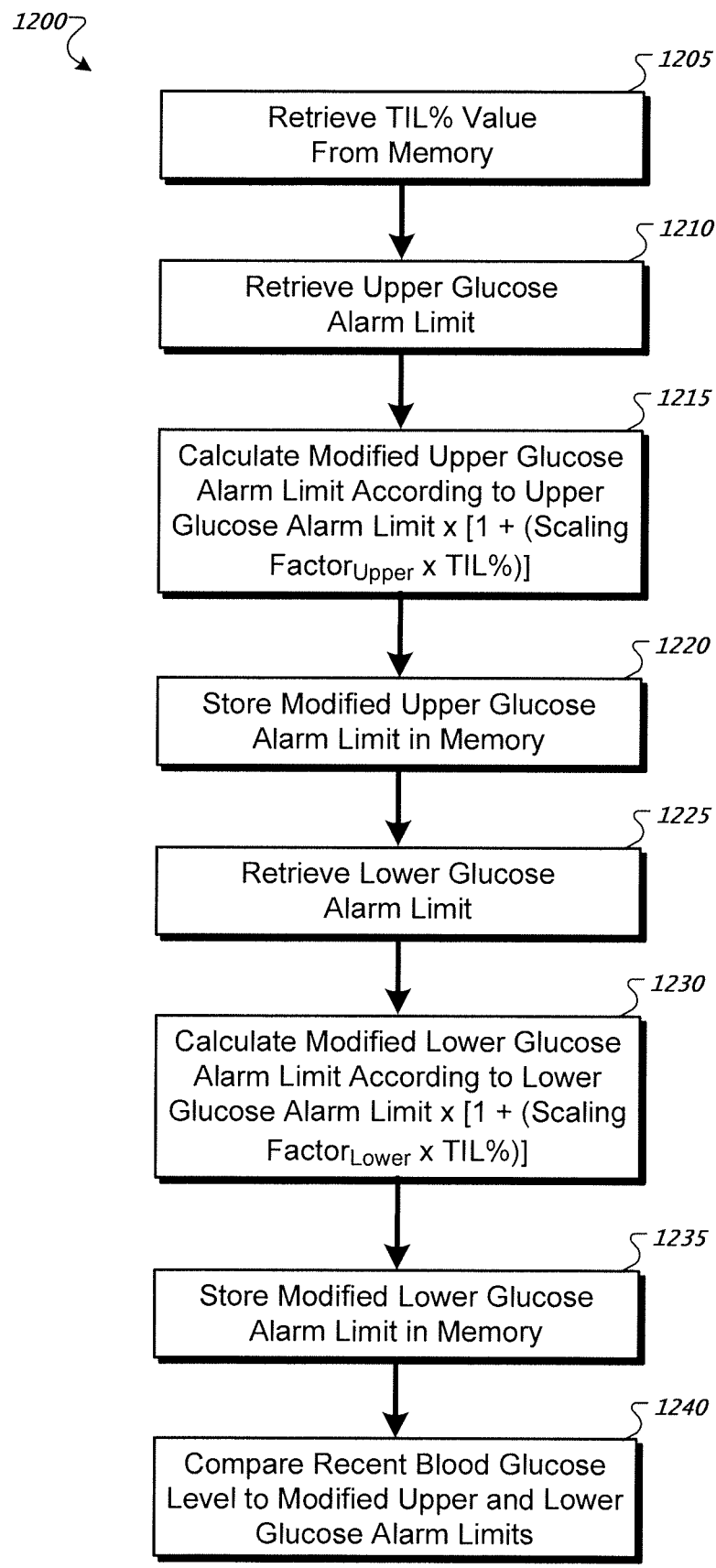
FIG. 19 is a flow diagram depicting an exemplary process used to modify high and low blood glucose alarm limits, in response to TIL % values, in some embodiments.

Referring now to FIG. 19, the upper and lower glucose alarm limits associated with a user and stored in the controller 200 can be modified in response to the user's TIL % value. As previously described in connection with FIG. 13, the controller device 200 can estimate a user's insulin load by calculating the user's TIL % value from, for example, a user's TIL value and the user's theoretical basal TIL value. This TIL % value, along with additional information, such as the time the TIL % value was calculated, can be stored in the memory (e.g., the memory chip 248) of the controller device 200 for use in, for example, modifying the user's glucose alarm limits. For example, a process 1200 for modifying the upper and lower glucose alarm limits associated with a user, in response to the user's TIL % value, can be implemented by the controller device 200. In operation 1205, the controller device 200 can retrieve a user's recent TIL % value from memory. In some embodiments, instead of retrieving a recent TIL % value from memory, the controller device 200 can initiate the calculation of a current TIL % value and utilize this value in subsequent operations.

As previously described, the controller device 200 can include upper and lower glucose alarm limits (e.g., that define a normal blood glucose range) that were previously stored in the memory of the controller device 200. In operation 1210, the controller device 200 can retrieve an upper glucose alarm limit from memory.

In some circumstances (e.g., a user's insulin load is lower than normal), the controller device 200 can provide enhanced user safety by reducing the high glucose alarm limit, which can alert the user to a potentially dangerous increase in blood glucose level sooner than if the high glucose alarm limit was not modified. In other circumstances (e.g., a user's insulin load value is higher than normal), the controller device 200 may reduce the likelihood of nuisance alarms by raising the high glucose alarm limit, which can provide additional convenience to the user. For example, in operation 1215, the controller device 200 can use the TIL % value obtained during operation 1205 and the upper glucose alarm limit obtained during operation 1210 to calculate a modified upper glucose alarm limit to increase the sensitivity of the high glucose alarm or decrease the likelihood and/or number of nuisance high glucose alarms. For example, the modified upper glucose alarm limit can be calculated as follows:

Modified Upper Glucose Alarm Limit=Upper Glucose Alarm Limit×[1+(Scaling Factor$_{Upper}$×TIL %)]

where Scaling Factor$_{Upper}$ represents a scaling factor, stored in the controller device 200, that can be used to correlate changes in the user's TIL % values to changes in the user's upper glucose alarm limit and can include factors such as the user's insulin sensitivity.

In operation 1220, the modified upper glucose alarm limit can be stored in the memory of the controller device 200, to be accessed later, for example, by the controller device 200 and compared to a user's current blood glucose level.

Still referring to FIG. 19, in some circumstances (e.g., a user's insulin load is higher than normal), the controller device 200 may provide enhanced user safety by increasing the low glucose alarm limit, which can alert the user to a potentially dangerous decrease in blood glucose level sooner than if the low glucose alarm limit is not modified. In other circumstances (e.g., a user's insulin load value is lower than normal), the controller device 200 may reduce the likelihood of nuisance alarms by lowering the low glucose alarm limit, which can provide additional convenience to the user. In operation 1225, the controller device 200 can retrieve a lower glucose alarm limit from memory. In operation 1230, the controller device 200 can use the TIL % value obtained during operation 1205 and the lower glucose alarm limit obtained during operation 1225 to calculate a modified lower glucose alarm limit to increase the sensitivity of the low glucose alarm or decrease the number of nuisance low glucose alarms. For example, the modified upper glucose alarm limit can be calculated as follows:

Modified Lower Glucose Alarm Limit=Lower Glucose Alarm Limit×[1+(Scaling Factor$_{Lower}$×TIL %)]

where Scaling Factor$_{Lower}$ represents a scaling factor, stored in the controller device 200, that can be used to correlate changes in the user's TIL % values to changes in the user's lower glucose alarm limit, and can include factors such as the user's insulin sensitivity.

In operation 1235, the modified lower glucose alarm limit can be stored in the memory of the controller device 200, to be accessed later, for example, by the controller device 200 and compared to a user's current blood glucose level.

In operation 1240, the controller device 200 can compare a recent blood glucose level value to the modified upper and lower glucose alarm limits for the purpose of determining if the blood glucose value is outside of a normal range. An exemplary comparison was described in connection with FIG. 17 (refer to operations 1025-1050). As previously described, in some alternative embodiments other than the process shown in FIG. 17, the controller device 200 may compare the user's blood glucose level to both the modified limits and the default glucose alarm limits. In these embodiments, different alarms can be communicated to the user to indicate whether the user's blood glucose level falls outside of the modified range or the default range. For example, if the user's current blood glucose level is above a default upper glucose limit, but below a modified upper limit, the user can be informed that the upper glucose alarm limit has been modified, but a high glucose alarm may not be given.

In some embodiments, as described previously, a user can benefit from increasing the sensitivity of glucose alarms and/or decreasing the likelihood of nuisance glucose alarms. The controller 200 can, in response to a user's insulin load (e.g., TIL values, TIL % value, JOB, or the like), increase the sensitivity of glucose alarms and/or decrease the number of nuisance glucose alarms by modifying the upper and/or lower glucose alarm limits. A user's blood glucose level can then be compared to the modified glucose alarm limits to determine whether a low or high glucose alarm should be communicated to the user. In some embodiments, for example as described in connection with FIGS. 18-19, the glucose alarm limits can be modified using equations that incorporate TIL values, TIL % values, theoretical basal TIL values, or the like. In some embodiments, the glucose alarm limits can be modified in response to a user's insulin load (e.g., TIL values, TIL % values, or the like), but the insulin load values may not be used in the equations employed to calculate the modified the alarm limits.

Figure 20:
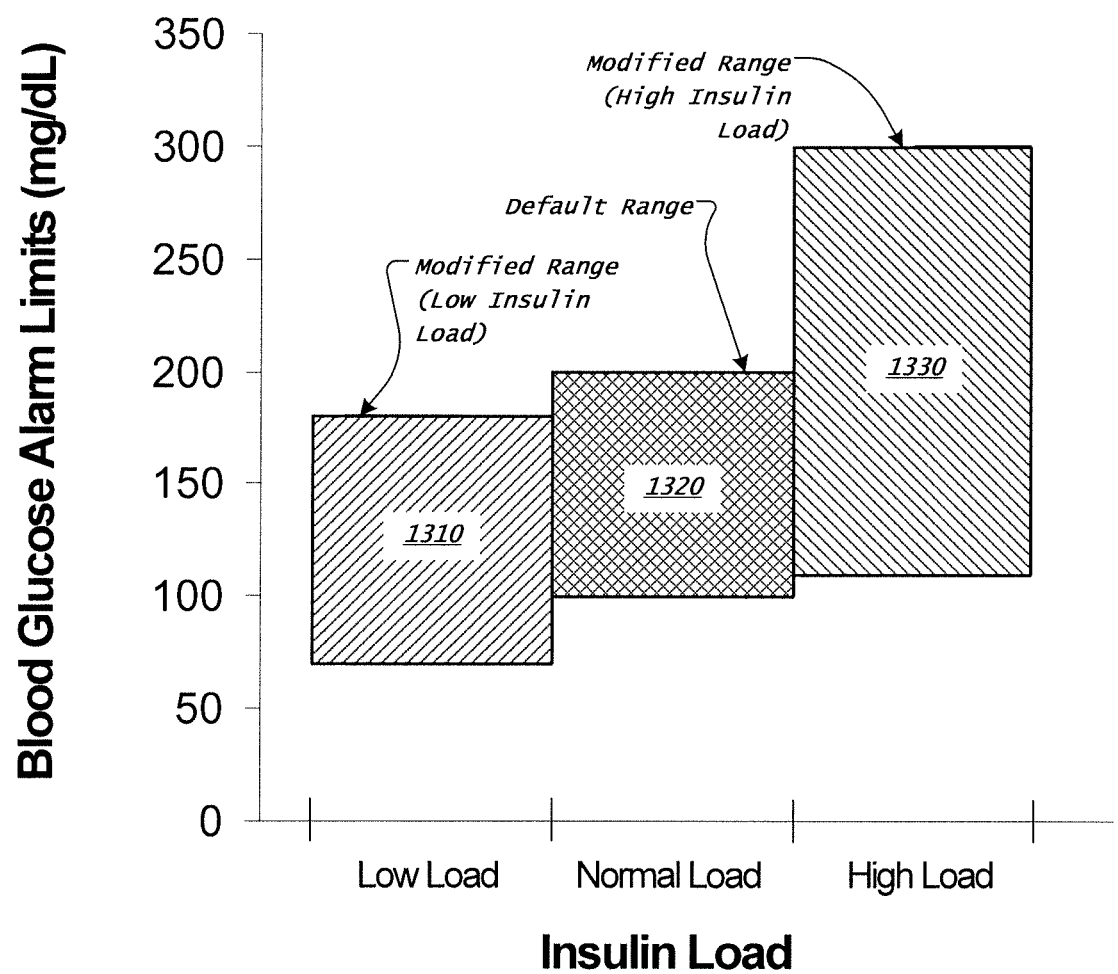
FIG. 20 is a diagram depicting three exemplary TIL ranges and the corresponding normal blood glucose ranges, in some embodiments.

Referring now to FIG. 20, in some embodiments, a user's insulin load value can be compared to upper and/or lower insulin load threshold values to determine if the insulin load value is outside a normal range. If the insulin load value is within a "Normal" range (e.g., between 1.5 and 3.5 units in one particular example), the controller device 200 may not modify the upper and lower glucose alarm limits, leaving the glucose range as seen in default glucose alarm limit range 1300. If the insulin load value falls below the "Normal" range (e.g., into a "Low" range), the controller device 200 can increase the sensitivity of the upper glucose alarm limit and decrease the sensitivity of the lower glucose alarm limit by decreasing the value of each, as seen in low-load modified range 1310. If the insulin load value rises above the "Normal" range (e.g., into a "High" range, the controller device 200 can decrease the sensitivity of the upper glucose alarm limit and increase the sensitivity of the lower glucose alarm limit by increasing the value of each, as seen in high-load modified range 1320.

In some embodiments, the upper and lower glucose alarm limits can be modified by predetermined amounts based on the insulin load value. For example, if the insulin load value falls below the "Normal" range (e.g., into the "Low" range), the controller device 200 can decrease the upper glucose alarm limit by 20 mg/dL (e.g., from 200 mg/dL to 180 mg/dL in this example) and decrease the lower glucose alarm limit by 30 mg/dL (e.g., from 100 mg/dL to 70 mg/dL in this example). On the other hand. if the insulin load value rises above the "Normal" range (e.g., into the "High" range), the controller device 200 can increase the upper glucose alarm limit by 100 mg/dL (e.g., from 200 mg/dL to 300 mg/dL in this example) and increase the lower glucose alarm limit by 10 mg/dL (e.g., from 100 mg/dL to 110 mg/dL in this example).

In alternative embodiments, the upper and lower glucose limits can be modified by percentage amounts based on the insulin load value. For example, if the insulin load value falls below the "Normal" range (e.g., into a "Low" range), the controller device 200 can decrease the upper glucose alarm limit by 15% (e.g., from 200 mg/dL to 170 mg/dL) and decrease the lower glucose alarm limit by 40% (e.g., from 100 mg/dL to 60 mg/dL). If the insulin load value rises above a "Normal" range (e.g., into a "High" range), the controller device 200 can increase the upper glucose alarm limit by 40% (e.g., from 200 mg/dL to 280 mg/dL) and increase the lower glucose alarm limit by 15% (e.g., from 100 mg/dL to 115 mg/dL).

As previously described, such modifications to the alarms limits can be based at least in part of the user's insulin load. Thus, in some embodiments, the glucose alarm limits can be modified (e.g., by fixed amounts, percentages, or the like) in response to the user's TIL value or TIL % value rising above or falling below a normal range. In still other embodiments, a user's glucose alarm limits can be modified in response to the user's insulin load (e.g., TIL value, TIL % value, insulin-on-board estimations, or the like) being outside of a normal range using equations, such as those described in connection with FIGS. 18-19, to modify the upper and lower glucose alarm limits.

Figure 21:
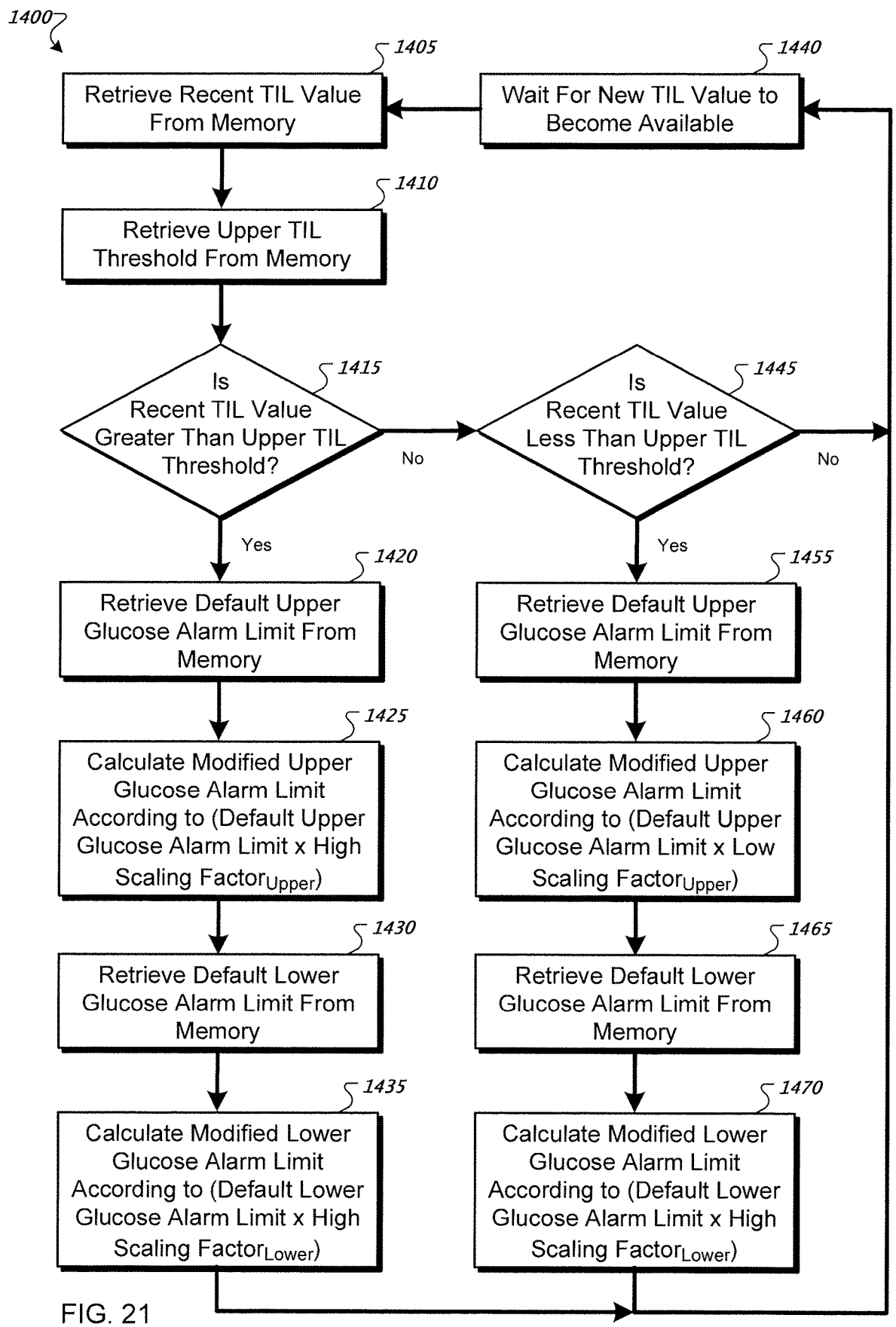
FIG. 21 is a flow diagram depicting an exemplary process used to modify high and low blood glucose alarm limits, in response to TIL values, in some embodiments.

Referring now to FIG. 21, the controller device 200 can be used to modify a user's upper and lower glucose alarm limits in response to a comparison between a user's insulin load (e.g., TIL value, TIL % value, JOB, or the like) and a predetermined range. For example, a process 1400 for modifying a user's upper and lower glucose alarm limits in response to a comparison between the user's current TIL value and upper and lower TIL threshold values can be implemented by the controller device 200. As previously described, the controller device 200 can determine a user's TIL values and store these values in memory. In operation 1405, the controller device 200 can retrieve a user's recent TIL value from memory (e.g., the memory chip 248). In some embodiments, the controller device 200 can retrieve the TIL value by initiating a new calculation for a current TIL value. In operation 1410 the controller device 200 can retrieve, from memory, an upper TIL threshold.

In operation 1415, the controller device 200 can compare the TIL value retrieved in operation 1405 to the upper threshold retrieved in operation 1410. If the TIL value is greater than the upper TIL threshold value, the process 1400 continues to operation 1420 where the controller device 200 can retrieve an upper glucose alarm limit from memory. In operation 1425, the controller device 200 can calculate a modified upper glucose alarm limit that can be used to, for example, decrease the sensitivity of the high glucose alarm. In this example, the modified upper glucose alarm limit can be calculated as follows:

$$\text{Modified Upper Glucose Alarm Limit} = \text{Upper Glucose Alarm Limit} \times \text{High Scaling Factor}_{Upper}$$

where High Scaling Factor$_{Upper}$ represents a scaling factor (e.g., stored in the controller device 200) that can be used to modify the user's upper glucose alarm limit in response to high TIL values.

In operation 1430, the controller device 200 can retrieve a lower glucose alarm limit from memory. In operation 1435, the controller device 200 can calculate a modified lower glucose alarm limit that can be used to, for example, increase the sensitivity of the low glucose alarm. The modified lower glucose alarm limit can be calculated as follows:

Modified lower Glucose Alarm Limit=Lower Glucose Alarm Limit×High Scaling Factor$_{Lower}$ where High Scaling Factor$_{Lower}$ represents a scaling factor (e.g., stored in the controller device 200) that can be used to modify the user's lower glucose alarm limit in response to high TIL values.

After completing operation 1435, the process 1400 can execute operation 1440 where the controller device 200 can standby for a new TIL value to become available before returning to operation 1400.

It should be understood that, after the modified upper and lower glucose alarm limits are calculated, the new alarm limit values can be stored in memory of the controller device 200. As such, the controller device 200 can compare a recent blood glucose level value to the modified upper and lower glucose alarm limits for the purpose of determining if the blood glucose value is outside of a normal range. One exemplary comparison operation was previously described in connection with FIG. 17 (refer to operations 1025-1050).

Revisiting now the comparison made during operation 1415, if the controller device 200 determines that the TIL value retrieved during operation 1405 is not greater than the upper TIL threshold value, the process 1400 can execute operation 1445 and the controller device 200 can retrieve, from memory, a lower TIL threshold. In operation 1445, the controller device 200 can compare the TIL value retrieved in operation 1405 to the lower threshold value from memory. If the TIL value is less than the lower TIL threshold value, the process 1400 can execute operation 1455 where the controller device 200 can retrieve an upper glucose alarm limit from memory. In operation 1460, the controller device 200 can calculate a modified upper glucose alarm limit that can be used to, for example, increase the sensitivity of the high glucose alarm. In this example, the modified upper glucose alarm limit can be calculated as follows:

Modified Upper Glucose Alarm Limit=Upper Glucose Alarm Limit×Low Scaling Factor$_{Upper}$ where Low Scaling Factor$_{Upper}$ represents a scaling factor (e.g., stored in the controller device 200) that can be used to modify the user's upper glucose alarm limit in response to low TIL values.

In operation 1465, the controller device 200 can retrieve a lower glucose alarm limit from memory. In operation 1470, the controller device 200 can calculate a modified lower glucose alarm limit that can be used to, for example, decrease the sensitivity of the low glucose alarm. In this example, the modified lower glucose alarm limit can be calculated as follows:

Modified lower Glucose Alarm Limit=Lower Glucose Alarm Limit×Low Scaling Factor$_{Lower}$ where Low Scaling Factor$_{Lower}$ represents a scaling factor (e.g., stored in the controller device 200) that can be used to modify the user's lower glucose alarm limit in response to low TIL values.

After completing operation 1470, the process 1400 can continue on to operation 1440 where the controller device 200 can standby for a new TIL value to become available before returning to operation 1400.

As previously described, after the modified upper and lower glucose alarm limits are calculated, the new alarm limit values can be stored in memory of the controller device 200. As such, the controller device 200 can compare a recent blood glucose level value to the modified upper and lower glucose alarm limits for the purpose of determining if the blood glucose value is outside of a normal range. One exemplary comparison operation was previously described in connection with FIG. 17 (refer to operations 1025-1050).

Revisiting now the comparison made during operation 1445, if the controller device 200 determines that the TIL value retrieved during operation 1405 is not less than the lower TIL threshold value, the process 1400 can execute operation 1440 where the controller device 200 can standby for a new TIL value to become available before returning to operation 1400. In the previously described embodiment, three insulin load ranges (e.g., "Normal", "High", and "Low") were used to determined how the glucose alarm limits were to be modified. In other embodiments, a different number of insulin load ranges (e.g., 4, 2, 5, or the like) can be used, each defining a different way to modify the glucose alarm limits. In some embodiments, other insulin load values (e.g., TIL %, JOB, or the like) can be used to determine if a user's blood glucose alarm limits are to be modified. In some embodiments, the upper and lower glucose alarm limits can be modified, when the user's insulin load is outside of a normal range, by equations similar to the equations described in connection with FIGS. 18-19.

Referring now to FIGS. 22-25, some embodiments of the controller device 200 can be used to provide alarms other than "high" or "low" blood glucose levels. For example, when receiving data indicative of a user's blood glucose levels e.g., data from the monitoring device 50, blood glucose levels input into the user interface 220, data from a glucose test strip reader built into the controller device 200, or the like, the controller device 200 can be configured to provide one or more of a "missed bolus" alarm and a "missed meal" alarm. The controller device 200 can identify, from stored blood glucose values, one or more conditions that indicate a user experienced a missed bolus situation or a missed meal situation. Identifying a missed meal and/or missed bolus situation can benefit the user in that this information can be used by the controller device 200 to prompt corrective action (e.g., prompting the user to consume carbohydrates, prompting the user for input in order to suggest a bolus dosage, prompting the user to input data related to a meal previously consumed, or the like) before the user's blood glucose level has risen or fallen out of a normal range. In some embodiments, the "missed meal" alarm and/or the "missed bolus" alarm can be suspended during particular periods of the day (e.g., when the user is sleeping) to minimize or eliminate the occurrence of nuisance alarms.

Figure 22:
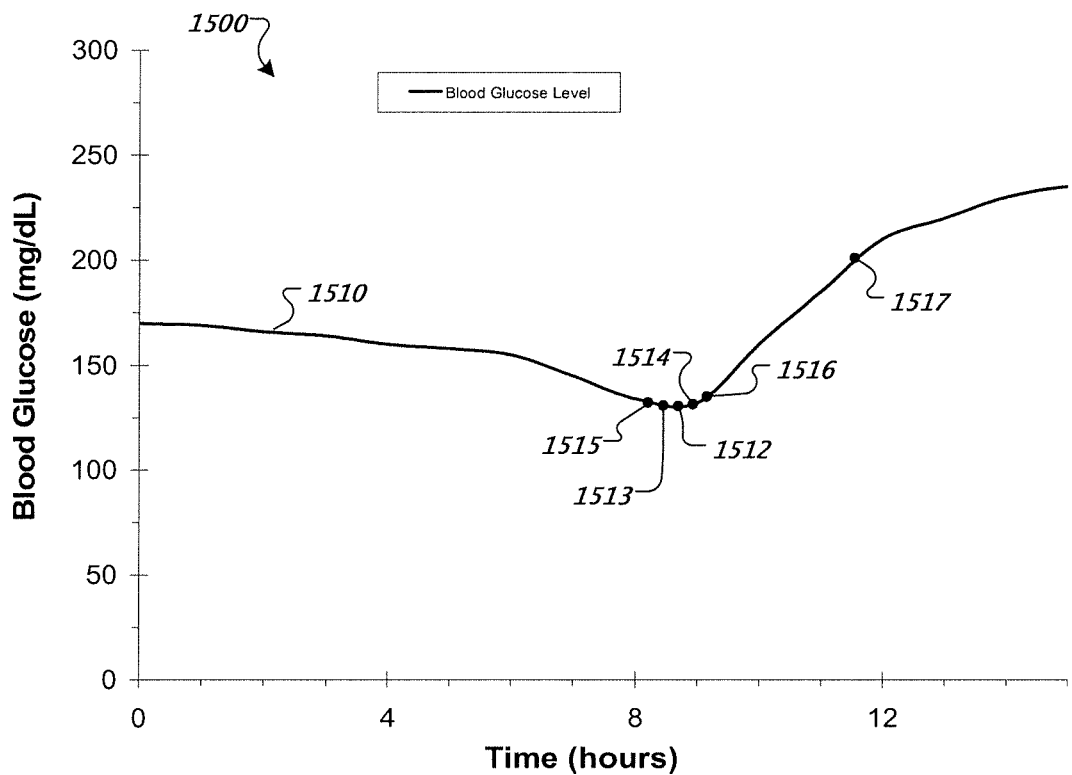
FIG. 22 is a diagram depicting an exemplary blood glucose curve, including a missed bolus, and the corresponding 2nd derivative of that curve.

Referring now to FIG. 22, in some embodiments, the controller device 200 can utilize stored data indicative of a user's blood glucose level (e.g., detected by the monitoring device 50) to identify a missed bolus situation that can occur, for example, when the user consumes a meal containing carbohydrates, but does receive a bolus to offset the carbohydrate intake. A missed bolus situation can occur when a user forgets to enter a meal into the controller device 200, does not accept a suggested bolus dosage, cancels a bolus dosage, or the like. As part of the normal operation of the infusion pump system 10, the controller device 200 can periodically (e.g., every one minute, every two minutes, every five minutes, every fifteen minutes, every hour, every two hours) or selectively (e.g., when prompted by the user or the like) receive data indicative of a user's blood glucose level. For example, the controller device 200 may receive detected glucose information from the monitoring device 50 every one minute, every two minutes, every five minutes, every fifteen minutes, or the like. Such data can be stored in a memory device of the controller device 200. In these circumstances, the controller device 200 can retrieve previously stored data indicative of a user's blood glucose level for a period of time (e.g., a recent 15-minute period, a recent 30-minute period, a recent 1-hour period, a recent 3-hour period, or the like) and can evaluate this data for information indicative of a missed bolus situation.

In FIG. 22, graph 1500 provides an example of a blood glucose curve 1510 generated from the blood glucose data that was stored in the memory of the controller device 200. In some embodiments, the controller device 200 can be configured to recognize one or more patterns, within the data depicted by the glucose curve 1510, indicative of a missed bolus situation. For example, the controller device 200 can identify a potential missed bolus situation by recognizing a local minimum within the glucose curve 1510, such as the local minimum that occurs proximate to data point 1512. Exemplary methods used by the controller device 200 to recognize a local minimum can include determining the local minimum by evaluating the curve 1510 graphically and/or determining the local minimum mathematically. In some embodiments, the controller device 200 can identify a local minimum by identifying data points on the curve (e.g., the data point 1512) where the closest data point to the left (such as the data point 1513) and the closest data point to the right (e.g., the data point 1514) are greater than the data point itself. In some embodiments, the controller device 200 can estimate the first and second derivatives of the glucose curve 1510 and can test the first and second derivatives for conditions that indicate a local minimum. For example, if the controller device 200 locates a point in the curve 1510 where the first derivative is equal to zero and the second derivative is positive, the located point may be a local minimum and can potentially indicate that the user is experiencing a missed bolus situation.

Still referring to FIG. 22, the controller device 200 can be configured to perform other operations to determine if the user is experiencing a missed bolus situation. In some embodiments, the controller device 200 may evaluate more than two neighboring points (e.g., more than one on each side) of a test point when determining a missed bolus situation. The controller device 200 can evaluate the blood glucose data for a period of time before and a period of time after a potential local minimum to determine if the user is experiencing a missed bolus situation. For example, the controller device 200 can evaluate a one hour period of time (e.g., one-half hour before the point 1512 and one-half hour after the point 1512) to determine if the data depicted by the glucose curve 1510 indicates a missed meal situation. The controller device 200 can evaluate all the points, within a period of time (e.g., one-half hour), to the left of a local minimum and all of the points, within a period of time (e.g., one-half hour), to the right of the local minimum. If each of the evaluated points prior to the local minimum has a lesser value than the previous point (moving from lowest time to highest time), and if each of the evaluated points to the right of the local minimum has a greater value than the previous point (moving from lowest time to highest time), then the controller device 200 can determine that the local minimum indicates that the user is experiencing a missed bolus situation. For example, if the order of data points 1512, 1513, and 1515, from highest to lowest value, is point 1515, point 1513, and point 1512 and the order of points 1512, 1514, and 1516, from lowest to highest value, is point 1512, point 1514, and point 1516, then the controller device 200 can identify a missed bolus situation. It should be understood, that in particular alternative embodiments, the controller device 200 can be configured to identify a possible missed bolus situation where the blood glucose data points reveal a change in slope (e.g., from a steep downward slope toward a flatter slope) rather than a complete reversal of slope at a local minimum.

When examining the user's blood glucose data (refer to blood glucose curve 1510) prior to point 1512, the user's blood glucose level is not only within a normal range (e.g., 100 mg/dL to 200 mg/dL), but the values are falling. If only considering the blood glucose level (refer to curve 1510), the controller device 200 may not identify the existence of a situation that needs to be corrected until point 1517 where the user's blood glucose level rises above the user's normal blood glucose range (e.g., 100 mg/dL to 200 mg/dL in this embodiment). In the example depicted here, the user's blood glucose level remains within the normal range until reaching point 1517 (at about time=11.5 hours). After the point 1517, the controller device 200 can alert the user of a high blood glucose level and can prompt the user to take corrective action (e.g., receive a bolus dosage of insulin). However, the controller device 200 can monitor the user's blood glucose data for the purpose of identifying "missed bolus" situations before the user's blood glucose level increases beyond the upper alarm limit. In the embodiment described here, the controller device 200 can identify the presence of a missed bolus situation prior to point 1517 (e.g., at point 1514, at point 1516, or the like)—about 2 to about 2.5 hours prior to point 1517 when the user's blood glucose level increases beyond the upper alarm limit. In this example, the controller device 200 can alert the user of the potential missed bolus situation at about time=9.25 hours and prompt the user to take corrective action, possibly avoiding the potentially unsafe increase in blood glucose level.

Still referring to the embodiment depicted by FIG. 22, when the controller device identifies a missed bolus situation, the controller device 200 can prompt the user to enter a previously consumed meal. For example, the missed bolus situation could have been caused by the user forgetting to enter a previously consumed meal that included carbohydrates and the prompt, by the controller device 200, can remind the user to enter this information. Thereafter, the controller device 200 can suggest a bolus insulin dosage to offset the consumed carbohydrates. If the user does not enter meal information, the controller device 200 can prompt the user to receive a bolus dosage based on, for example, the slope of the blood glucose curve 1510 at the latest point where a slope can be calculated (e.g., at point 1514). In the example depicted in FIG. 22, the controller device 200 can prompt the user to take corrective action about 1.5 to 2 hours earlier, if the controller device 200 monitors the blood glucose data for patterns indicative of a missed bolus situation, than if the controller device 200 monitors only the blood glucose level (refer to curve 1510). Such a feature can provide enhanced protection for the user, who would have the opportunity to select a corrective bolus before the blood glucose level increased above the normal range, potentially maintaining the user's blood glucose in a normal range when it would otherwise rise to an unsafe level.

Figure 23:
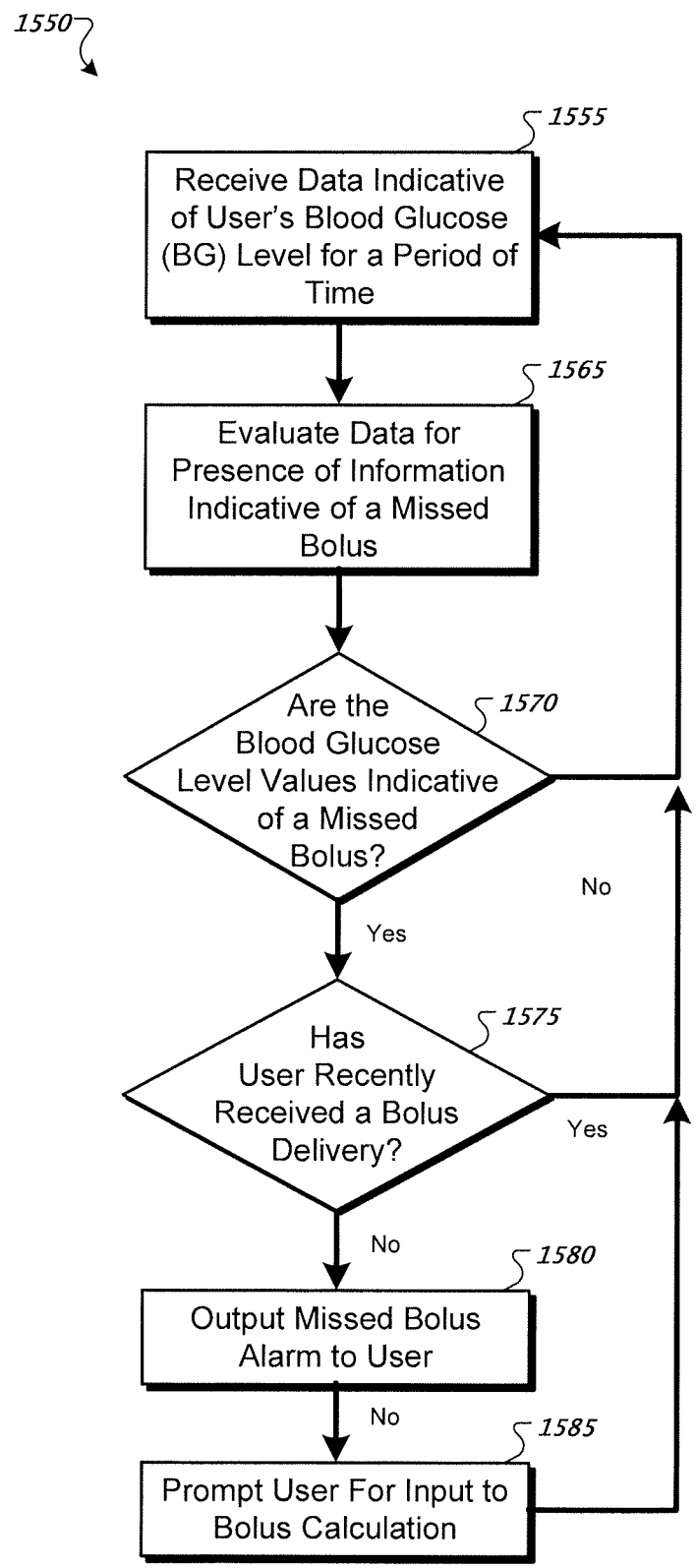
FIG. 23 is a flow diagram depicting an exemplary process used to identify a missed bolus using blood glucose information, in some embodiments.

Referring now to FIG. 23, the controller device 200 can be used to identify a missed bolus situation that can be indicative of, for example, the user consuming a meal and not receiving a bolus dosage of insulin to offset the meal carbohydrates. In some embodiments, a process 1550 for identifying a missed bolus situation using blood glucose information can be implemented by the controller device 200. As previously described, the controller device 200 can receive and store information indicative of a user's blood glucose level. In operation 1555, the controller device 200 can receive data indicative of the user's blood glucose level for a period of time from the monitoring device 50. In operation 1565, the controller device 200 can evaluate the blood glucose data for information that is indicative of a missed bolus situation. For example, the controller device 200 can be configured to analyze the data points from (e.g., a recent 15-minute period, a recent 30-minute period, a recent 1-hour period, a recent 3-hour period, or the like). During the analysis, the controller device 200 can locate local minima as described previously in connection with FIG. 22. In another example, the controller device 200 can identify local minima and apply additional tests, such as those described in connection with FIG. 22, to determine if data indicative of a missed bolus situation is present. In an alternative example, the controller device 200 can identify a possible missed bolus situation where the blood glucose data points reveal a change in slope (e.g., from a steep downward slope toward a flatter slope) rather than a complete reversal of slope at a local minimum. If, in operation 1570, the controller device 200 does not identify information indicative of a missed bolus situation, the process 1550 can return to operation 1555 where the controller device 200 can standby to receive additional blood glucose data.

If the controller device 200, in operation 1570, does identify information indicative of a missed bolus situation, the process 1550 can execute process 1575 in which the controller device 200 can check if the user has recently received a bolus dosage. For example, if the user received a bolus delivery fifteen minutes prior to the identification of the missed bolus situation, the insulin received during that bolus dosage may not have significantly acted yet on the user. In this example, the controller device 200 may have identified a missed bolus situation because the insulin delivered did not yet have time to take effect. In this example, no alert is communicated to the user and the process 1550 can return to operation 1555 where the controller device 200 can standby to receive additional blood glucose data.

If, in operation 1575, the controller device 200 determines that the user has not recently received a bolus dosage of insulin, the process 1550 can execute operation 1580 and the controller device 200 can output a "missed bolus" alarm to the user. At this time, the user can be optionally prompted to enter data indicative of a previously consumed meal that was not previously entered into the controller device 200. In operation 1585, the controller device 200 can prompt the user for input to a bolus calculation. For example, after the "missed bolus" alarm is communicated, the user interface 220 of the controller device 200 can enter a bolus suggestion menu in which the user is prompted to enter data so that a suitable bolus dosage can be calculated. The suggested bolus dosage can be displayed to the user, and the user can be prompted to begin delivery of the bolus dosage (to thereby correct the previously missed bolus situation before the user's blood glucose level reaches the upper alarm limit conditions).

Figure 24:
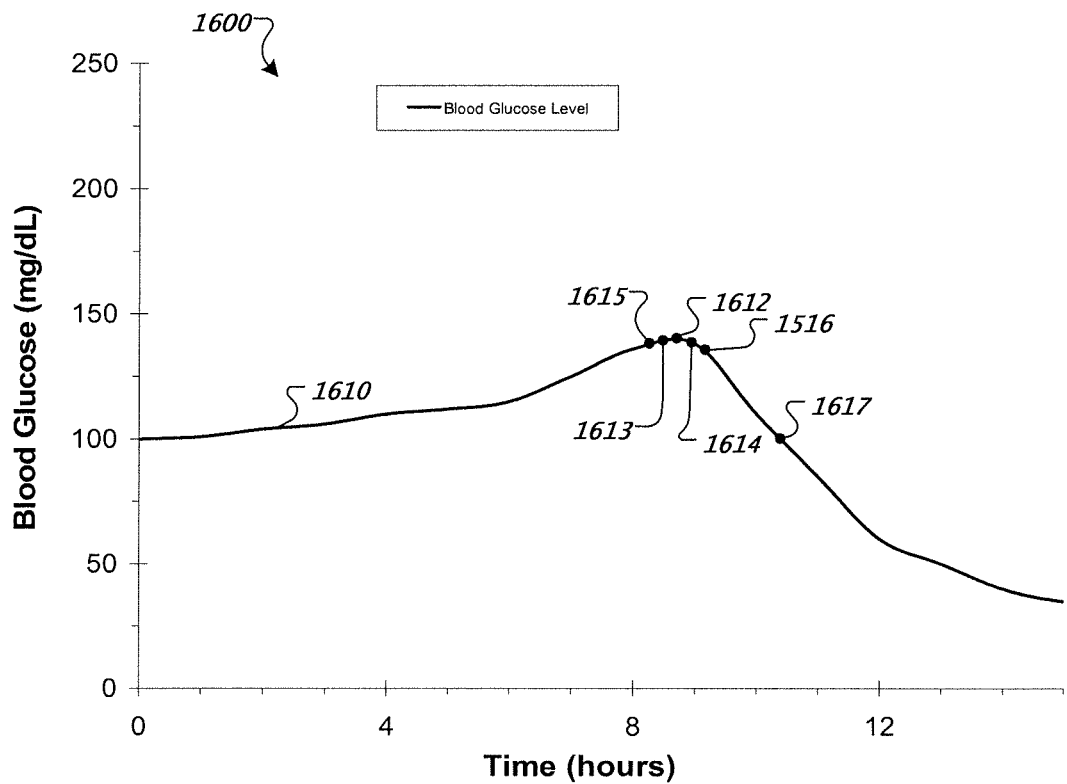
FIG. 24 is a diagram depicting an exemplary blood glucose curve, including a missed meal, and the corresponding 2nd derivative of that curve.

Referring now to FIG. 24, in some embodiments, the controller device 200 can utilize stored data indicative of a user's blood glucose level (e.g., detected by the monitoring device 50) to identify a "missed meal" situation. For example, the missed meal situation may arise when the user receives a bolus dosage of insulin in response to a planned meal, but then fails to consume that particular meal. As part of the normal operation of the infusion pump system 10, the controller device 200 can periodically (e.g., every one minute, every two minutes, every five minutes, every fifteen minutes, every hour, every two hours) or selectively (e.g., when prompted by the user or the like) receive data indicative of a user's blood glucose level. For example, the controller device 200 may receive detected glucose information from the monitoring device 50 every one minute, every two minutes, every five minutes, every fifteen minutes, or the like. Such data can be stored in a memory device of the controller device 200. In these circumstances, the controller device 200 can retrieve previously stored data indicative of a user's blood glucose level for a period of time (e.g., a recent 15-minute period, a recent 30-minute period, a recent 1-hour period, a recent 3-hour period, or the like) and can evaluate this data for the presence of information indicative of a "missed meal" situation. In certain embodiments, the controller device 200 may initiate the inquiry into the "missed meal" situation only after the delivery of a meal bolus of insulin (e.g., within a 1-hour period after the delivery of a meal bolus).

In FIG. 24, graph 1600 provides an example of a blood glucose curve 1610 generated from the blood glucose data that was stored in the memory of the controller device 200. In some embodiments, the controller device 200 can be configured to recognize one or more patterns, within the data depicted by the glucose curve 1610, indicative of a missed meal situation. For example, the controller device 200 can identify a potential missed meal situation by recognizing a local maximum within the glucose curve 1610, such as the local maximum that occurs proximate to data point 1612. Exemplary methods used by the controller device 200 to recognize a local maximum can include determining the local maximum by evaluating the curve 1610 graphically and/or determining the local maximum mathematically. In some embodiments, the controller device 200 can identify a local maximum by identifying data points on the curve (e.g., the data point 1612) where the closest data point to the left (such as the data point 1613) and the closest data point to the right (e.g., the data point 1614) are less than the data point itself. In some embodiments, the controller device 200 can estimate the first and second derivatives of the glucose curve 1610 and can test the first and second derivatives for conditions that indicate a local maximum. For example, if the controller device 200 locates a point in the curve 1610 where the first derivative is equal to zero and the second derivative is negative, the located point may be a local maximum and can potentially indicate that the user is experiencing a missed meal situation.

Still referring to FIG. 24, the controller device 200 can be configured to perform other operations to determine if the user is experiencing a missed meal situation. In some embodiments, the controller device 200 may evaluate more than two neighboring points (e.g., more than one on each side) of a test point when determining a missed meal situation. The controller device 200 can evaluate the blood glucose data for a period of time before and a period of time after a potential local maximum to determine if the user is experiencing a missed meal situation. For example, the controller device 200 can evaluate a one hour period of time (e.g., one-half hour before the point 1612 and one-half hour after the point 1612) to determine if the data depicted by the glucose curve 1610 indicates a missed meal situation. The controller device 200 can evaluate all the points, within a period of time (e.g., one-half hour), to the left of a local maximum and all of the points, within a period of time (e.g., one-half hour), to the right of the local maximum. If each of the evaluated points prior to the local maximum has a greater value than the previous point (moving from lowest time to highest time), and if each of the evaluated points to the right of the local maximum has a lesser value than the previous point (moving from lowest time to highest time), then the controller device 200 can determine that the local maximum indicates that the user is experiencing a missed meal situation. For example, if the order of data points 1612, 1613, and 1615, from lowest to highest value, is point 1615, point 1613, and point 1612 and the order of points 1612, 1614, and 1616, from highest to lowest value, is point 1612, point 1614, and point 1616, then the controller device 200 can identify a missed meal situation. It should be understood, that in particular alternative embodiments, the controller device 200 can be configured to identify a possible missed meal situation where the blood glucose data points reveal a change in slope (e.g., from a steep upward slope toward a flatter slope) rather than a complete reversal of slope at a local maximum.

When examining the user's blood glucose data (refer to blood glucose curve 1610) prior to point 1612, the user's blood glucose level is not only within a normal range (e.g., 100 mg/dL to 200 mg/dL), but the values are rising. If only considering the blood glucose level (refer to curve 1610), the controller device 200 may not identify the existence of a situation that needs to be corrected until point 1617 where the user's blood glucose level falls below the user's normal blood glucose range (e.g., 100 mg/dL to 200 mg/dL in this embodiment). In the example depicted here, the user's blood glucose level remains within the normal range until reaching point 1617 (at about time=10.25 hours). After the point 1617, the controller device 200 can alert the user of a low blood glucose level and can prompt the user to take corrective action (e.g., consume a meal of carbohydrates). However, the controller device 200 can monitor the user's blood glucose data for the purpose of identifying "missed meal" situations before the user's blood glucose level decreases below the lower alarm limit. In the embodiment described here, the controller device 200 can identify the presence of a missed meal situation prior to point 1617 (e.g., at point 1614, at point 1616, or the like)—about 1 to about 1.5 hours prior to point 1617 when the user's blood glucose level decreases below the lower alarm limit. In this example, the controller device 200 can alert the user of the potential missed meal situation at about time=9 hours and prompt the user to take corrective action, possibly avoiding the potentially unsafe decrease in blood glucose level.

Still referring to the embodiment depicted by FIG. 24, when the controller device identifies a missed meal situation, the controller device 200 can prompt the user to consume a previously entered meal. For example, the missed meal situation could have been caused by the user neglecting to consume a meal that was previously entered into the controller device 200. When alerted by the controller device 200, the user can be reminded to consume this previously entered meal. If the user has consumed all meals that were previously entered into the controller device 200, the controller device 200 can prompt the user to consume a carbohydrate including meal that is based on, for example, the slope of the blood glucose curve 1610 at the latest point where a slope can be calculated (e.g., at point 1614). In the example depicted in FIG. 24, the controller device 200 can prompt the user to take corrective action about 1 to 1.5 hours earlier, if the controller device 200 monitors the blood glucose data for patterns indicative of a missed meal situation, than if the controller device 200 monitors only the blood glucose level (refer to curve 1610). Such a feature can provide enhanced protection for the user, who would have the opportunity to consume a meal before the blood glucose level decreased below the normal range, potentially maintaining the user's blood glucose in a normal range when it would otherwise fall to an unsafe level.

Figure 25:
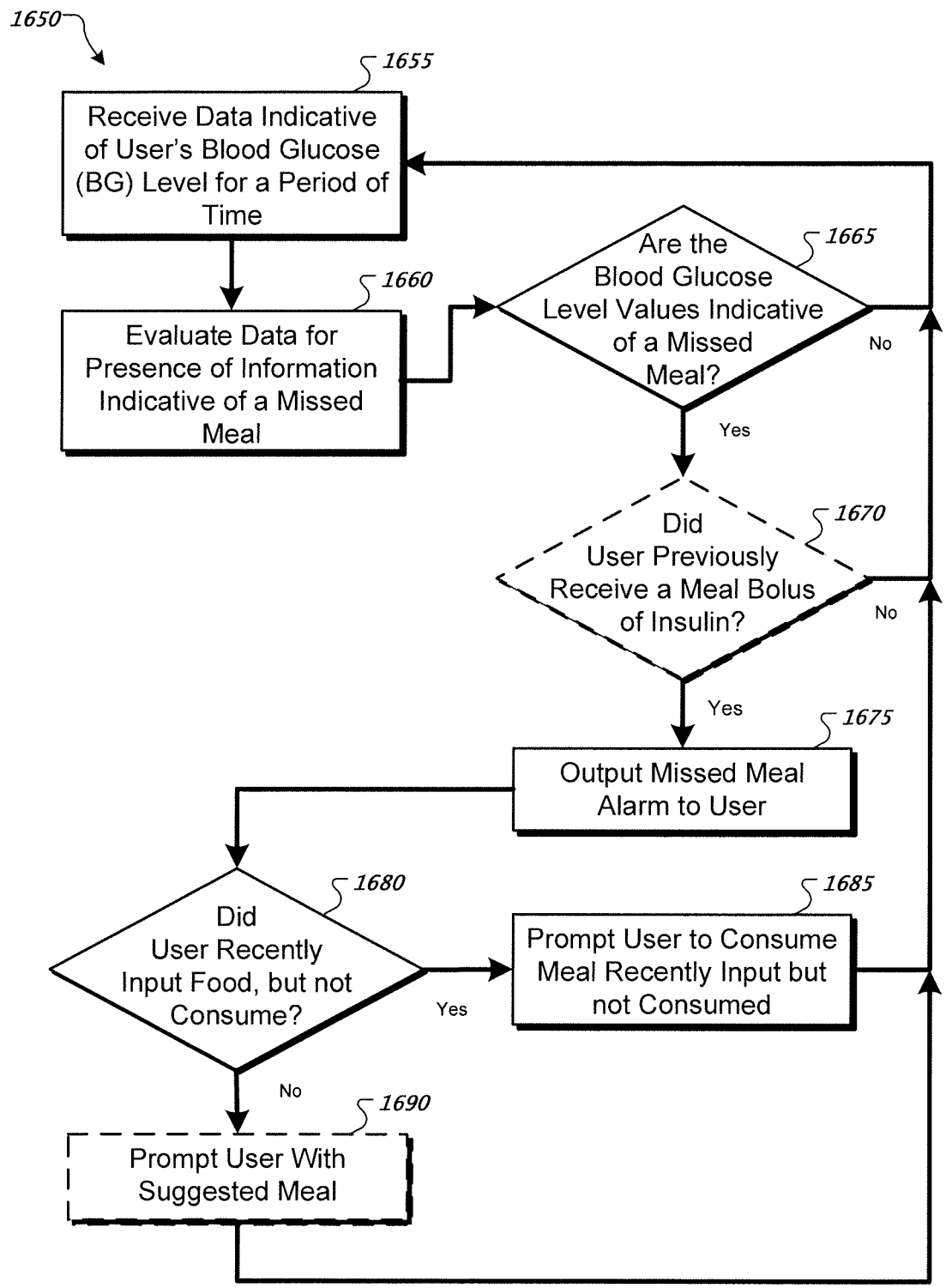
FIG. 25 is a flow diagram depicting an exemplary process used to identify a missed meal using blood glucose information, in some embodiments.

Referring now to FIG. 25, the controller device 200 can be used to identify a missed meal situation that can be indicative of, for example, the user receiving a bolus dosage of insulin to offset an entered meal of carbohydrates, but not consuming the entered meal. In some embodiments, a process 1650 for identifying a missed meal situation using blood glucose information can be implemented by the controller device 200. As previously described, the controller device 200 can receive and store information indicative of a user's blood glucose level. In operation 1655, the controller device 200 can receive data indicative of the user's blood glucose level for a period of time (e.g., one hour, two hours, three and a half hours, or the like) from memory (e.g., the memory chip 248). In operation 1660, the controller device 200 can evaluate the blood glucose data for the presence of information that is indicative of a missed meal situation. For example, the controller device 200 can locate local maxima as described previously in connection with FIG. 24. In another example, the controller device 200 can identify local maxima and apply additional tests, such as those described in connection with FIG. 24 (e.g., testing multiple points around a local maximum), to determine if data indicative of a missed meal situation is present. If, in operation 1665, the controller device 200 does not identify information indicative of a missed meal situation, the process 1650 can return to operation 1655 where the controller device 200 can standby to receive additional blood glucose data.

If the controller device 200, in operation 1665, does identify information indicative of a missed meal situation, the process 1650 can optionally execute process 1670 in which the controller device 200 can check if the user has recently (e.g., within the last 30 minutes, within the last 2 hours, within the last four hours, or the like) received a bolus dosage (e.g., a bolus dosage, intended to offset an entered meal). For example, a missed meal situation can be defined as a situation in which the user enters information about a consumed meal into the controller device 200, but neglects to consume the meal. In this example, the controller device 200 may not define a situation (e.g., sudden drop in blood glucose level) as a missed meal situation if a carbohydrate-offsetting bolus of insulin was not recently received by the user. In other examples, a missed meal situation can be identified even if a carbohydrate-offsetting bolus has not been received recently by the user. If, in optional operation 1670, the controller device 200 determines that the user has not recently received a bolus dosage, the process 1650 can return to operation 1655 where the controller device 200 can standby to receive additional blood glucose data.

If, in operation 1670, the controller device 200 determines that the user has recently received a bolus dosage of insulin, the process 1650 can execute operation 1675 and the controller device 200 can output a "missed meal" alarm to the user. In operation 1685, the controller device 200 can prompt the user to enter whether or not the user previously entered a meal, but neglected to consume it. For example, if the user did previously enter a meal and neglected to consume it, the user can indicate this to the controller device 200 and thus be prompted to consume the meal. However, if the user indicates that he/she has consumed all previously entered meals, this could be indicative of some other problem (e.g., an incorrectly entered meal), and the controller device 200 can optionally take additional action, such as suggesting an additional meal. In operation 1680, if the controller device 200 determines that the user did neglect to consume a previously entered meal, the controller device 200 can execute operation 1685, prompting the user to consume the recently entered meal, thereby correcting the missed meal situation before the user's blood glucose level falls below the lower alarm limit conditions. If, however, the controller device determines, in operation 1680, that the user has consumed all previously entered meals, the controller device 200 can optionally execute operation 1690, prompting the user with a suggested meal to be consumed. The suggested meal can be based on, as described in greater detail in connection with FIG. 24, the slope of a graph of the user's recent blood glucose information. Consuming a meal based on a "missed meal" alarm can correct, or prevent, a potentially unsafe drop in blood glucose level earlier than a correction based only on blood glucose level.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
   a glucose monitoring device; and
   an infusion pump in wireless communication with the glucose monitoring device, the infusion pump comprising:
      a disposable insulin delivery device comprising a portable pump housing that receives insulin for dispensation to a user, the pump housing at least partially containing a pump drive system to dispense the insulin through a flow path to the user, the pump drive system having a piston rod, a plunger, and a septum, the piston rod being adapted to advance the plunger to cause at least a portion of the insulin to advance through the septum when the flow path is established through the septum; and
      a reusable controller being configured to reversibly connect with the disposable insulin delivery device, the reusable controller comprising a display device and one or more user-selectable buttons, the reusable controller being adapted to communicate with the pump drive system to dispense the insulin, the reusable controller being adapted to receive wireless communications from the glucose monitoring device and display a user's blood glucose level and an indication of whether the user's blood glucose level is rising or falling on the display device, wherein the reusable controller is adapted to shuffle through a number of screens on the display device in response to user interaction with the one or more user-selectable buttons, the reusable controller being adapted to process insulin delivery data, the reusable controller being configured to calculate a total insulin load of the user representing an estimated amount of bolus and basal insulin delivered to the user's body which has not yet acted, wherein the reusable controller is adapted to use the user's blood glucose level and the calculated total insulin load to calculate and display a suggested bolus dosage on the display device to the user;
      wherein the system is adapted to process blood glucose information from the glucose monitoring device along with the insulin delivery data to determine if conditions indicate that the user skipped a bolus delivery for a meal the user consumed, wherein the system is configured to communicate information about detected missed boluses to the user.

2. The system of claim 1, wherein the disposable insulin delivery device and the reusable controller are configured to reversibly connect to form an insulin pump.

3. The system of claim 1, wherein the total insulin load is determined by the reusable controller according to a function that accounts for (i) a bolus insulin load indicative of one or more bolus insulin dosages that have been dispensed into the user but not yet acted in the user and (ii) a basal insulin load indicative of one or more basal insulin dosages that have been dispensed into the user from the medical infusion pump system but not yet acted in the user.

4. The system of claim 3, wherein the function further accounts for (iii) a previous food component based upon previous food intake that has not yet metabolized in the user.

5. The system of claim 1, wherein the reusable controller further comprises a computer-readable memory device coupled to the controller that stores the glucose information received from the glucose monitoring device and time values associated with the glucose information.

6. The system of claim 1, wherein the controller outputs a missed bolus alarm when the glucose information indicates that the blood glucose level increases above a glucose alarm limit parameter.

7. The system of claim 6, wherein the controller increases the glucose alarm limit parameter when the user's total insulin load is calculated to be greater than a predetermined insulin load range.

8. The system of claim 7, wherein the display device indicates when the glucose alarm limit parameter is adjusted in response to the user's total insulin load being greater than the predetermined insulin load range.

9. The system of claim 6, wherein the controller decreases the glucose alarm limit parameter when the user's total insulin load is calculated to be lower than a predetermined insulin load range.

10. The system of claim 9, wherein the display device indicates when the glucose alarm limit parameter is adjusted in response to the user's total insulin load being lower than the predetermined insulin load range.

11. The system of claim 6, wherein the display device indicates when the glucose alarm limit parameter is adjusted by the reusable controller in response to the total insulin load of the user.

12. The system of claim 11, wherein the display device contemporaneously displays a glucose value indicative of the user's blood glucose level and the calculated total insulin load of the user.

13. The system of claim 6, wherein the system suspends the missed bolus alarm during specified periods of the day.

14. The system of claim 1, wherein the display device contemporaneously displays the user's blood glucose level and the calculated total insulin load.

15. The system of claim 1, wherein the system outputs an alarm when the blood glucose level decreases below a lower glucose alarm limit parameter.

16. The system of claim 1, wherein the system outputs an alarm when the blood glucose level increases above an upper glucose alarm limit parameter, wherein the upper glucose alarm limit parameter is adjusted based on the insulin delivery data.

17. A method of operating an insulin infusion pump system, comprising:
- receiving glucose information indicative of a detected blood glucose level of a user;
- determining a total insulin load of the user indicative of an estimated amount of bolus and basal insulin delivered to the user's body which has not yet acted;
- calculating and displaying a suggested bolus dosage using the blood glucose level of the user and the determined total insulin load;
- processing the received glucose information along with insulin delivery data to determine if conditions indicate that the user skipped a bolus delivery for a meal the user consumed; and
- communicating information about the skipped bolus to the user.

18. The method of claim 17, further comprising activating a pump drive system to dispense the suggested bolus dosage through a flow path to the user in response to user input.

19. The method of claim 17, wherein the total insulin load is determined according to a function that accounts for (i) a bolus insulin load indicative of one or more bolus insulin dosages that have been dispensed into the user but not yet acted in the user and (ii) a basal insulin load indicative of one or more basal insulin dosages that have been dispensed into the user from the portable infusion pump system but not yet acted in the user.

20. The method of claim 19, wherein the function further accounts for (iii) a previous food component based upon previous food intake that has not yet metabolized in the user.

* * * * *